(12) United States Patent
Chou et al.

(10) Patent No.: US 11,408,028 B2
(45) Date of Patent: *Aug. 9, 2022

(54) NUCLEIC ACID HYBRIDIZATION ASSAY

(71) Applicant: Essenlix Corporation, Monmouth Junction, NJ (US)

(72) Inventors: Stephen Y. Chou, Princeton, NJ (US); Wei Ding, East Windsor, NJ (US); Ji Qi, Lawrence Township, NJ (US); Yufan Zhang, Princeton, NJ (US); Ji Li, Princeton, NJ (US)

(73) Assignee: Essenlix Corporation, Moumouth Junction, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/483,833

(22) PCT Filed: Feb. 8, 2018

(86) PCT No.: PCT/US2018/017494
§ 371 (c)(1),
(2) Date: Aug. 6, 2019

(87) PCT Pub. No.: WO2018/148463
PCT Pub. Date: Aug. 16, 2018

(65) Prior Publication Data
US 2020/0095629 A1   Mar. 26, 2020

Related U.S. Application Data

(60) Provisional application No. 62/460,083, filed on Feb. 16, 2017, provisional application No. 62/460,052, (Continued)

(51) Int. Cl.
*C12Q 1/68* (2018.01)
*C12Q 1/6837* (2018.01)
(Continued)

(52) U.S. Cl.
CPC ...... *C12Q 1/6837* (2013.01); *B01L 3/502715* (2013.01); *B01L 3/502761* (2013.01);
(Continued)

(58) Field of Classification Search
CPC .............. C12Q 1/686; C12Q 1/6837; C12Q 2565/501; C12Q 2565/515;
(Continued)

(56) References Cited

U.S. PATENT DOCUMENTS 10,324,009 B2 * 6/2019 Chou ............... G01N 35/00871
2003/0027352 A1 * 2/2003 Hooper ............... B01J 19/0093
436/169

(Continued)

FOREIGN PATENT DOCUMENTS

| EP | 0961110 A2 | 12/1999 |
| WO | 2006135437 A2 | 12/2006 |
| WO | 2008022332 A2 | 2/2008 |

OTHER PUBLICATIONS

Li et al. "Three-dimensional cavity nanoantenna coupled plasmonic nanodots for ultrahigh and uniform surface-enhanced Raman scattering over a large area", Optics Express, Feb. 28, 2011, 19(5): 3925-3936. (Year: 2011).*

*Primary Examiner* — Betty J Forman

(57) ABSTRACT

Provided herein is a method and device for performing a homogeneous nucleic acid detection assay. The device can contain a pair of plates where one of the plates comprises (i) surface amplification surface; and (ii) target-specific nucleic acid probes that are immobilized on said amplification surface and that specifically binds to a part of the target nucleic acid; and the second plate comprises a sample contact area comprising a reagent storage site that comprises target-specific nucleic acid detection agents that specifically binds to another part of the target nucleic acid. In some embodiments, the device can be read without a washing unbound label from the surface of the device.

48 Claims, 26 Drawing Sheets

Related U.S. Application Data filed on Feb. 16, 2017, provisional application No. 62/459,303, filed on Feb. 15, 2017, provisional application No. 62/459,337, filed on Feb. 15, 2017, provisional application No. 62/459,267, filed on Feb. 15, 2017, provisional application No. 62/456,904, filed on Feb. 9, 2017, provisional application No. 62/457,084, filed on Feb. 9, 2017, provisional application No. 62/457,075, filed on Feb. 9, 2017, provisional application No. 62/456,598, filed on Feb. 8, 2017.

(51) Int. Cl.
  *B01L 3/00* (2006.01)
  *B01L 7/00* (2006.01)
  *C12Q 1/686* (2018.01)
  *G01N 21/65* (2006.01)

(52) U.S. Cl.
  CPC ............... *B01L 7/52* (2013.01); *C12Q 1/686* (2013.01); *G01N 21/65* (2013.01); *B01L 2200/0647* (2013.01); *B01L 2300/0636* (2013.01); *B01L 2300/0816* (2013.01); *B01L 2300/0819* (2013.01); *B01L 2300/12* (2013.01); *B01L 2300/1805* (2013.01)

(58) Field of Classification Search
  CPC ......... C12Q 2537/101; B01L 3/502715; B01L 3/502761; B01L 7/52; B01L 3/5027; B01L 2400/0481; G01N 33/54366; G01N 21/01; G01N 21/65
  See application file for complete search history.

(56) References Cited

U.S. PATENT DOCUMENTS

| | | |
|---|---|---|
| 2006/0154248 A1 | 7/2006 | McGrew et al. |
| 2007/0254372 A1* | 11/2007 | Bickel .................... G01N 33/58 436/86 |
| 2014/0154668 A1* | 6/2014 | Chou .................... B82Y 15/00 435/5 |
| 2016/0003814 A1 | 1/2016 | Hamasaki et al. |

* cited by examiner

Cross-sectional view

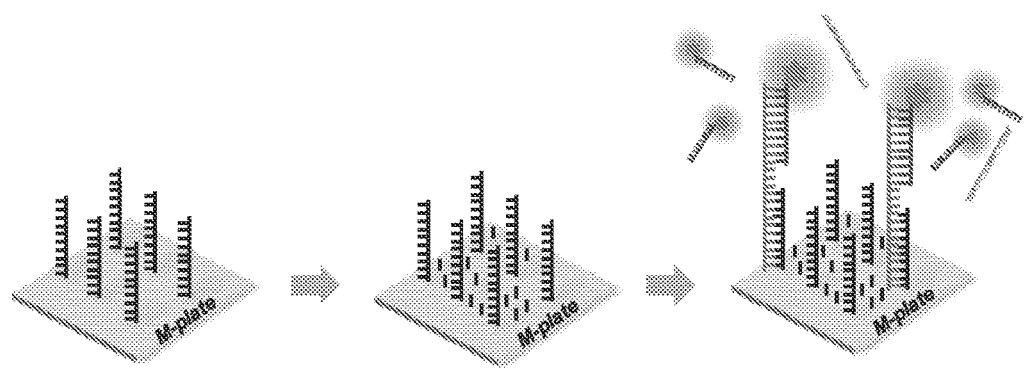
Fig. 3 (A) Coat M-plate surface with capture probe
Fig. 3 (B) Blocked with MCH
Fig. 3 (C) Target captured by coated capture probe and detected by labelled detection probe
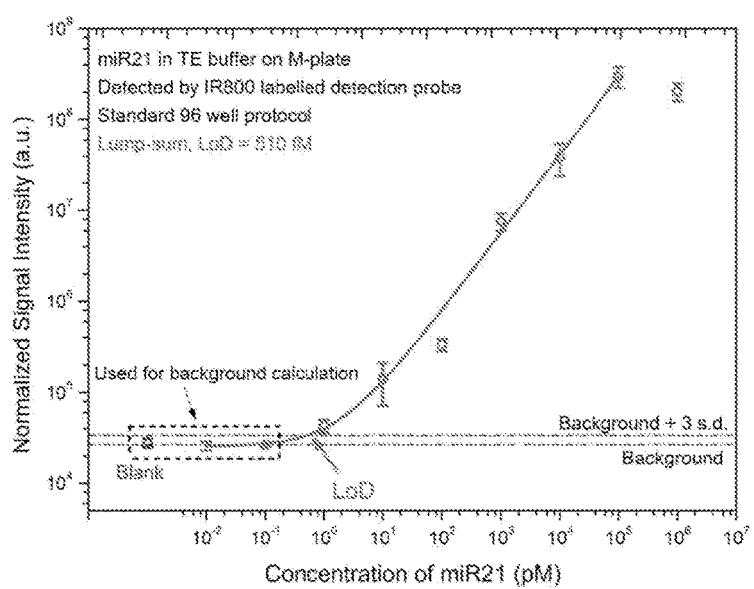
Fig. 4

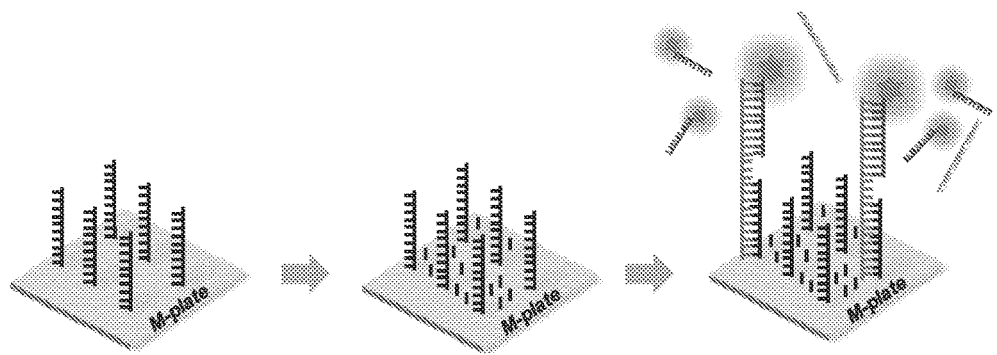
Fig. 5 (A) Coat M-plate surface with capture probe
Fig. 5 (B) Blocked with MCH
Fig. 5 (C) Target captured by coated capture probe and detected by labelled detection probe
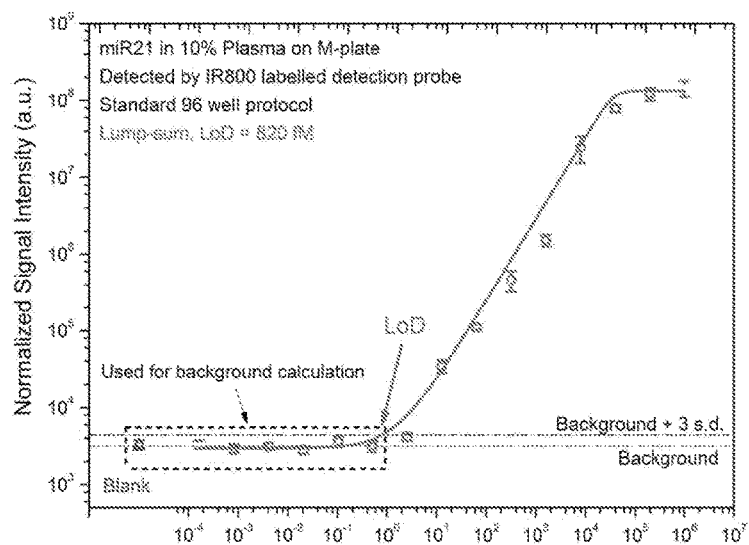
Fig. 6

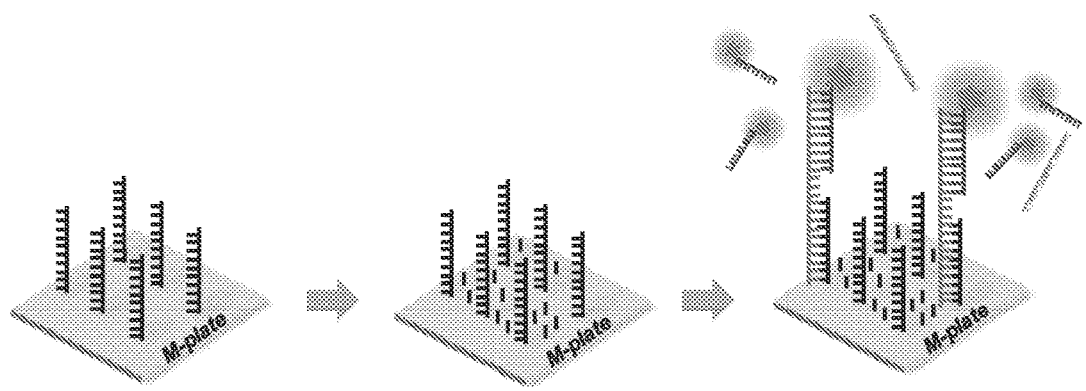
Fig. 7 (A) Coat M-plate surface with capture probe  Fig. 7 (B) Blocked with MCH  Fig. 7 (C) Target captured by coated capture probe and detected by labelled detection probe
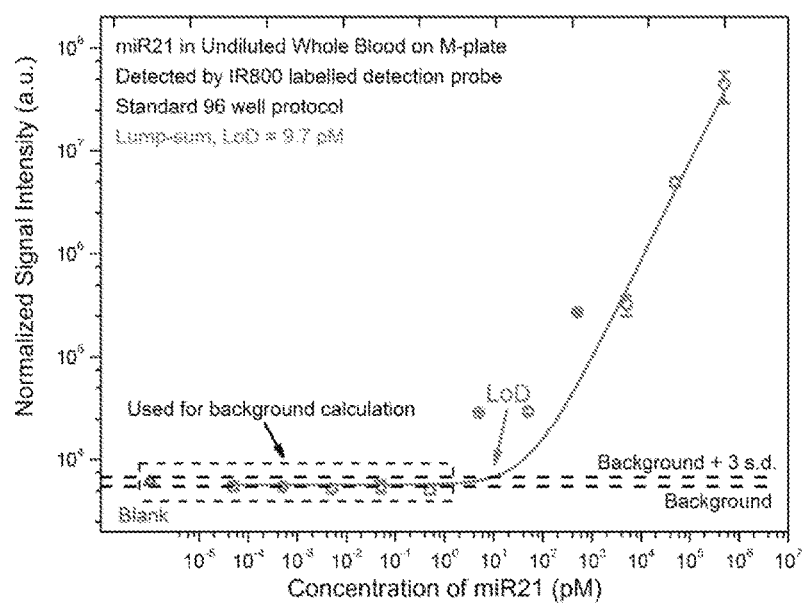
Fig. 8

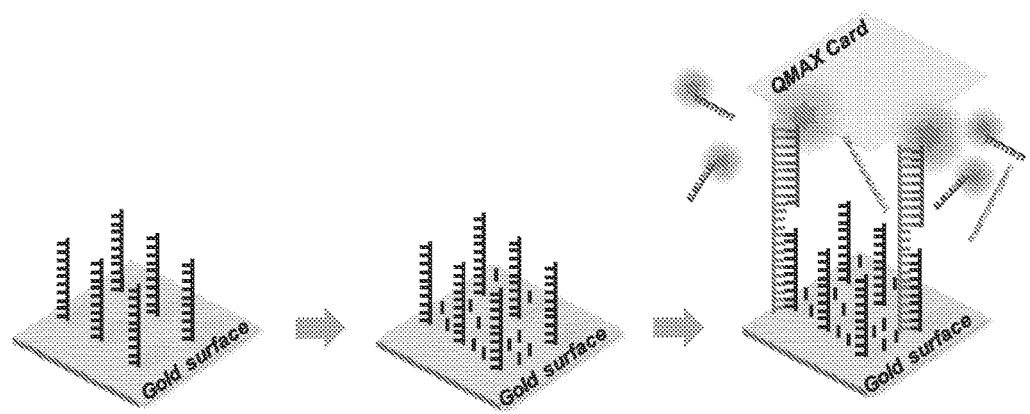
Fig. 9 (A) Coat gold surface with capture probe   Fig. 9 (B) Blocked with MCH   Fig. 9 (C) Target captured by coated capture probe and detected by labelled detection probe, pressed by 30um QMAX card
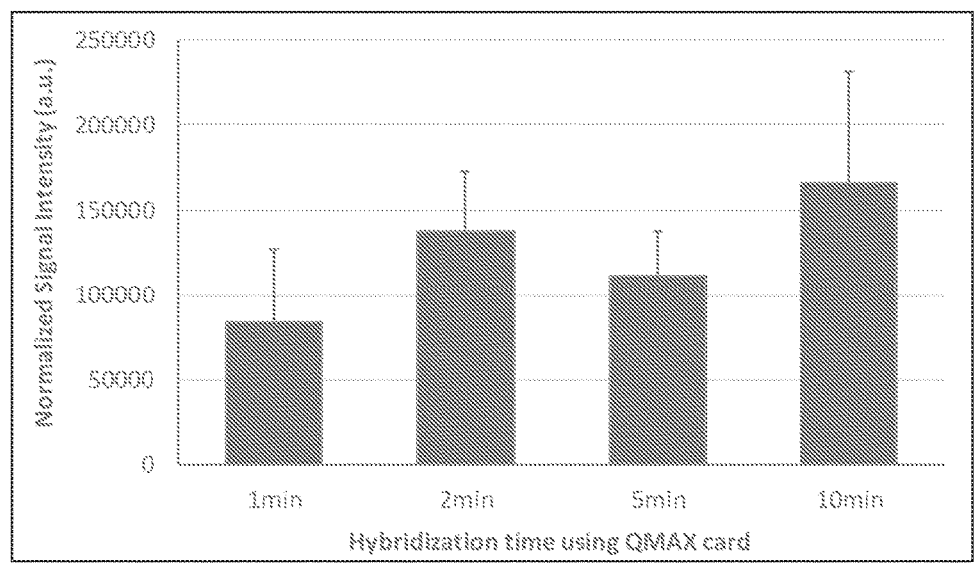
Fig.10

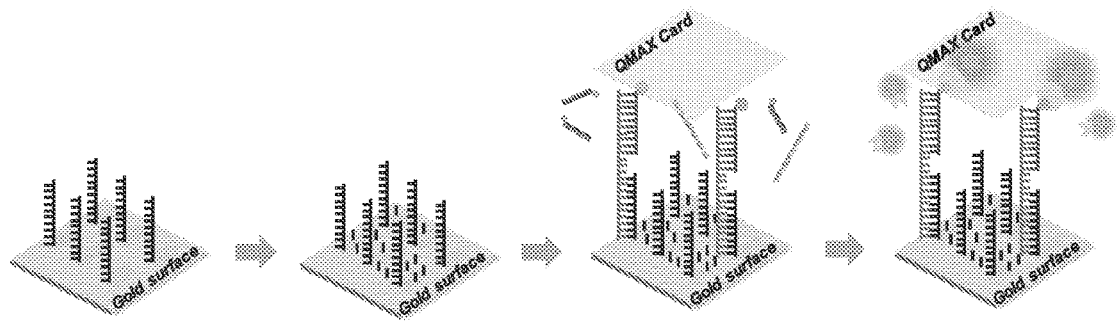
Fig. 11
(A) Coat gold surface with capture probe
Fig. 11
(B) Blocked with MCH
Fig. 11
(C) Target captured by coated capture probe and detected by biotinylated detection probe, pressed by 30um QMAX card
Fig. 11
(D) Detection probe detected by streptavidin-40nm bead conjugate
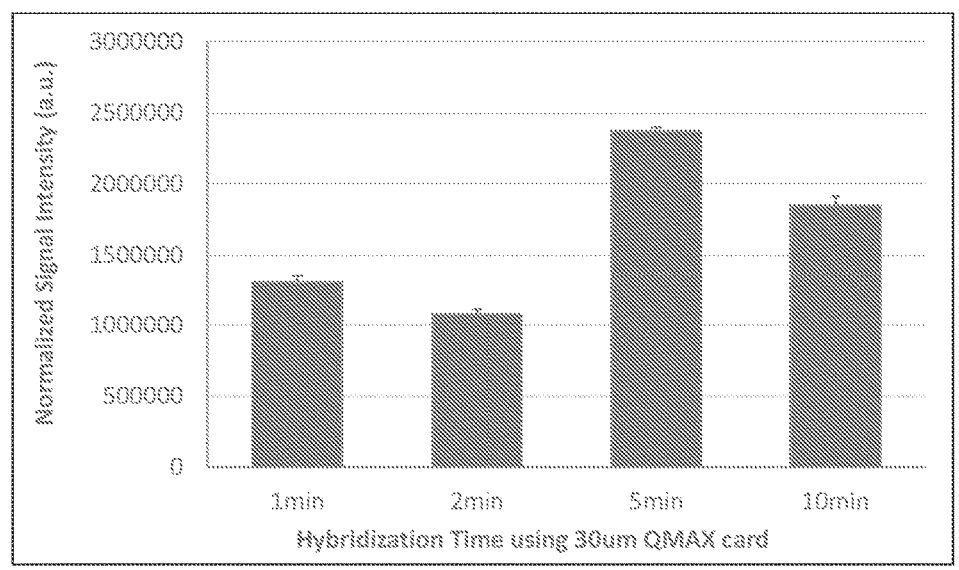
Fig. 12

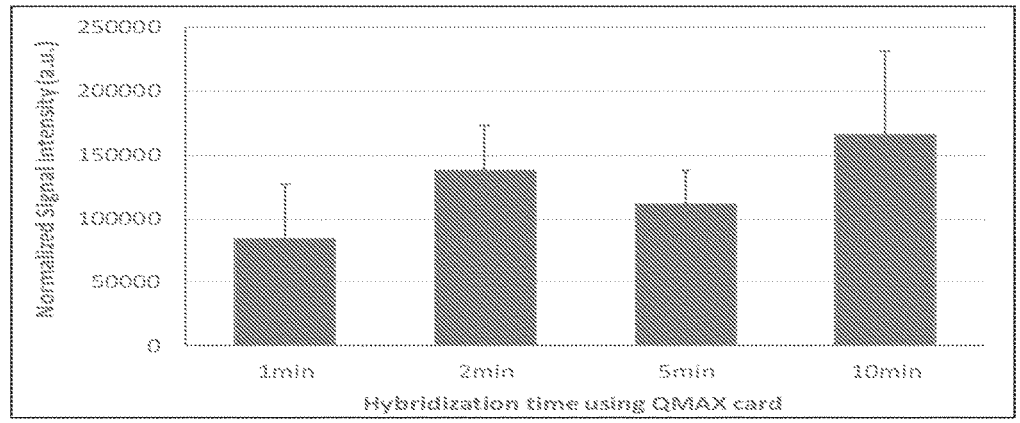
FIG. 13(A) Coat gold surface with capture probe    FIG. 13(B) Blocked with MCH    FIG. 13(C) Target captured by coated capture probe and detected by labelled detection probe, pressed by 30um QMAX card
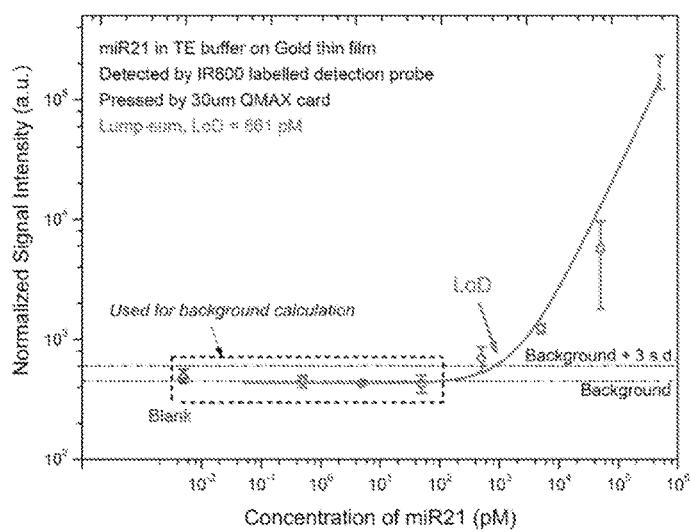
Fig. 14

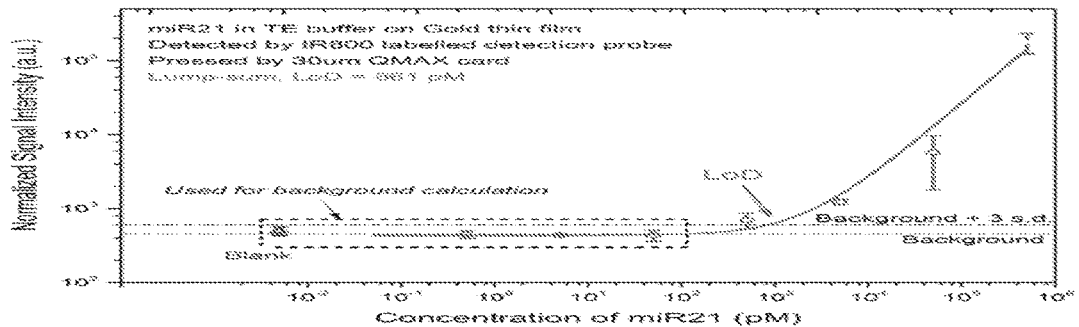
FIG. 15(A) Coat gold surface with capture probe
FIG. 15 (B) Blocked with MCH
FIG. 15 (C) Target captured by coated capture probe and detected by biotinylated detection probe, pressed by 30um QMAX card
FIG. 15 (D) Detection probe detected by streptavidin-40nm bead conjugate
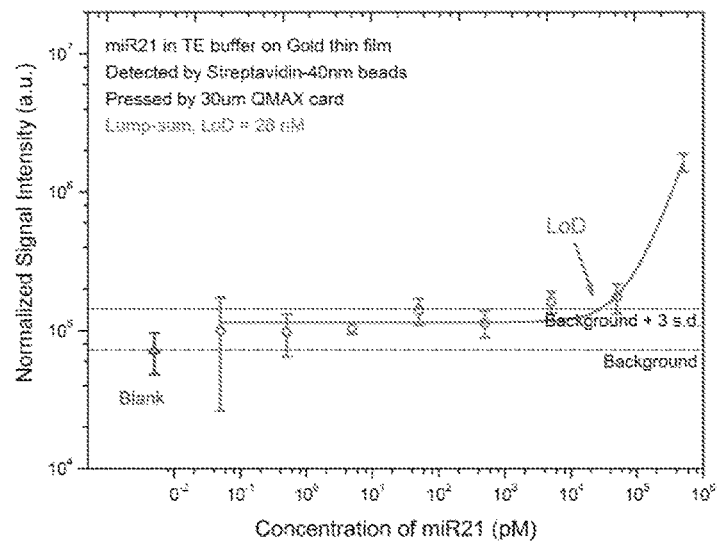
Fig. 16

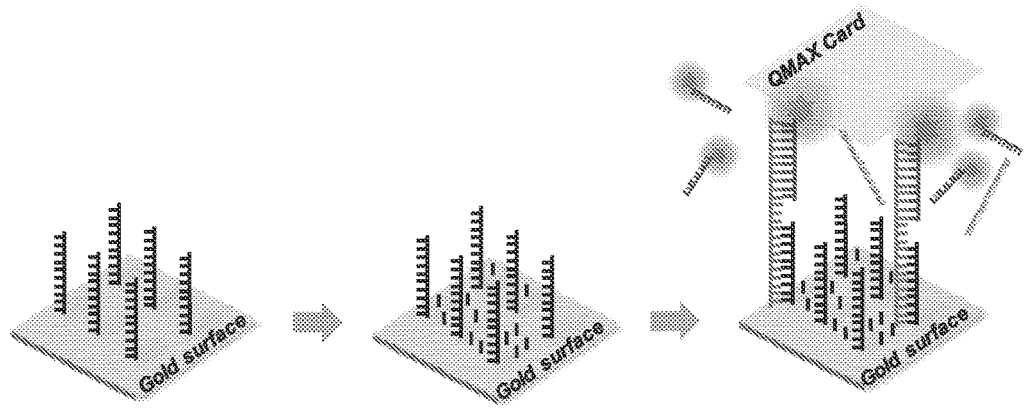
Fig. 17 (A) Coat gold surface with capture probe
Fig. 17 (B) Blocked with MCH
Fig. 17 (C) Target captured by coated capture probe and detected by labelled detection probe, pressed by 30um QMAX card
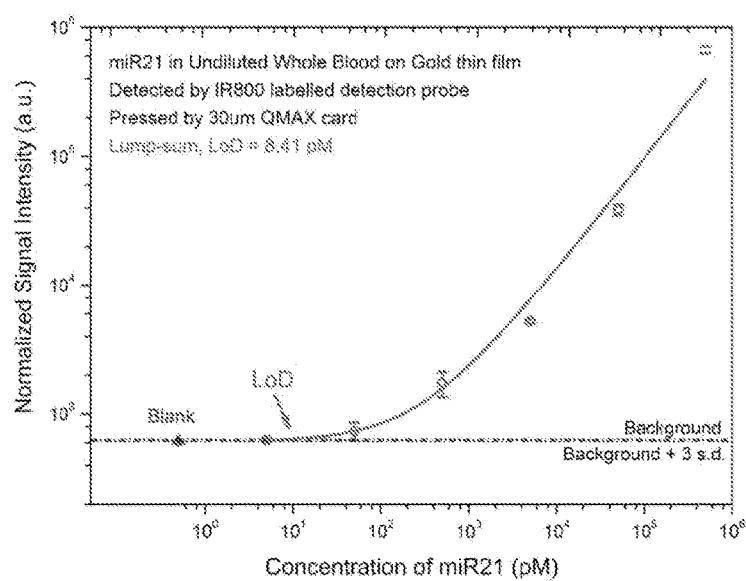
Fig. 18

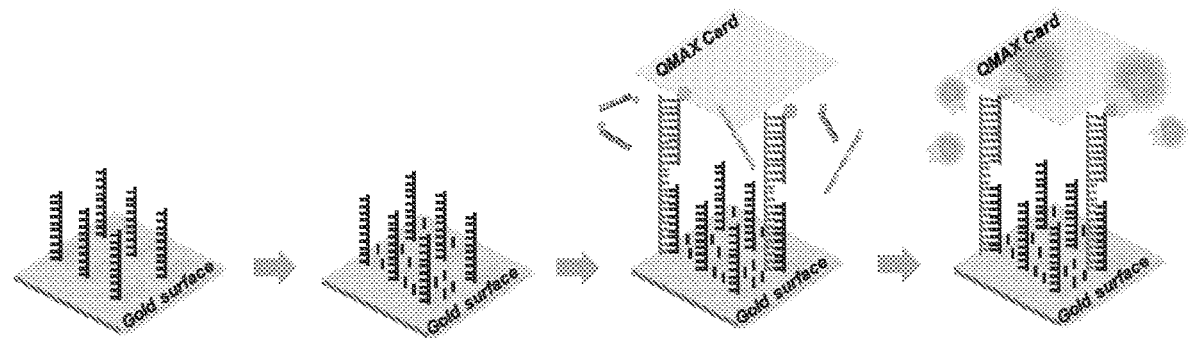
Fig. 19
(A) Coat gold surface with capture probe
Fig. 19
(B) Blocked with MCH
Fig. 19
(C) Target captured by coated capture probe and detected by biotinylated detection probe, pressed by 30um QMAX card
Fig. 19
(D) Detection probe detected by streptavidin-40nm bead conjugate
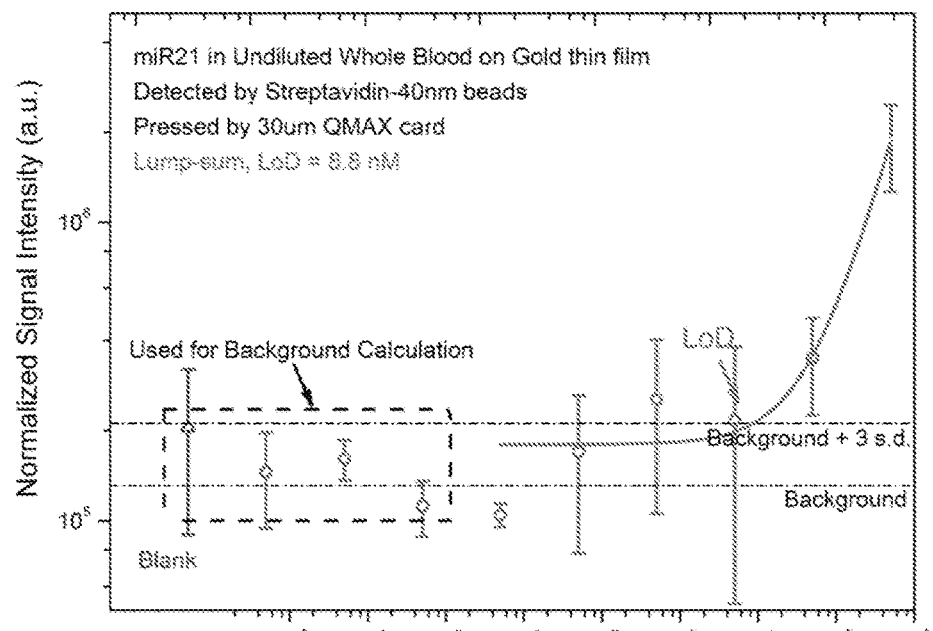
Fig. 20

(A) Coat gold surface with capture probe (B) Blocked with MCH (C) Target captured by coated capture probe and detected by biotinylated detection probe, pressed by 30um QMAX card (D) Detection probe detected by streptavidin-40nm bead conjugate

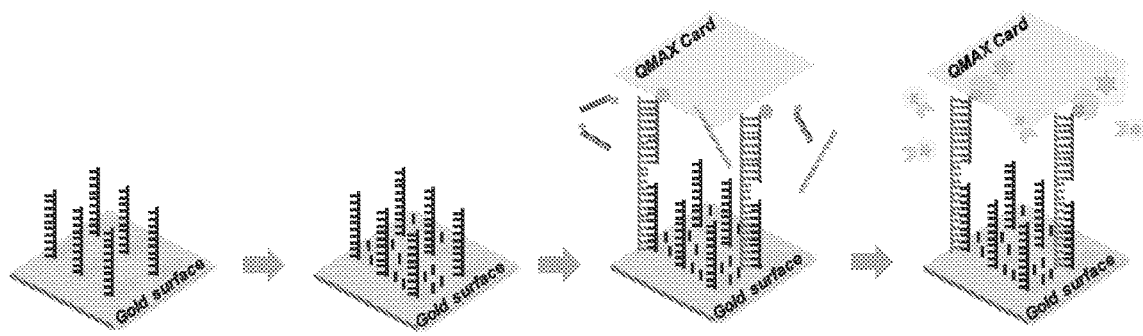
FIG. 23
(A) Coat gold surface with capture probe
FIG. 23
(B) Blocked with MCH
FIG. 23
(C) Target captured by coated capture probe and detected by biotinylated detection probe, pressed by 30um QMAX card
FIG. 23
(D) Detection probe detected by streptavidin-Cy5 conjugate
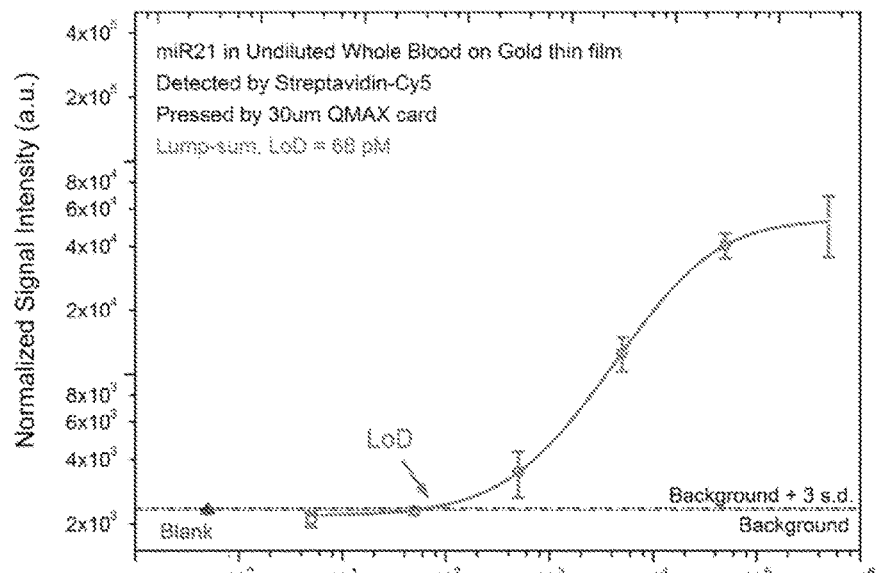
Fig. 24

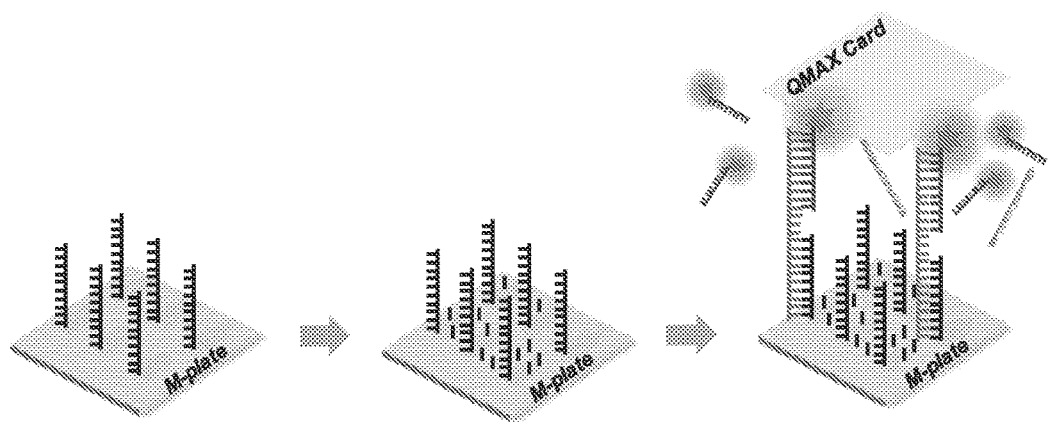
FIG. 25(A) Coat M-plate with capture probe
FIG. 25(B) Blocked with MCH
FIG. 25(C) Target captured by coated capture probe and detected by labelled detection probe, pressed by 30um QMAX card
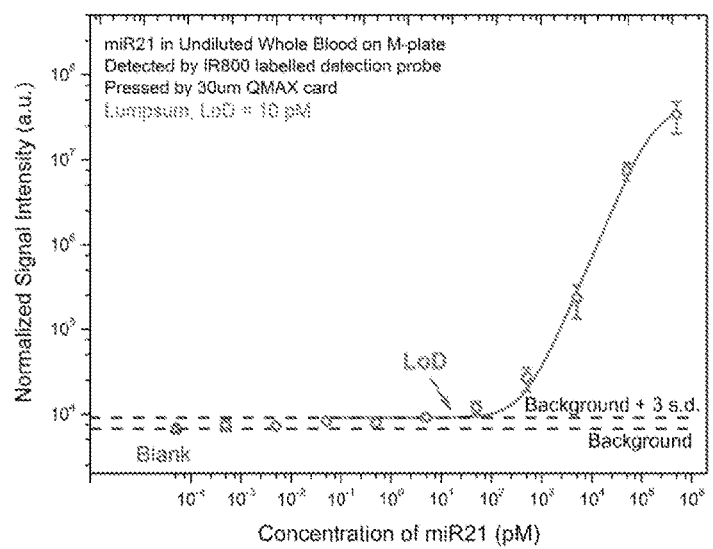
Fig. 26

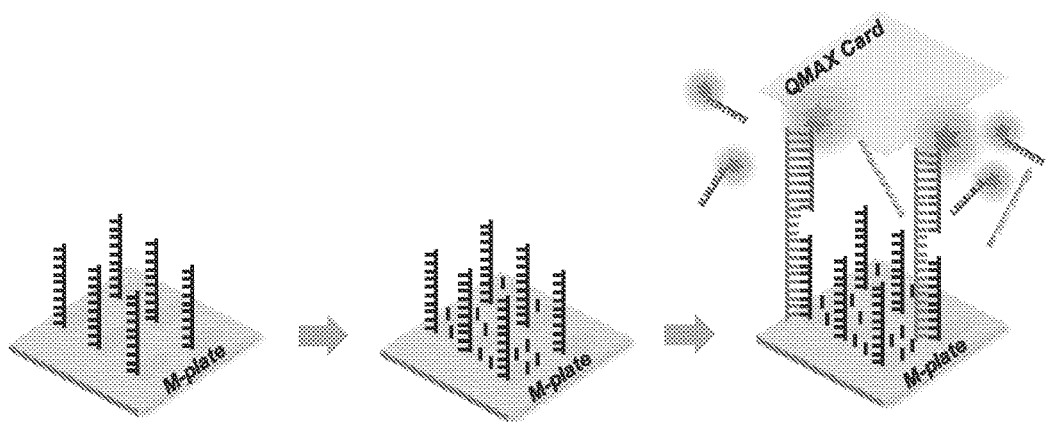
FIG. 27(A) Coat M-plate with capture probe    FIG. 27(B) Blocked with MCH    FIG. 27(C) Target captured by coated capture probe and detected by labelled detection probe, pressed by 30um QMAX card
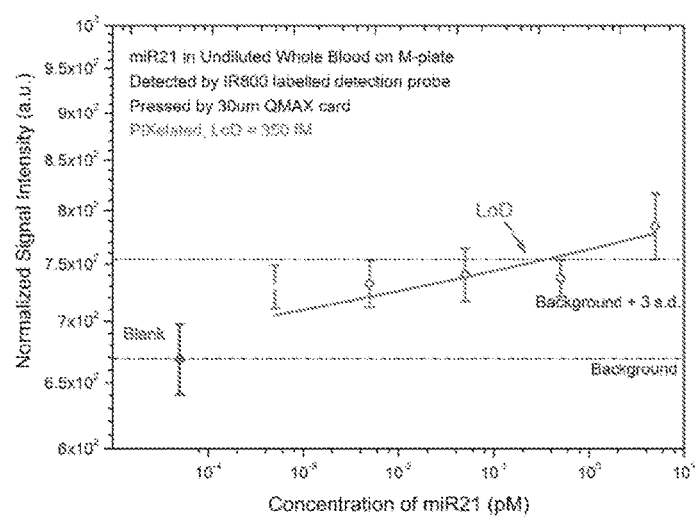
Fig. 28

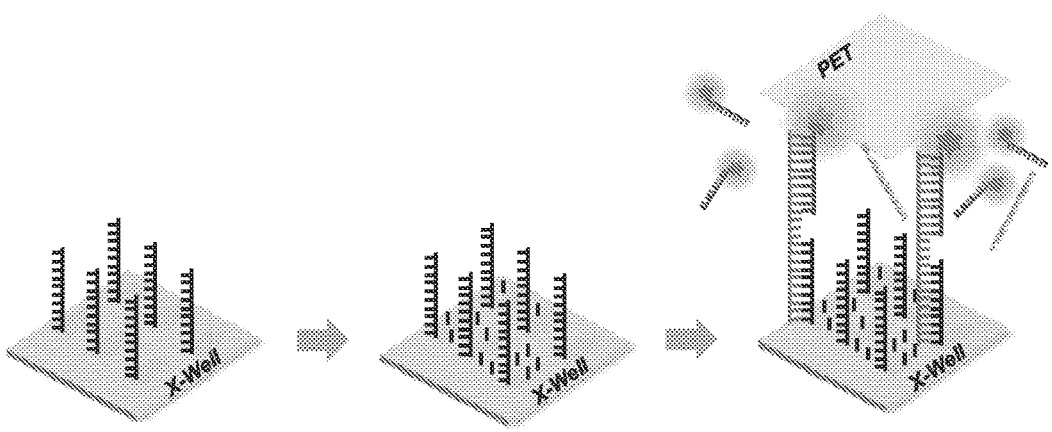
FIG. 29(A) Coat X-Well with capture probe
FIG. 29(B) Blocked with MCH
FIG. 29(C) Target captured by coated capture probe and detected by labelled detection probe, pressed by PET film
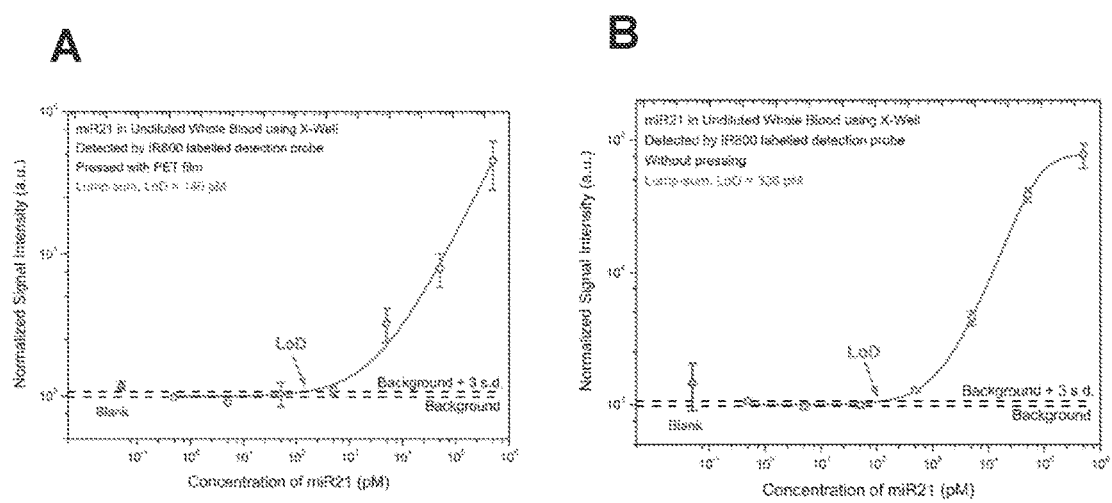
Fig. 30

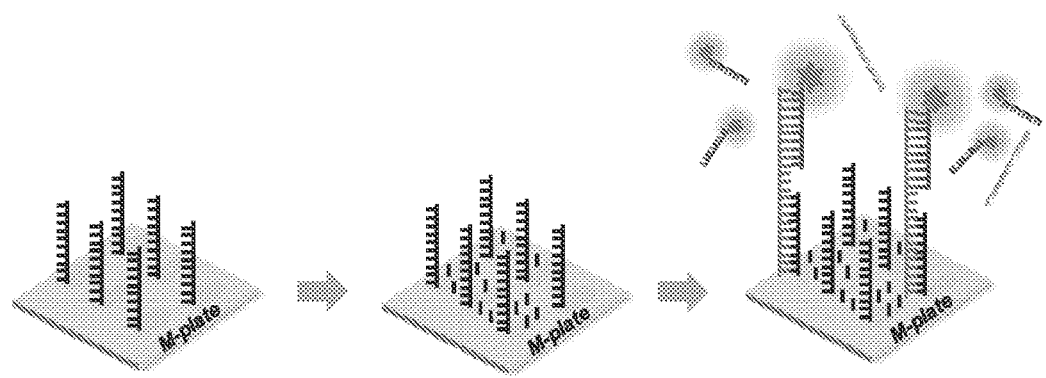

FIG. 31(A) Coat M-plate surface with capture probe

FIG. 31 (B) Blocked with MCH

FIG. 31 (C) Target captured by coated capture probe and detected by labelled detection probe

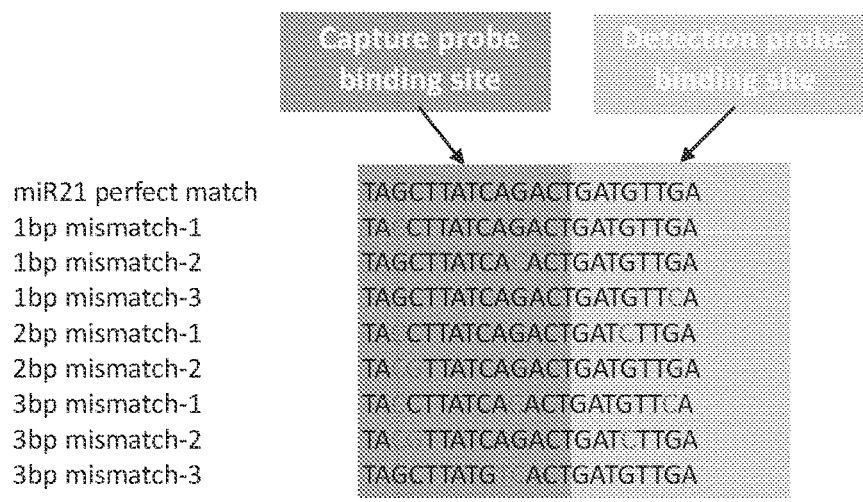

| | |
|---|---|
| miR21 perfect match | TAGCTTATCAGACTGATGTTGA |
| 1bp mismatch-1 | TA CTTATCAGACTGATGTTGA |
| 1bp mismatch-2 | TAGCTTATCA ACTGATGTTGA |
| 1bp mismatch-3 | TAGCTTATCAGACTGATGTT A |
| 2bp mismatch-1 | TA CTTATCAGACTGAT TTGA |
| 2bp mismatch-2 | TA TTATCAGACTGATGTTGA |
| 3bp mismatch-1 | TA CTTATCA ACTGATGTT A |
| 3bp mismatch-2 | TA TTATCAGACTGAT TTGA |
| 3bp mismatch-3 | TAGCTTATG ACTGATGTTGA |

Fig. 32

| Target | Normalized Signal Intensity (a.u.) | Fold Change |
|---|---|---|
| miR21 target (Perfect Match) | 1.76E+06 | -- |
| 1bp mismatch-1 | 5.09E+04 | 34.6 |
| 1bp mismatch-2 | 6.27E+05 | 2.8 |
| 1bp mismatch-3 | 2.36E+05 | 7.5 |
| 2bp mismatch-1 | 1.16E+04 | 151.5 |
| 2bp mismatch-2 | 2.39E+04 | 73.6 |
| 3bp mismatch-1 | 6.36E+03 | 276.6 |
| 3bp mismatch-2 | 6.71E+03 | 262.4 |
| 3bp mismatch-3 | 8.02E+03 | 219.5 |
| Background (no target) | 7.08E+03 | 248.7 |

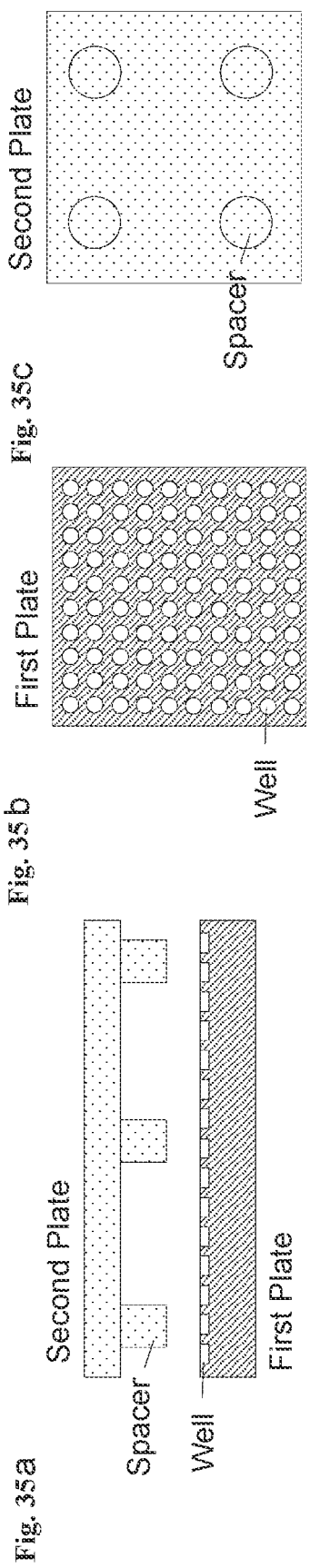

NUCLEIC ACID HYBRIDIZATION ASSAY

CROSS-REFERENCE TO RELATED APPLICATIONS

This application is a § 371 national stage application of International Application PCT/US2018/017494 filed on Feb. 8, 2018, which claims the benefit of priority to U.S. provisional application Ser. No. 62/456,598 filed on Feb. 8, 2017 (ESX-032PRV), 62/459,337 filed on Feb. 15, 2017, (ESX-033PRV2) 62/457,084 filed on Feb. 9, 2017 (ESX-017PRV), 62/459,267 filed on Feb. 15, 2017 (ESX-017PRV2), 62/456,904 filed on Feb. 9, 2017 (ESX-027PRV), 62/459,303 filed on Feb. 15, 2017 (ESX-027PRV2), 62/457,075 filed on Feb. 9, 2017 (ESX-035PRV), 62/460,052 filed on Feb. 16, 2017 (ESX-035PRV2) and 62/460,083 filed on Feb. 16, 2017 (ESX-035PRV3), the contents of which are relied upon and incorporated herein by reference in their entirety. The entire disclosure of any publication or patent document mentioned herein is entirely incorporated by reference.

FIELD

Among other things, the present invention is related to devices and methods of performing biological and chemical assays, such as but not limited to assays.

BACKGROUND

Traditional nucleic acid hybridization assay is complex, time-consuming, laborious and requires lab setups and significant amount of sample. For example, Southern Blot usually takes a few hours to complete. In addition, traditional nucleic acid hybridization assays require a relatively large volume of sample (typically >100 uL) that is not applicable in many situations in which samples are limited or scarce. Therefore, it is desirable to develop a fast, accurate, portable, and/or inexpensive nucleic acid hybridization assay that requires as little sample as possible. In addition, it is desirable that the assay can be conducted by a non-professional. The current invention satisfies these needs.

BRIEF DESCRIPTION OF THE DRAWINGS

The skilled artisan will understand that the drawings, described below, are for illustration purposes only. The drawings are not intended to limit the scope of the present teachings in any way. The drawings not are not entirely in scale. In the figures that present experimental data points, the lines that connect the data points are for guiding a viewing of the data only and have no other means.

FIG. 1A shows the perspective view of the plates in an open configuration when the plates are separated apart; FIG. 1B shows the perspective view and a sectional view of depositing a sample on the first plate at the open configuration; FIG. 1C shows the perspective view and a sectional view of the QMAX device in a closed configuration.

FIG. 3(A)-FIG. 3(C) shows an exemplary assay scheme of a nucleic acid hybridization assay of the present invention.

FIG. 4 shows the results of a nucleic acid hybridization assay based on the scheme as shown in FIG. 3(A)-FIG. 3(C).

FIG. 5(A)-FIG. 5(C) shows an exemplary assay scheme of a nucleic acid hybridization assay of the present invention.

FIG. 6 shows the results of a nucleic acid hybridization assay based on the scheme as shown in FIG. 5(A)-FIG. 5(C).

FIG. 7(A)-FIG. 7(C) shows an exemplary assay scheme of a nucleic acid hybridization assay of the present invention.

FIG. 8 shows the results of a nucleic acid hybridization assay based on the scheme as shown in FIG. 7(A)-FIG. 7(C).

FIG. 9(A)-FIG. 9(C) shows an exemplary assay scheme of a nucleic acid hybridization assay of the present invention.

FIG. 10 shows the results of a nucleic acid hybridization assay based on the scheme as shown in FIG. 9(A)-FIG. 9(C).

FIG. 11(A)-FIG. 11(D) shows an exemplary assay scheme of a nucleic acid hybridization assay of the present invention.

FIG. 12 shows the results of a nucleic acid hybridization assay based on the scheme as shown in FIG. 11(A)-FIG. 11(D).

FIG. 13(A)-FIG. 13(C) shows an exemplary assay scheme of a nucleic acid hybridization assay of the present invention.

FIG. 14 shows the results of a nucleic acid hybridization assay based on the scheme as shown in FIG. 13(A)-FIG. 13(C).

FIG. 15(A)-FIG. 15(D) shows an exemplary assay scheme of a nucleic acid hybridization assay of the present invention.

FIG. 16 shows the results of a nucleic acid hybridization assay based on the scheme as shown in FIG. 15(A)-FIG. 15(D).

FIG. 17(A)-FIG. 17(C) shows an exemplary assay scheme of a nucleic acid hybridization assay of the present invention.

FIG. 18 shows the results of a nucleic acid hybridization assay based on the scheme as shown in FIG. 17(A)-FIG. 17(C).

FIG. 19(A)-FIG. 19(D) shows an exemplary assay scheme of a nucleic acid hybridization assay of the present invention.

FIG. 20 shows the results of a nucleic acid hybridization assay based on the scheme as shown in FIG. 19(A)-FIG. 19(D).

FIG. 23(A)-FIG. 23(D) shows an exemplary assay scheme of a nucleic acid hybridization assay of the present invention.

FIG. 24 shows the results of a nucleic acid hybridization assay based on the scheme as shown in FIG. 23(A)-FIG. 23(D).

FIG. 25(A)-FIG. 25(C) shows an exemplary assay scheme of a nucleic acid hybridization assay of the present invention.

FIG. 26 shows the results of a nucleic acid hybridization assay based on the scheme as shown in FIG. 25(A)-FIG. 25(C).

FIG. 27(A)-FIG. 27(C) shows an exemplary assay scheme of a nucleic acid hybridization assay of the present invention.

FIG. 28 shows the results of a nucleic acid hybridization assay based on the scheme as shown in FIG. 27(A)-FIG. 27(C).

FIG. 29(A)-FIG. 29(C) shows an exemplary assay scheme of a nucleic acid hybridization assay of the present invention.

FIG. 30 shows the results of a nucleic acid hybridization assay based on the scheme as shown in FIG. 29(A)-FIG. 29(C).

FIG. 31(A)-FIG. 31(C) shows an exemplary assay scheme of a nucleic acid hybridization assay of the present invention.

FIG. 32 shows an exemplary design of miR21 nucleic acid sequences and mismatch sequences.

FIG. 35a-FIG. 35c shows how the device can be implemented using spacers.

FIG. 36a shows a top view of wells on first plate with (i) round shape with square lattice (ii) rectangle shape with square lattice (iii) triangle shape with hexagonal lattice (iv) round shape with aperiodicity. FIG. 36b shows a top view of well array on first plate with (i) no metal coating (ii) metal coating on bottom of the well (iii) metal coating on side wall of the well (iv) metal coating on both bottom and side wall of the well.

DETAILED DESCRIPTION OF EXEMPLARY EMBODIMENTS

Figure 1A:
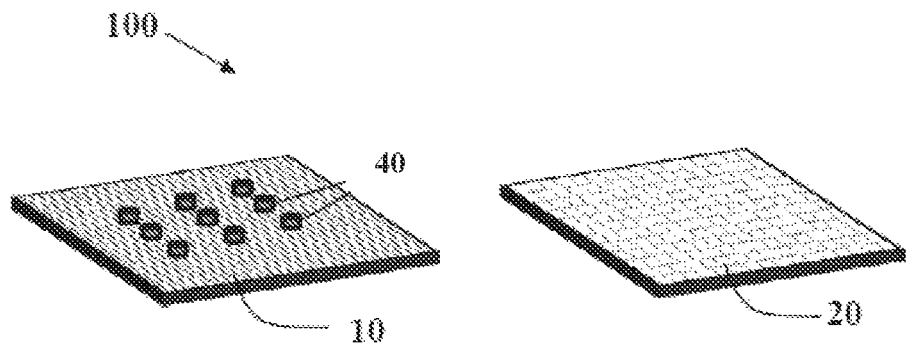
FIG. 1A-FIG. 1C shows an embodiment of a QMAX (Q: quantification; M: magnifying; A: adding reagents; X: acceleration; also known as compressed regulated open flow (CROF)) device, which comprises a first plate and a second plate.

The following detailed description illustrates some embodiments of the invention by way of example and not by way of limitation. The section headings and any subtitles used herein are for organizational purposes only and are not to be construed as limiting the subject matter described in any way. The contents under a section heading and/or subtitle are not limited to the section heading and/or subtitle, but apply to the entire description of the present invention.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

QMAX Device and Assay

In biological and chemical assaying (i.e. testing), a device and/or a method that simplifies assaying operation or accelerates assaying speed is often of great value.

In the QMAX (Q: quantification; M: magnifying; A: adding reagents; X: acceleration; also known as compressed regulated open flow (CROF)) assay platform, a QMAX card uses two plates to manipulate the shape of a sample into a thin layer (e.g. by compressing) (as illustrated in FIG. 1). In certain embodiments, the plate manipulation needs to change the relative position (termed: plate configuration) of the two plates several times by human hands or other external forces. There is a need to design the QMAX card to make the hand operation easy and fast.

In QMAX assays, one of the plate configurations is an open configuration, wherein the two plates are completely or partially separated (the spacing between the plates is not controlled by spacers) and a sample can be deposited. Another configuration is a closed configuration, wherein at least part of the sample deposited in the open configuration is compressed by the two plates into a layer of highly uniform thickness, the uniform thickness of the layer is confined by the inner surfaces of the plates and is regulated by the plates and the spacers.

In a QMAX assay operation, an operator needs to first make the two plates to be in an open configuration ready for sample deposition, then deposit a sample on one or both of the plates, and finally close the plates into a close position. In certain embodiments, the two plates of a QMAX card are initially on top of each other and need to be separated to get into an open configuration for sample deposition. When one of the plate is a thin plastic film (175 um thick PMMA), such separation can be difficult to perform by hand. The present invention intends to provide the devices and methods that make the operation of certain assays, such as the QMAX card assay, easy and fast.

One aspect of the present invention is to have a hinge that connect two or more plates together, so that the plates can open and close in a similar fashion as a book.

Another aspect of the present invention is to configure the material of the hinge, such that the hinge can self-maintain the angle between the plates after adjustment.

Another aspect of the present invention is to configure the material of the hinge, which maintain the QMAX card in the closed configuration, such that the entire QMAX card can be slide in and slide out a card slot without causing accidental separation of the two plates.

Another aspect of the present invention is to provide opening mechanisms such as but not limited to notches on plate edges or strips attached to the plates, making is easier for a user to manipulate the positioning of the plates, such as but not limited to separating the plates of by hand.

Another aspect of the present invention is to provide a hinge that can control the rotation of more than two plates.

The term "compressed open flow (COF)" refers to a method that changes the shape of a flowable sample deposited on a plate by (i) placing other plate on top of at least a part of the sample and (ii) then compressing the sample between the two plates by pushing the two plates towards each other; wherein the compression reduces a thickness of at least a part of the sample and makes the sample flow into open spaces between the plates. The term "compressed regulated open flow" or "CROF" (or "self-calibrated compressed open flow" or "SCOF" or "SCCOF") (also known as QMAX) refers to a particular type of COF, wherein the final thickness of a part or entire sample after the compression is "regulated" by spacers, wherein the spacers are placed between the two plates. Here the CROF device is used interchangeably with the QMAX device.

The term "spacers" or "stoppers" refers to, unless stated otherwise, the mechanical objects that set, when being placed between two plates, a limit on the minimum spacing between the two plates that can be reached when compressing the two plates together. Namely, in the compressing, the spacers will stop the relative movement of the two plates to prevent the plate spacing becoming less than a preset (i.e. predetermined) value.

The term "a spacer has a predetermined height" and "spacers have a predetermined inter-spacer distance" means, respectively, that the value of the spacer height and the inter spacer distance is known prior to a QMAX process. It is not predetermined, if the value of the spacer height and the inter-spacer distance is not known prior to a QMAX process. For example, in the case that beads are sprayed on a plate as spacers, where beads are landed at random locations of the plate, the inter-spacer distance is not predetermined. Another example of not predetermined inter spacer distance is that the spacers moves during a QMAX processes.

The term "a spacer is fixed on its respective plate" in a QMAX process means that the spacer is attached to a location of a plate and the attachment to that location is maintained during a QMAX (i.e. the location of the spacer on respective plate does not change) process. An example of "a spacer is fixed with its respective plate" is that a spacer is monolithically made of one piece of material of the plate, and the location of the spacer relative to the plate surface does not change during the QMAX process. An example of "a spacer is not fixed with its respective plate" is that a spacer is glued to a plate by an adhesive, but during a use of the plate, during the QMAX process, the adhesive cannot hold the spacer at its original location on the plate surface and the spacer moves away from its original location on the plate surface.

The term "open configuration" of the two plates in a QMAX process means a configuration in which the two plates are either partially or completely separated apart and the spacing between the plates is not regulated by the spacers The term "closed configuration" of the two plates in a QMAX process means a configuration in which the plates are facing each other, the spacers and a relevant volume of the sample are between the plates, the relevant spacing between the plates, and thus the thickness of the relevant volume of the sample, is regulated by the plates and the spacers, wherein the relevant volume is at least a portion of an entire volume of the sample.

The term "a sample thickness is regulated by the plate and the spacers" in a QMAX process means that for a give condition of the plates, the sample, the spacer, and the plate compressing method, the thickness of at least a port of the sample at the closed configuration of the plates can be predetermined from the properties of the spacers and the plate.

The term "inner surface" or "sample surface" of a plate in a QMAX device refers to the surface of the plate that touches the sample, while the other surface (that does not touch the sample) of the plate is termed "outer surface".

The term "height" or "thickness" of an object in a QMAX process refers to, unless specifically stated, the dimension of the object that is in the direction normal to a surface of the plate. For example, spacer height is the dimension of the spacer in the direction normal to a surface of the plate, and the spacer height and the spacer thickness means the same thing.

The term "area" of an object in a QMAX process refers to, unless specifically stated, the area of the object that is parallel to a surface of the plate. For example, spacer area is the area of the spacer that is parallel to a surface of the plate.

The term of QMAX device refers the device that perform a QMAX (e.g. CROF) process on a sample, and have or not have a hinge that connect the two plates.

The term "QMAX device with a hinge and "QMAX card" are interchangeable.

The term "angle self-maintain", "angle self-maintaining", or "rotation angle self-maintaining" refers to the property of the hinge, which substantially maintains an angle between the two plates, after an external force that moves the plates from an initial angle into the angle is removed from the plates.

The term "proximity-dependent signal amplification layer", "proximity-dependent signal amplification layer", or "surface signal amplification layer/surface" refers to a signal amplification layer that amplifies a signal from an analyte or a labeled analyte (e.g., a light-emitting label) in a proximity-dependent manner. In use of such a layer, the signal from an analyte or a labeled analyte increases the closer the molecule is to the surface of the signal amplification layer. As would be apparent, the magnitude of the signal produced by a first labeled molecule that is proximal to such a layer will be higher than the signal produced by a second labeled molecule that is distal to the layer. For example, the signal of a labeled molecule that is within 100 nm of a proximity-dependent signal amplification layer is greater than the signal of a labeled molecule that is 1 um or more away from the proximity-dependent amplification layer.

Signals can be detected using both "lump-sum" and "pixel-counting" methods. Lump sum methods are those in which the total signal produced by multiple binding events is determined. Pixel-counting methods are those that identify individual binding events and count them digitally.

In certain embodiments, the QMAX device is configured to have a detection sensitivity of 0.1 nM or less, such as 10 pM or less, or 1 pM or less, or 100 fM or less, such as 10 fM or less, including 1 fM or less, or 0.5 fM or less, or 100 aM or less, or 50 aM or less, or 20 aM or less. In certain embodiments, the QMAX device is configured to have a detection sensitivity in the range of 10 aM to 0.1 nM, such as 20 aM to 10 pM, 50 aM to 1 pM, including 100 aM to 100 fM. In some instances, the QMAX device is configured to be able to detect analytes at a concentration of 1 ng/mL or less, such as 100 pg/mL or less, including 10 pg/mL or less, 1 pg/mL or less, 100 fg/mL or less, 10 fg/mL or less, or 5 fg/mL or less. In some instances, the QMAX device is configured to be able to detect analytes at a concentration in the range of 1 fg/mL to 1 ng/mL, such as 5 fg/mL to 100 pg/mL, including 10 fg/mL to 10 pg/mL. In certain embodiments, the QMAX device is configured to have a dynamic range of 5 orders of magnitude or more, such as 6 orders of magnitude or more, including 7 orders of magnitude or more.

Examples of Wash-free Homogenous QMAX Devices

In these embodiments, near the top surface of substrate, there is an amplification zone, where only the label binding or very close to the substrates got enhanced.

The plates are moveable relative to each other into different configuration. One of the configurations is an open configuration, in which the two plates are partially or entirely separated apart and the spacing between the plates are not regulated by the spacers. In some embodiments, the inner surface of a respective plate comprises a sample contact area, which occupies a part of the entirety of the inner surface. In certain embodiments, the spacers are positioned within the sample contact area. In some embodiments, the spacers are not fixed to any one of the plates, but are mixed in the sample.

The sample is any liquid that needs testing. In some embodiments, the sample is a body fluid that is with or without processing or dilution. For example, the body fluid can be whole blood, blood plasma, serum, urine, saliva, sweat, or breath condensate. In some embodiments, the sample is blood. In certain embodiments, the sample comprises plasma. In certain embodiments, the sample comprises whole blood. In certain embodiments, the sample is a blood or plasma that has been diluted with buffer for 0.5, 1, 2, 3, 4, 5, 6, 7, 8, 9, 10, 20, 30, 40, 50, 60, 70, 80, 90, 100, 200, 300, 400, 500, 600, 700, 800, 900, 1,000, 5,000, 10,000, 50,000, 100,000, 500,000, or 1,000,000 times or in a range between any of the two values. In some embodiments, the sample comprises a target nucleic acid of any sequence, e.g., cfDNA, ctDNA, cfRNA, mirna, etc.

Without any intention to limit the use of the present method and device, in some embodiments, the method may be employed to identify a microbial pathogen from a clinical sample. In these embodiments, the target sequences may be from multiple different pathogens (e.g., at least 10 or at least 100 different pathogens), without knowing which pathogen is responsible for an infection, Microbes that might be identified using the present methods, compositions and kits include but are not limited to: a plurality of species of Gram (+) bacteria, plurality of species of Gram (−) bacteria, a plurality of species of bacteria in the family Enterobacteriaceae, a plurality of species of bacteria in the genus *Enterococcus*, a plurality of species of bacteria in the genus *Staphylococcus*, and a plurality of species of bacteria in the genus *Campylobacter*, *Escherichia coli* (*E. coli*), *E. coli* of various strains such as, K12-MG1655, CFT073, O157:H7 EDL933, O157:H7 VT2-Sakai, etc., *Streptococcus pneumoniae*, *Pseudomonas aeruginosa*, *Staphylococcus aureus*, coagulase-negative staphylococci, a plurality of *Candida* species including *C. albicans*, *C. tropicalis*, *C. dubliniensis*, *C. viswanathii*, *C. parapsilosis*, *Klebsiella pneumoniae*, a plurality of *Mycobacterium* species such as *M. tuberculosis*, *M. bovis*, *M. bovis* BCG, *M. scrofulaceum*, *M. kansasii*, *M. chelonae*, *M. gordonae*, *M. ulcerans*, *M. genavense*, *M. xenoi*, *M. simiae*, *M. fortuitum*, *M. malmoense*, *M. celatum*, *M. haemophilum* and *M. africanum*, *Listeria* species, *Chlamydia* species, *Mycoplasma* species, *Salmonella* species, *Brucella* species, *Yersinia* species, etc. Thus, the subject method enables identification of microbes to the level of the genus, species, sub-species, strain or variant of the microbe.

In some embodiments, examples of target nucleic acid sequences in sample may be from *Bacillus anthracis* (LF), *Giardia lamblia*, *Legionella*, Total Coliforms (including fecal coliform and *E. coli*), Viruses (enteric) stapylococci (e.g., *Staphylococcus epidermidis* and *Staphylococcus aureus* (enterotoxin A, B, C, G, I, cells, TSST-1), *Enterrococcus faecalis*, *Pseudomonas aeruginosa*, *Escherichia coli* (Shiga-like toxin, F4, F5, H, K, O, bacteriophage K1, K5, K13), other gram-positive bacteria, and gram-negative bacilli. *Clostridium difficile*, *Bacteroidetes*, *Cryptosporidium parvum* (GP900, p68 or cryptopain, oocyst), *Candida albicans*, *Bacillus anthracis*, *Bacillus stearothermophilus*, *Bacillus cereus*, *Bacillus licheniformis*, *Bacillus subtilis*, *Bacillus pumilus*, *Bacillus badius*, *Bacillus globigii*, *Salmonella typhimurium*, *Escherichia coli* O157:H7, Norovirus, *Listeria monocytogenes*, *Leptospira interrogans*, *Leptospira biflexa*, *Campylobacter jejuni*, *Campylobacter coli*, *Clostridium perfringens*, *Aspergillus flavus*, *Aspergillus parasiticus*, Ebola virus, *Histoplasma capsulatum*, *Blastomyces dermatitidis*, Gram-positive bacteria, Gram-negative bacteria (such as *Pseudomonas aeruginosa*, *Klebsiella pneumoniae*, *Salmonella enteriditis*, *Enterobacter aerogenes*, *Enterobacter hermanii*, *Yersinia enterocolitica* and *Shigella sonnei*), Polio virus, Influenza type A virus, Disease specific prion (PrP-d), Hepatitis A virus, *Toxoplasma gondii*, *Vibrio cholera*, *Vibrio parahaemolyticus*, *Vibrio vulnificus*, *Enterococcus faecalis*, *Enterococcus faecium*.

Other pathogens that can be detected in a diagnostic sample using the devices, systems and methods in the present invention include, but are not limited to: Varicella zoster, *Staphylococcus epidermidis*, *Escherichia coli*, methicillin-resistant *Staphylococcus aureus* (MSRA), *Staphylococcus aureus*, *Staphylococcus hominis*, *Enterococcus faecalis*, *Pseudomonas aeruginosa*, *Staphylococcus capitis*, *Staphylococcus warneri*, *Klebsiella pneumoniae*, *Haemophilus influenzae*, *Staphylococcus simulans*, *Streptococcus pneumoniae* and *Candida albicans*; gonorrhea (*Neisseria gorrhoeae*), syphilis (*Treponena pallidum*), clamydia (*Clamyda tracomitis*), nongonococcal urethritis (*Ureaplasm urealyticum*), chancroid (*Haemophilus ducreyi*), trichomoniasis (*Trichomonas vaginalis*); *Pseudomonas aeruginosa*, methicillin-resistant *Staphylococcus aureus* (MSRA), *Klebsiella pneumoniae*, *Haemophilis influenzae*, *Staphylococcus aureus*, *Stenotrophomonas maltophilia*, *Haemophilis parainfluenzae*, *Escherichia coli*, *Enterococcus faecalis*, *Serratia marcescens*, *Haemophilus parahaemolyticus*, *Enterococcus cloacae*, *Candida albicans*, *Moraxiella catarrhalis*, *Streptococcus pneumoniae*, *Citrobacter freundii*, *Enterococcus faecium*, *Klebsella oxytoca*, *Pseudomonas fluorscens*, *Neiseria meningitidis*, *Streptococcus pyogenes*, *Pneumocystis Klebsella pneumoniae Legionella pneumophila*, *Mycoplasma pneumoniae*, and *Mycobacterium tuberculosis*, etc., In particular embodiments, the sample may be obtained from a biological sample such as cells, tissues, bodily fluids, and stool. Bodily fluids of interest include but are not limited to, amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, urine and exhaled condensate. In particular embodiments, a sample may be obtained from a subject, e.g., a human, and it may be processed prior to use in the subject assay. For example, prior to analysis, the protein/nucleic acid may be extracted from a tissue sample prior to use, methods for which are known. In particular embodiments, the sample may be a clinical sample, e.g., a sample collected from a patient.

The label is a light-emitting label or an optical detectable label, directly or indirectly, either prior to or after it is bound to said capture agent. The label is label with signal of Raman scattering, chromaticity, luminescence, fluorescence, electroluminescence, chemiluminescence, and/or electrochemiluminescence. As used herein, the term "light-emitting label" refers to a label that can emit light when under an external excitation. This can be luminescence. Fluorescent labels (which include dye molecules or quantum dots), and luminescent labels (e.g., electro- or chemi-luminescent labels) are types of light-emitting label. The external excitation is light (photons) for fluorescence, electrical current for electroluminescence and chemical reaction for chemiluminscence. An external excitation can be a combination of the above. The phrase "labeled analyte" refers to an analyte that is detectably labeled with a light emitting label such that the analyte can be detected by assessing the presence of the label. A labeled analyte may be labeled directly (i.e., the analyte itself may be directly conjugated to a label, e.g., via a strong bond, e.g., a covalent or non-covalent bond), or a labeled analyte may be labeled indirectly (i.e., the analyte is bound by a secondary capture agent that is directly labeled).

The amplification layer amplifies a signal from the target analyte or a label of the target analyte when the target analyte or label is 1 nm, 10 nm, 20 nm, 30 nm, 40 nm, 50 nm, 60 nm, 70 nm, 80 nm, 90 nm, 100 nm, 200 nm, 300 nm, 400 nm, 500 nm, 1 um, 2 um, 5 um, 10 um from the amplification layer, or a range between any two of the values; and a preferred range of 1 nm to 50 nm, 50 nm to 100 nm, 100 nm to 200 nm, 200 nm to 500 nm.

The term "amplify" refers to an increase in the magnitude of a signal, e.g., at least a 10-fold increase, at least a 100-fold increase at least a 1,000-fold increase, at least a 10,000-fold increase, or at least a 100,000-fold increase in a signal.

In some embodiments, the proximity-dependent signal amplification layer includes, but not limited to, the proximity-dependent signal amplification layers described in U.S. Provisional Patent Application No. 61/347,178, which was filed on May 21, 2010, U.S. Provisional Patent Application No. 61/622,226, which was filed on Apr. 10, 2012, U.S. Provisional Patent Application No. 61/708,314, which was filed on Oct. 1, 2012, U.S. Provisional Patent Application No. 61/800,915, which was filed on Mar. 15, 2013, U.S. Provisional Patent Application No. 61/801,933, which was filed on Mar. 15, 2013, U.S. Provisional Patent Application No. 61/801,096, which was filed on Mar. 15, 2013, U.S. Provisional Patent Application No. 61/801,424, which was filed on Mar. 15, 2013, U.S. Provisional Patent Application No. 61/794,317, which was filed on Mar. 15, 2013, U.S. Provisional Patent Application No. 62/090,299, which was filed on Dec. 10, 2014, U.S. Provisional Patent Application No. 62/066,777, which was filed on Oct. 21, 2014, U.S. Provisional Patent Application No. 62/234,538, which was filed on Sep. 29, 2015, U.S. Utility patent application Ser. No. 13/699,270, which was filed on Jun. 13, 2013, U.S. Utility patent application Ser. No. 13/838,600, which was filed on Mar. 15, 2013, U.S. Utility patent application Ser. No. 14/459,239, which was filed on Aug. 13, 2014, U.S. Utility patent application Ser. No. 14/459,251, which was filed on Aug. 13, 2014, U.S. Utility patent application Ser. No. 14/852,412, which was filed on Mar. 16, 2014, U.S. Utility patent application Ser. No. 14/871,678, which was filed on Sep. 30, 2015, U.S. Utility patent application Ser. No. 14/431,266, which was filed on Oct. 5, 2015, U.S. Utility patent application Ser. No. 14/668,750, which was filed on Mar. 25, 2015, U.S. Utility patent application Ser. No. 14/775,634, which was filed on Sep. 11, 2015, U.S. Utility patent application Ser. No. 14/775,638, which was filed on Sep. 11, 2015, U.S. Utility patent application Ser. No. 14/852,417, which was filed on Sep. 11, 2015, U.S. Utility patent application Ser. No. 14/964,394, which was filed on Dec. 9, 2015, PCT Application (designating U.S.) No. PCT/US2011/037455, which was filed on May 20, 2011, PCT Application (designating U.S.) No. PCT/US2013/032347, which was filed on Mar. 15, 2013, PCT Application (designating U.S.) No. PCT/US2013/062923, which was filed on Oct. 1, 2013, PCT Application (designating U.S.) No. PCT/US2014/030108, which was filed on Mar. 16, 2014, PCT Application (designating U.S.) No. PCT/US2014/029675, which was filed on Mar. 14, 2014, PCT Application (designating U.S.) No. PCT/US2014/028417, which was filed on Mar. 14, 2014, PCT Application (designating U.S.) No. PCT/US2014/029979, which was filed on Mar. 15, 2014, PCT Application (designating U.S.) No. PCT/US2015/056518, which was filed on Oct. 20, 2015, PCT Application (designating U.S.) No. PCT/US2016/054025, which was filed on Sep. 27, 2016, the complete disclosures of which are hereby incorporated by reference for all purposes.

The signal amplification layer may comprise a continuous metallic film that is made of a material selected from the group consisting of gold, silver, copper, aluminum, alloys thereof, and combinations thereof. The signal amplification layer comprises high-amplification regions and low-amplification regions, wherein the high-amplification regions amplify signals at said surface more than the low-amplification regions, wherein the low-amplification regions of the layer have been selectively masked, wherein the signal amplification layer comprises (i) two or more protrusions, (ii) two or more metal metallic structures, and (iii) two or more gaps between the metallic structures; thereby increasing the probability that a target analyte will bind to a high-amplification region and be detected.

The signal amplification layer may comprise:
(i) a substantially continuous metallic backplane on the substrate;
(ii) one or a plurality of dielectric or semiconductor pillars extending from the metallic backplane or from the substrate through holes in the backplane; and
(iii) a metallic disk on top of the pillar, wherein at least one portion of the edge of the disk is separated from the metallic backplane by a gap;
wherein the gap(s) and portion of the metal edges are a part of the high signal amplification area, wherein the metallic disk has a shape selected from the group of shapes consisting of round, polygonal, pyramidal, elliptical, elongated bar shaped, or any combination thereof. The metallic disc is separated from the metallic film by a distance in the range of 0.5 to 30 nm, and the average lateral dimension of the discs is in the range of 20 nm to 250 nm; wherein the signal amplification layer comprises one or more metallic discs has a shape selected from the group of shapes consisting of round, polygonal, pyramidal, elliptical, elongated bar shaped, or any combination thereof, wherein the average lateral dimension of the discs is in the range 20 nm to 250 nm, and the gap between adjacent discs in the range of 0.5 to 30 nm.

wherein the metallic structures are made of a material that is selected from the group consisting of gold, silver, copper, aluminum, alloys thereof, and combinations thereof.

wherein the pillars are periodic or aperiodic, or the metallic structures have a random shape.

wherein the signal that is amplified is Raman scattering, chromaticity, luminescence, fluorescence, electroluminescence, chemiluminescence, and/or electrochemiluminescence.

QMAX device's first plate may further comprise a molecular linking layer that links said capture agents with said signal amplification layer, wherein said molecular adhesion layer is a self-assembled monolayer (SAM), wherein each molecule of the SAM comprises three parts: (i) a head group that has specific affinity to the signal amplification layer, (ii) a terminal group that specific affinity to the capture agent, and (iii) a linker that links the head group and terminal group, wherein the length of the linker determines the average spacing between the metal signal amplification layer and an attached capture agent can affects light amplification of the device.

QMAX device's second plate sample contact area may comprise a storage site containing detection agents that upon contacting the sample, dissolves into the sample and diffuses in the sample, wherein each capture agent, target analyte and corresponding detection agent is capable of forming a capture agent-target analyte-detection agent sandwich in a binding site of the first plate.

The device of any prior paragraph, wherein the second plate sample contact area comprises a storage site containing detection agents that upon contacting the sample, dissolves into the sample and diffuses in the sample, wherein the detection agent binds to the capture agent and competitively inhibits the binding between the capture agent and the target analyte.

In some embodiments, the enhancement mechanism of fluorescence label is known as Plasmonic enhancement. The enhanced fluorescence intensity due to the proximity of metal nanostructures makes it possible to detect much lower concentrations of biomarkers tagged with fluorescence molecule either in sensing format or for tissue imaging. Metal enhanced fluorescence (MEF) arises from an increased excitation rate due to an enhanced local field experienced by the fluorophore, and the electromagnetic coupling of the fluorophore with the near-by metal nanoparticle. Therefore, metal nanostructures are able to produce desirable effects such as increased fluorescence quantum yield, decreased lifetime and better fluorophore photostability. During the past decade a number of existing and novel nanoparticles and structures have appeared in the literature designed to improve both the fluorescence intensity and photo stability of fluorophores through MEF. Metal nanostructures have long been researched due to their ability to manipulate incident light. Localised surface plasmons (LSP) are charge density oscillations confined to metallic nanostructures and nanoparticles. If a particle is considered then an external field is able to displace the free electrons in the metal nanoparticle with respect to the fixed ionic core. This displacement sets up a restoring force leading to coherent oscillations of the charge density. This is termed the Localised Surface Plasmon Resonance (LSPR). LSPR is responsible for the electromagnetic-field enhancement that is thought to lead to surface enhanced Raman scattering (SERS). When it was observed that fluorescent molecules showed enhanced emissions in the presence of this plasmonic effect the field of MEF was born. A representation of the different optical responses that occur when light is absorbed and scattered by a metal nanoparticle can be seen. Due to above mechanism, the plasmonic effect and related enhancement are near the surface between 10 nm to 200 nm.

As noted above, in some embodiments, the method is done without washing where, a washing step is a process that removes at least 30%, 40%, 50%, 60%, 70%, 80%, 90%, 100% or a range between any two of the values of the unbounded target analyte on the first plate after binding step. Typically, the washing step contains washing the plate with 1 times, 2 times, 3 times with a buffer.

In some embodiments, the second plate sample contact area comprises a storage site containing detection agents that upon contacting the sample, dissolves into the sample and diffuses in the sample, wherein each capture agent, target analyte and corresponding detection agent is capable of forming a capture agent-target analyte-detection agent sandwich in a binding site of the first plate.

Theoretical Analyze of Sensitivity of Wash-Free Homogeneous QMAX Assay

Define final capture density (directly related to LoD or sensitivity of the assay) of the target analyte (with label) on the substrate (first plate) is $d_c$;

Define the label density in the liquid is $D_L$;

Define amplification factor is A;

Define amplification factor is uniform within $L_A$ of the substrate;

Define liquid height is by X-Plate is $L_X$ ($L_X \gg L_A$);

Define the label signal intensity's standard deviation (sd) of the liquid is σ;

Since signal from capture fluorophore must be larger than (1+3×sd)×background signal from liquid, thus:

$$Ad_c \geq (1+3\sigma)(D_L L_X + AD_L L_A)$$

The smallest capture density (proportional to LoD) detectable with this method is:

$$d_c = \frac{(1+3\sigma)(L_X + AL_A)D_l}{A}$$

Clearly, increase amplification factor (A) of substrate, decrease QMAX thickness ($L_X$) can improve the performance (sensitivity) of wash-free homogeneous assay in QMAX card format. But decrease the QMAX thickness might decrease the binding amount. Thus there is a trade-off for the parameter of QMAX gap size or liquid thickness.

Examples of QMAX Device for Nucleic Acid Hybridization Assay

Figure 2:
FIG. 2A-FIG. 2H is an illustration of an exemplary nucleic acid hybridization assay according to some embodiments of the present invention.
Figure 2:
Figure 2:
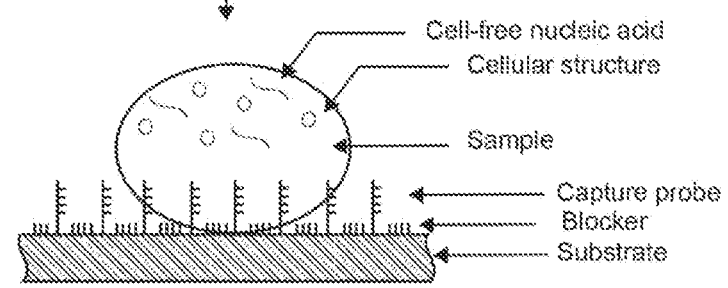
Figure 2:
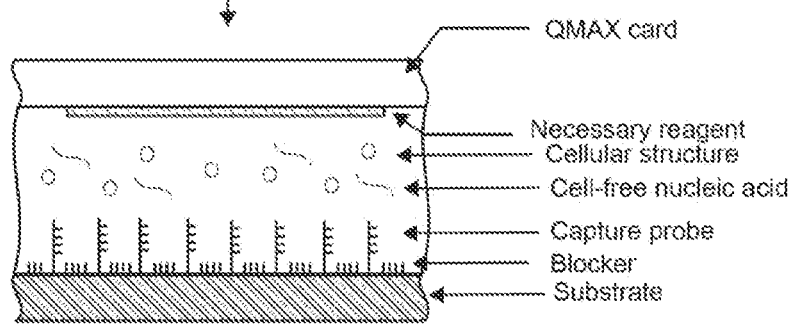
Figure 2:
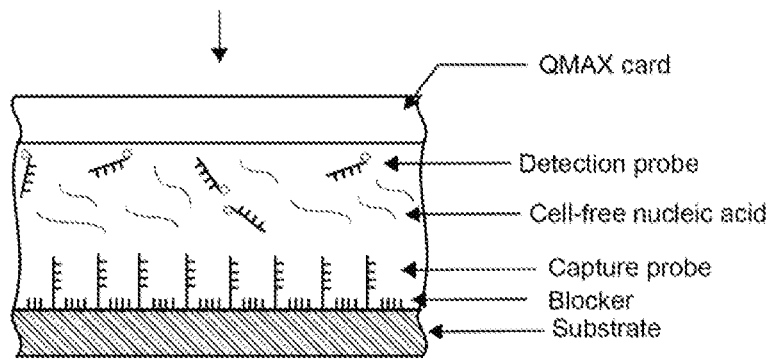
Figure 2:
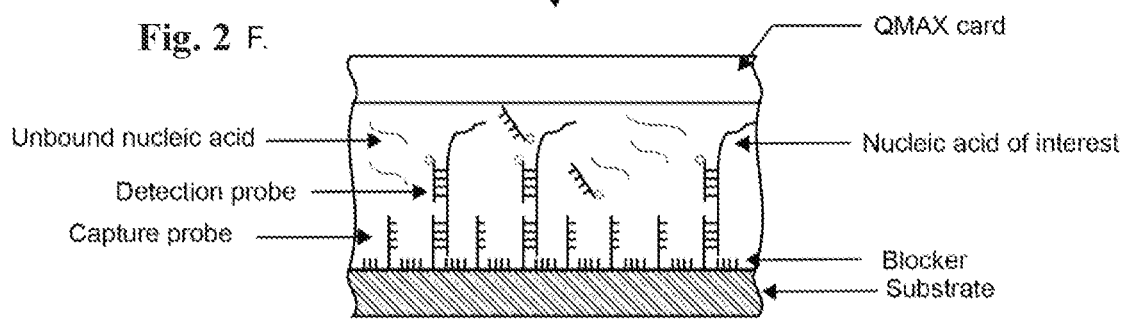
Figure 2:
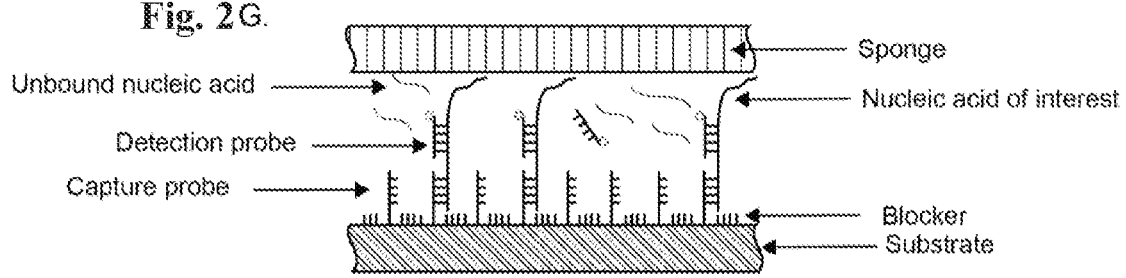
Figure 2:
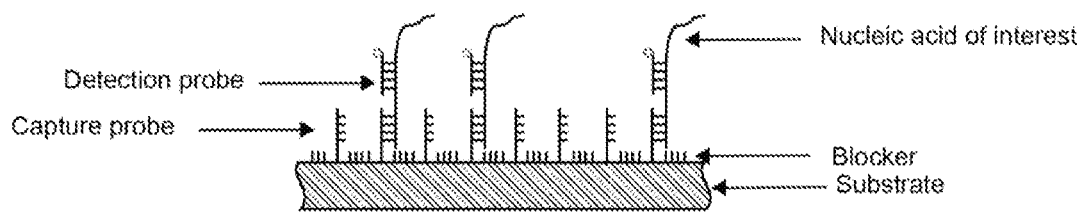

FIG. 2 is an illustration of an exemplary nucleic acid hybridization assay according to some embodiments of the present invention.

Brief Summary of Assay Process (A). Chip preparation: Capture probes were immobilized on the substrate surface;

(B). Chip blocking: chips were blocked with blockers.

(C). Sample introduction: Biological fluids (whole blood, plasma, serum, saliva, urine, sweat, etc.) containing targets of interest, in the form of either free nucleic acids or cell/particle contained nucleic acids, were added on the substrate surface;

(D) QMAX card closure and pressing: QMAX Card, with micro-scale structure side facing down, were placed on top of the chip and pressed. Necessary cell lysing reagents, protein denaturing reagents, hybridization reagents and labeled detection probe were dried on the side of QMAX Card with micro-scale structures;

(E)-(F). Cell or particle lysing, target sequence capture and detection: Dried reagents were dissolved in biological fluids. If necessary, cells (or particles) were lysed by lysing reagents to release target nucleic acid sequences. Released or free target nucleic acid sequences were then captured by immobilized capture probe on the substrate surface, and detected by labeled detection probe through hybridization;

(G). Wash: QMAX Card was peeled off and the substrate surface was washed with absorbing material containing suitable wash solution;

(H). Signal detection: signals from labeled detection probes were detected by detector.

Brief Experimental Procedures

As can be seen in FIG. 2(A), DNA oligonucleotide (capture probe) with specific sequence that is complemented to region of target nucleic acid sequence was coated on the surface of substrate. DNA oligonucleotide, termed as "capture probe (1)" is usually 10-50 bp in length, and 3' end modified to facilitate coating on the substrate. Commonly used 3' end modifications include but not limited to thiol, dithiol, amine, biotin, etc. Substrates can be used for capture probe immobilization include but not limited to gold surface, PMMA, PS, etc. Density of capture probe coated on the substrate is critical to the accessibility of the capture probe and thus affect the assay sensitivity. In one application, single type capture probe, specific to a single target nucleic acid sequence, can be immobilized on the substrate. In another application, different types of capture probes, specific to different target nucleic acid sequences or different regions of a single target nucleic acid sequence, can be immobilized on the substrate. Coating was ideally performed overnight at room temperature, but can be shortened. After coating, the uncoated capture probe was washed off using PBST buffer.

As can be seen in FIG. 2(B), the substrate surface was then blocked with blocker solutions. Suitable blockers include but not limited to small molecule blocks, such as 6-Mercapto-hexanol, or protein blockers, such as bovine serum albumin, casein, milk powder, etc. Blocking was performed for at least 30 min at room temperature. The substrate surface was then washed with PBST and ready to use.

As can be seen in FIG. 2(C), a biological sample is added onto the surface of capture probe coated substrate. Biological sample can be introduced by directly dropping on the substrate surface or facilitated by transferring tools. Biological samples that can be applied include but not limited to neat whole blood, plasma, serum, urine, saliva, sweat, etc. Target of interest can be in the form of free nucleic acid, nucleic acid and protein complex, or within human cell, animal cell, plant cell, bacteria cells, fungi cells, virus particles, etc. Target of interest includes but not limited to linear nucleic acid, circular nucleic acid, single strand nucleic acid, double strand nucleic acid, etc. [1] The term "nucleic acid" as used herein refers to any DNA or RNA molecule, or a DNA/RNA hybrid, or mixtures of DNA and/or RNA. The term "nucleic acid" therefore is intended to include but not limited to genomic or chromosomal DNA, plasmid DNA, amplified DNA, cDNA, total RNA, mRNA, miRNA, and small RNA. The term "nucleic acid" is also intended to include natural DNA and/or RNA molecule, or synthetic DNA and/or RNA molecule. In some embodiments, cell-free nucleic acids are presence in the sample, as used herein "cell-free" indicates nucleic acids are not contained in any cellular structures. In some other embodiments, nucleic acids are contained within cellular structures, which include but not limited to human cells, animal cells, plant cells, bacterial cells, fungi cells, and/or viral particles. Nucleic acids either in the form of cell-free nucleic acids or within cellular structures or a combination thereof, can be presence in the sample. In some further embodiments, nucleic acids are purified before introduced onto the inner surface of the first plate. In yet further embodiments, nucleic acids can be within a complex associated with other molecules, such as proteins and lipids.

As can be seen in FIG. 2(D), in some embodiments, necessary reagents, including but limited to cell lysing reagents, protein denaturing reagents, nucleic acid hybridization buffer, and labeled detection probes, etc, were spotted or directly dried on the side of X-plate (marked as QMAX card in some embodiments) with micro-scale structures. After sample introduction, X-plate with dried reagents (8) side facing down, was pressed on the sample and to the substrate.

In some embodiments, cell lysing reagents include but not limited to salts, detergents, enzymes, and other additives. The term "salts" herein include but not limited to lithium salt (e.g. lithium chloride), sodium salt (e.g. sodium chloride), potassium (e.g. potassium chloride), Tris, and HEPES. The term "detergents" herein can be ionic, including anionic and cationic, non-ionic or zwitterionic. The term "ionic detergent" as used herein includes any detergent which is partly or wholly in ionic form when dissolved in water. Suitable anionic detergents include but not limited to sodium dodecyl sulphate (SDS) or other alkali metal alkylsulphate salts or similar detergents, sarkosyl, or combinations thereof. The term "enzymes" herein include but not limited to lysozyme, cellulase, and proteinase. In addition, chelating agents including but not limited to EDTA, EGTA and other polyamino carboxylic acids, and some reducing agents, such as dithiotreitol (dTT), can also be included in cell lysing reagents.

As can be seen in FIG. 2(E), after X-plate was pressed on substrate, dried reagents were dissolved into biological fluids. Cell lysing reagents facilitate breaking cell wall and cell membranes to release the target nucleic acid analyte. Protein denaturing reagents, such as SDS, denature nucleic acid associated binding protein to release free nucleic acid. The composition of dried hybridization reagent is critical to provide suitable salt concentrations to maintain the strength of hybridization complex and also reduce non-specific binding from biological samples. For example, sodium chloride and sodium citrate were added to provide ideal ionic strength in the hybridization buffer. Ficoll and Polyvinylprolidine (PVP) can be added to accelerate the hybridization process. Bovine serum albumin is added to reduce interference from biological samples. Labeled detection probe with specific complementary sequence against target nucleic acid sequence is used to detect target nucleic acid sequence through hybridization.

As can be seen in FIG. (F), cell free target nucleic acid sequences and/or released the target nucleic acid analytes were captured by the capture probe through sequence specific hybridization. Meanwhile, captured target nucleic acid sequences were detected by labeled detection probe through sequence specific hybridization. X-plate can be pressed on the substrate for certain period of time. Experimental data indicated that after 2 min, captured target nucleic acid sequence reached equilibrium.

As can be seen in FIG. 2(g), X-plate was peeled off from the substrate. An absorbing material, such as sponge, containing suitable wash buffer, preferably 5×SSC and 0.05% Tween 20, was placed and softly pressed on the substrate surface. During wash, cell debris, proteins, non-specific nucleic acid, etc. were removed from the substrate surface.

In some embodiments, buffers with different ionic strengths may be applied to increase signal to contrast ratio. Examples include but not limited to, 0.1×SSC, 0.5×SSC, 1×SSC, 2×SSC, or 5×SSC. Washing step typically contain washing the plate of 1 time, 2 times, or 3 times, or more time. In some embodiments, each washing step may use the same type of washing buffer. In some embodiments, different washing buffer may be used in each washing step.

In some embodiments, 0.05% Tween 20 was used. In some embodiments, other detergents may be used. As used herein, the term "detergents" can be ionic, including anionic and cationic, non-ionic or zwitterionic. The term "ionic detergent" as used herein includes any detergent which is partly or wholly in ionic form when dissolved in water. Suitable anionic detergents include but not limited to sodium dodecyl sulphate (SDS) or other alkali metal alkylsulphate salts or similar detergents, sarkosyl, or combinations thereof.

As shown in FIG. 2(H), the absorbing material was peeled off from the substrate. The signal intensity yielded from labeled detection probe was measured by a suitable detector.

Examples for Nucleic Acid Hybridization Assays and Results

Example 1: miR21 Hybridization Assay in TE Buffer on M-Plate Detected by IR800 Labelled Detection Probe Using 96 Well Plate Assay details (referring to FIG. 3):
1 uM of thiolated capture probe was coated on gold M-plate surface at room temperature for overnight;
Rinsed with PBST for 3 times, and then blocked with 50 uM MCH for 30 min, and then rinsed with PBST for 3 times;
Add 50 ul of miR21 target (diluted in TE buffer) into each well, mixed with 50 ul of 1 uM IR800 labelled detection probe (diluted in H7140 hybridization buffer);
Hybridization for 2 h at room temperature;
Rinse M-plate with DNA washer (5×SSC+0.05% Tween 20) for 3 times;
Lump-sum signal measurement using Raman microscope.
Assay results (referring to FIG. 4):
Correlation between normalized signal intensities and the concentrations of miR21 target in TE buffer was observed.
Achieved a LoD of 510 fM miR21 target in TE buffer on M-plate using 2 h hybridization protocol
Achieved a dynamic range of 6 orders of magnitude.

Example 2: miR21 Hybridization Assay in 10% Plasma on M-Plate Detected by IR800 Labelled Detection Probe Using 96 Well Plate Assay details (referring to FIG. 5):
1 uM of thiolated capture probe was coated on gold M-plate surface at room temperature for overnight;
Rinsed with PBST for 3 times, and then blocked with 50 uM MCH for 30 min, and then rinsed with PBST for 3 times;
Add 50 ul of miR21 target (spiked in 10% plasma) into each well, mixed with 50 ul of 1 uM IR800 labelled detection probe (diluted in H7140 hybridization buffer);
Hybridization for 2 h at room temperature;
Rinse M-plate with DNA washer (5×SSC+0.05% Tween 20) for 3 times;
Lump-sum signal measurement using Raman microscope.
Assay results (referring to FIG. 6):
Correlation between normalized signal intensities and the concentrations of miR21 target in 10% plasma was observed.
Achieved a LoD of 820 fM miR21 target in 10% plasma on M-plate using 2 h hybridization protocol
Achieved a dynamic range of 6 orders of magnitude
Assay sensitivity in 10% plasma is similar with TE buffer, indicating non-significant interference in plasma matrix Example 3: miR21 Hybridization Assay in Neat Whole Blood on M-Plate Detected by IR800 Labelled Detection Probe Using 96 Well Plate Assay details (referring to FIG. 7):
1 uM of thiolated capture probe was coated on gold M-plate surface at room temperature for overnight;
Rinsed with PBST for 3 times, and then blocked with 50 uM MCH for 30 min, and then rinsed with PBST for 3 times;
Add 50 ul of miR21 target (spiked in neat whole blood) into each well, mixed with 50 ul of 1 uM IR800 labelled detection probe (diluted in H7140 hybridization buffer);
Hybridization for 2 h at room temperature;
Rinse M-plate with DNA washer (5×SSC+0.05% Tween 20) for 3 times;
Lump-sum signal measurement using Raman microscope.
Assay results (referring to FIG. 8):
Correlation between normalized signal intensities and the concentrations of miR21 target in neat whole blood was observed.
Achieved a LoD of 9.7 pM miR21 target in neat whole blood on M-plate using 2 h hybridization protocol
Achieved a dynamic range of 6 orders of magnitude
Assay sensitivity in neat whole blood is comparable with TE buffer and 10% plasma, indicating robust assay performance in the matrix of whole blood Example 4: Time Course Study—miR21 Hybridization Assay in Neat Whole Blood on Gold Thin Film Detected by IR800 Labelled Detection Probe Using QMAX Card with 30 Um Spacers Assay details (referring to FIG. 9):
1 uM of thiolated capture probe was coated on gold thin film at room temperature for overnight;
Rinsed with PBST for 3 times, and then blocked with 50 uM MCH for 30 min, and then rinsed with PBST for 3 times;
Drop 0.5 ul of 1 uM miR21 target (diluted in neat whole blood) on chip surface, mixed with 0.5 ul of 1 uM IR800 labelled detection probe (diluted in H7140 hybridization buffer);
Pressed with QMAX card with 30 um spacers, and hybridization for varied time at room temperature;
Rinse chip surface with DNA washer (5×SSC+0.05% Tween 20) for 3 times;
Lump-sum signal measurement using Raman microscope.
Assay results (referring to FIG. 10):
When using IR800 labelled detection probe in the miR21 hybridization assay, and pressed by QMAX card with 30 um spacers, signal intensity is higher at 2 min hybridization time compared to 1 min hybridization time.
After 2 min, signal intensity saturates
Thus, hybridization time of 2 min is used for further nucleic acid hybridization assay involved using IR800 labelled detection probe and QMAX card with 30 um spacers.

Example 5: Time Course Study—miR21 Hybridization Assay in Neat Whole Blood on Gold Thin Film Detected by Streptavidin-40 nm Bead Using QMAX Card with 30 Um Spacers Assay details (referring to FIG. 11):
1 uM of thiolated capture probe was coated on gold thin film at room temperature for overnight;
Rinsed with PBST for 3 times, and then blocked with 50 uM MCH for 30 min, and then rinsed with PBST for 3 times;

Drop 0.5 ul of miR21 target (diluted in TE buffer) on chip surface, mixed with 0.5 ul of 1 uM biotinylated detection probe (diluted in H7140 hybridization buffer);
Pressed with QMAX card with 30 um spacers, and hybridization for 2 min at room temperature;
Rinse chip surface with DNA washer (5×SSC+0.05% Tween 20) for 3 times;
Drop 1 ul of streptavidin-40 nm bead (1:10 diluted in 4% BSA).
Pressed with QMAX card with 30 um spacers and wait for varied time at room temperature;
Rinse chip surface with DNA washer for 3 times;
Lump-sum signal measurement using Raman microscope
Assay results (referring to FIG. 12):
When using IR800 labelled detection probe in the miR21 hybridization assay, and pressed by QMAX card with 30 um spacers, signal intensity is higher at 2 min hybridization time compared to 1 min hybridization time.
Signal intensity peaked at 5 min
Thus, hybridization time of 5 min is used for further nucleic acid hybridization assay involved using streptavidin-40 nm bead and QMAX card with 30 um spacers.

Figure 21:
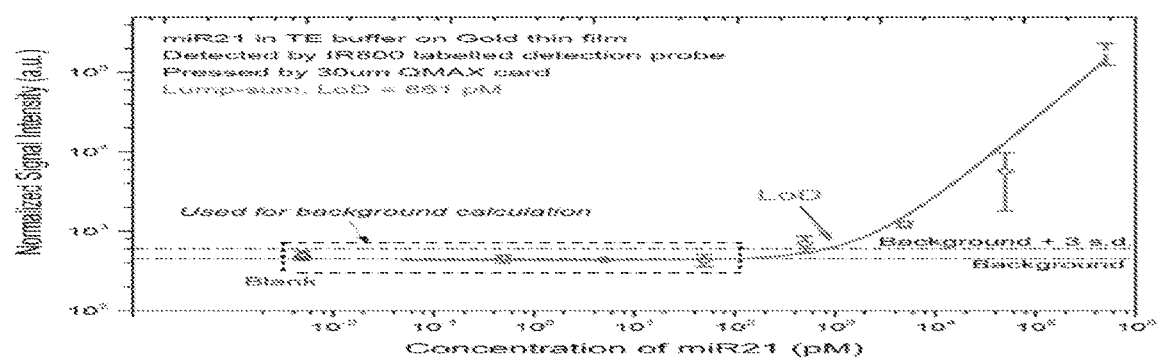
FIG. 21(A)-FIG. 21(D) shows an exemplary assay scheme of a nucleic acid hybridization assay of the present invention.
Figure 22:
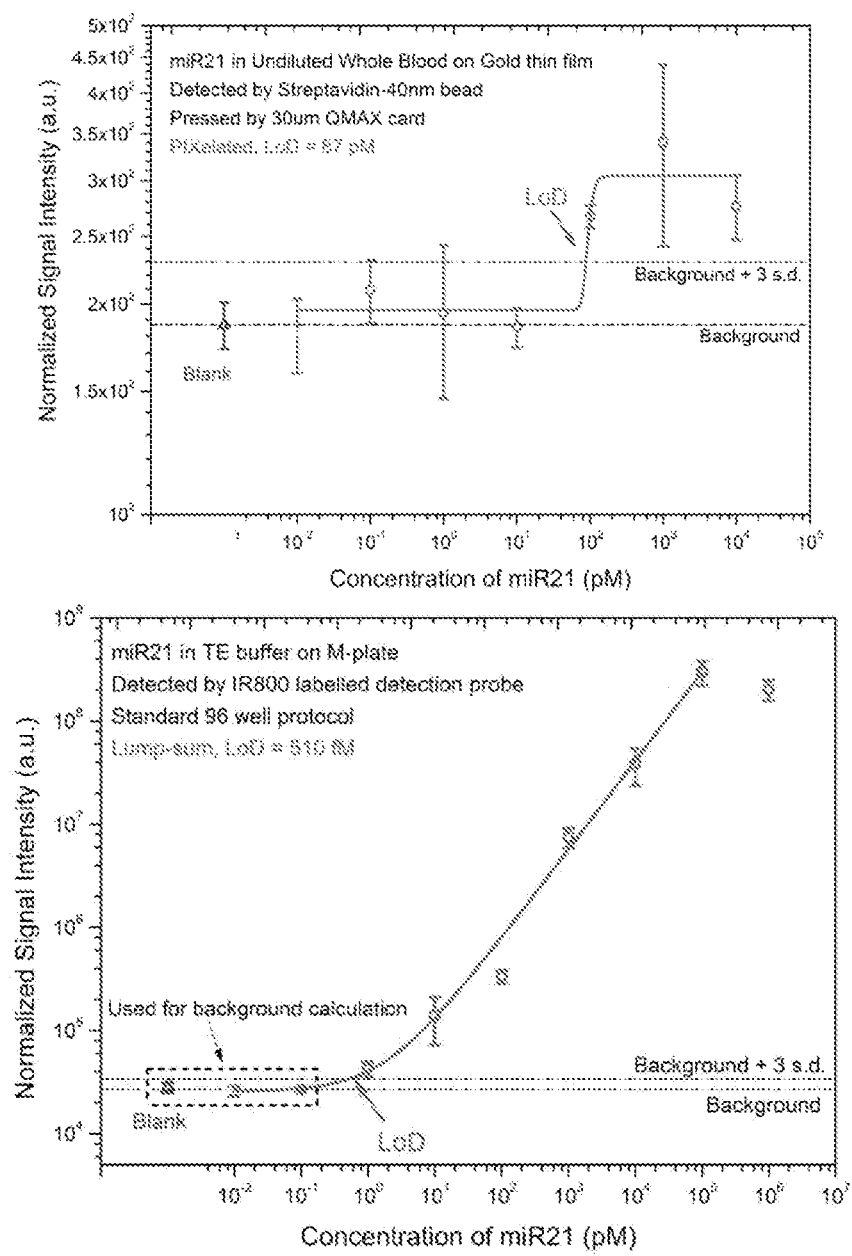
FIG. 22 shows the results of a nucleic acid hybridization assay based on the scheme as shown in FIG. 21(A)-FIG. 21(D).

Example 6: miR21 Hybridization Assay in TE Buffer on Gold Thin Film Detected by IR800 Labelled Detection Probe Using QMAX Card with 30 Um Spacers Assay details (referring to FIG. 13):
1 uM of thiolated capture probe was coated on gold thin film at room temperature for overnight;
Rinsed with PBST for 3 times, and then blocked with 50 uM MCH for 30 min, and then rinsed with PBST for 3 times;
Drop 0.5 ul of miR21 target (diluted in TE buffer) on chip surface, mixed with 0.5 ul of 1 uM IR800 labelled detection probe (diluted in H7140 hybridization buffer);
Pressed with QMAX card with 30 um spacers, and hybridization for 2 min at room temperature;
Rinse chip surface with DNA washer (5×SSC+0.05% Tween 20) for 3 times;
Lump-sum signal measurement using Raman microscope.
Assay results (referring to FIG. 14):
Correlation between normalized signal intensities and the concentrations of miR21 target in TE buffer was observed.
Achieved a LoD of 861 pM miR21 target in TE buffer using QMAX card with 30 um spacers under 2 min hybridization
Achieved a dynamic range of 3 orders of magnitude Example 7: miR21 Hybridization Assay in TE Buffer on Gold Thin Film Detected by Biotinylated Detection Probe and Streptavidin-40 nm Bead Using QMAX Card with 30 Um Spacers Assay details (referring to FIG. 15):
1 uM of thiolated capture probe was coated on gold thin film at room temperature for overnight;
Rinsed with PBST for 3 times, and then blocked with 50 uM MCH for 30 min, and then rinsed with PBST for 3 times;
Drop 0.5 ul of miR21 target (diluted in TE buffer) on chip surface, mixed with 0.5 ul of 1 uM biotinylated detection probe (diluted in H7140 hybridization buffer);
Pressed with QMAX card with 30 um spacers, and hybridization for 2 min at room temperature;
Rinse chip surface with DNA washer (5×SSC+0.05% Tween 20) for 3 times;
Drop 1 ul of streptavidin-40 nm bead (1:10 diluted in 4% BSA).
Pressed with QMAX card with 30 um spacers and wait for 5 min at room temperature;
Rinse chip surface with DNA washer for 3 times;
Lump-sum signal measurement using Raman microscope.
Assay results (referring to FIG. 16):
Correlation between normalized signal intensities and the concentrations of miR21 target in TE buffer was observed.
Achieved a LoD of 28 nM miR21 target in TE buffer using QMAX card with 30 um spacers under 2 min hybridization
Achieved a dynamic range of 1 orders of magnitude Example 8: miR21 Hybridization Assay in Neat Whole Blood on Gold Thin Film Detected by IR800 Labelled Detection Probe Using QMAX Card with 30 Um Spacers Assay details (referring to FIG. 17):
1 uM of thiolated capture probe was coated on gold thin film at room temperature for overnight;
Rinsed with PBST for 3 times, and then blocked with 50 uM MCH for 30 min, and then rinsed with PBST for 3 times;
Drop 0.5 ul of miR21 target (diluted in neat whole blood) on chip surface, mixed with 0.5 ul of 1 uM IR800 labelled detection probe (diluted in H7140 hybridization buffer);
Pressed with QMAX card with 30 um spacers, and hybridization for 2 min at room temperature;
Rinse chip surface with DNA washer (5×SSC+0.05% Tween 20) for 3 times;
Lump-sum signal measurement using Raman microscope.
Assay results (referring to FIG. 18):
Correlation between normalized signal intensities and the concentrations of miR21 target in neat whole blood was observed.
Achieved a LoD of 8.41 pM miR21 target in neat whole blood using QMAX card with 30 um spacers under 2 min hybridization
Achieved a dynamic range of 5 orders of magnitude
Using QMAX card significantly shorten the assay time (from 2 h to 2 min) with almost the same sensitivity (9.7 pM compared to 8.41 pM) on gold thin film Example 9: miR21 Hybridization Assay in Neat Whole Blood on Gold Thin Film Detected by Biotinylated Detection Probe and Streptavidin-40 nm Bead Using QMAX Card with 30 Um Spacers Assay details (referring to FIG. 19):
1 uM of thiolated capture probe was coated on gold thin film at room temperature for overnight;
Rinsed with PBST for 3 times, and then blocked with 50 uM MCH for 30 min, and then rinsed with PBST for 3 times;
Drop 0.5 ul of miR21 target (diluted in neat whole blood) on chip surface, mixed with 0.5 ul of 1 uM biotinylated detection probe (diluted in H7140 hybridization buffer);

Pressed with QMAX card with 30 um spacers, and hybridization for 2 min at room temperature;
Rinse chip surface with DNA washer (5×SSC+0.05% Tween 20) for 3 times;
Drop 1 ul of streptavidin-40 nm bead (1:10 diluted in 4% BSA).
Pressed with QMAX card with 30 um spacers and wait for 5 min at room temperature;
Rinse chip surface with DNA washer for 3 times;
Lump-sum signal measurement using Raman microscope.
Assay results (referring to FIG. 20):
Correlation between normalized signal intensities and the concentrations of miR21 target in neat whole blood was observed.
Achieved a LoD of 8.8 nM miR21 target in neat whole blood using 2 min hybridization protocol
Achieved a dynamic range of 2 orders of magnitude Example 10: miR21 Hybridization Assay in Neat Whole Blood on Gold Thin Film Detected by Biotinvlated Detection Probe and Streptavidin-40 nm Bead Using QMAX Card with 30 Um Spacers Assay details (referring to FIG. 21):
1 uM of thiolated capture probe was coated on gold thin film at room temperature for overnight;
Rinsed with PBST for 3 times, and then blocked with 50 uM MCH for 30 min, and then rinsed with PBST for 3 times;
Drop 0.5 ul of miR21 target (diluted in neat whole blood) on chip surface, mixed with 0.5 ul of 1 uM biotinylated detection probe (diluted in H7140 hybridization buffer);
Pressed with QMAX card with 30 um spacers, and hybridization for 2 min at room temperature;
Rinse chip surface with DNA washer (5×SSC+0.05% Tween 20) for 3 times;
Drop 1 ul of streptavidin-40 nm bead (1:10 diluted in 4% BSA).
Pressed with QMAX card with 30 um spacers and wait for 5 min at room temperature;
Rinse chip surface with DNA washer for 3 times;
PIXelated measurement using inverted microscope.
Assay results (referring to FIG. 22)
Correlation between normalized signal intensities and the concentrations of miR21 target in neat whole blood was observed.
Achieved a LoD of 87 pM miR21 target in neat whole blood using QMAX card with 30 um spacers under 2 min hybridization
Achieved a dynamic range of 2 orders of magnitude Example 11: miR21 Hybridization Assay in Neat Whole Blood on Gold Thin Film Detected by Biotinylated Detection Probe and Streptavidin-Cv5 Using QMAX Card with 30 Um Spacers Assay details (referring to FIG. 23):
1 uM of thiolated capture probe was coated on gold thin film at room temperature for overnight;
Rinsed with PBST for 3 times, and then blocked with 50 uM MCH for 30 min, and then rinsed with PBST for 3 times;
Drop 0.5 ul of miR21 target (diluted in neat whole blood) on chip surface, mixed with 0.5 ul of 1 uM biotinylated detection probe (diluted in H7140 hybridization buffer);
Pressed with QMAX card with 30 um spacers, and hybridization for 2 min at room temperature;
Rinse chip surface with DNA washer (5×SSC+0.05% Tween 20) for 3 times;
Drop 1 ul of 500 ng/ml streptavidin-Cy5.
Pressed with QMAX card with 30 um spacers and wait for 2 min at room temperature;
Rinse chip surface with DNA washer for 3 times;
Lump-sum signal measurement using Raman microscope.
Assay results (referring to FIG. 24)
Correlation between normalized signal intensities and the concentrations of miR21 target in neat whole blood was observed.
Achieved a LoD of 68 pM miR21 target in neat whole blood using QMAX card with 30 um spacers under 2 min hybridization
Achieved a dynamic range of 4 orders of magnitude
Assay sensitivity using Streptavidin-Cy5 as detection label (68 pM) is not as good as using IR800 as the label (8.41 pM).

Example 12: miR21 Hybridization Assay in Neat Whole Blood on M-Plate Detected by IR800 Labelled Detection Probe Using QMAX Card with 30 Um Spacers Assay details (referring to FIG. 25):
1 uM of thiolated capture probe was coated on M-plate at room temperature for overnight;
Rinsed with PBST for 3 times, and then blocked with 50 uM MCH for 30 min, and then rinsed with PBST for 3 times;
Drop 0.5 ul of miR21 target (diluted in neat whole blood) on chip surface, mixed with 0.5 ul of 1 uM IR800 labelled detection probe (diluted in H7140 hybridization buffer);
Pressed with QMAX card with 30 um spacers, and hybridization for 2 min at room temperature;
Rinse M-plate with DNA washer (5×SSC+0.05% Tween 20) for 3 times;
Lump-sum signal measurement using Raman microscope.
Assay results (referring to FIG. 26)
Correlation between normalized signal intensities and the concentrations of miR21 target in neat whole blood was observed.
Achieved a LoD of 10 pM miR21 target in neat whole blood using QMAX card with 30 um spacers under 2 min hybridization
Achieved a dynamic range of 5 orders of magnitude
Again, using QMAX card significantly shorten the assay time (from 2 h to 2 min) with almost the same sensitivity (10 pM compared to 8.41 pM) on gold thin film
However, using M-plate did not improve the assay sensitivity probably due to the poor quality of M-plate.

Example 13: miR21 Hybridization Assay in Neat Whole Blood on M-Plate Detected by IR800 Labelled Detection Probe Using QMAX Card with 30 Um Spacers Assay details (referring to FIG. 27):
1 uM of thiolated capture probe was coated on M-plate at room temperature for overnight;
Rinsed with PBST for 3 times, and then blocked with 50 uM MCH for 30 min, and then rinsed with PBST for 3 times;

Drop 0.5 ul of miR21 target (diluted in neat whole blood) on chip surface, mixed with 0.5 ul of 1 uM IR800 labelled detection probe (diluted in H7140 hybridization buffer);
Pressed with QMAX card with 30 um spacers, and hybridization for 2 min at room temperature;
Rinse M-plate with DNA washer (5×SSC+0.05% Tween 20) for 3 times;
PIXelated measurement using inverted microscope.
Assay results (referring to FIG. 28)
Correlation between normalized signal intensities and the concentrations of miR21 target in neat whole blood was observed
Achieved a LoD of 350 fM miR21 target in neat whole blood using QMAX card with 30 um spacers under 2 min hybridization using PIXelated measurement method
When measured by PIXelated method (350 fM), which is approximately 2 orders more sensitive than Lump-sum measurement method (10 pM) of the same assay Example 14: miR21 Hybridization Assay in Neat Whole Blood on 30 Um X-Well Detected by IR800 Labelled Detection Probe Assay details (referring to FIG. 29):
1 uM of thiolated capture probe was coated on X-Well at room temperature for overnight;
Rinsed with PBST for 3 times, and then blocked with 50 uM MCH for 30 min, and then rinsed with PBST for 3 times;
Drop 0.5 ul of miR21 target (diluted in neat whole blood) on chip surface, mixed with 0.5 ul of 1 uM IR800 labelled detection probe (diluted in H7140 hybridization buffer);
Pressed with PET film, and hybridization for 2 min at room temperature;
Rinse X-Well with DNA washer (5×SSC+0.05% Tween 20) for 3 times;
Lump-sum signal measurement using Raman microscope.
Assay results (referring to FIG. 30)
Correlation between normalized signal intensities and the concentrations of miR21 target in neat whole blood was observed
Achieved a LoD of 140 fM miR21 target in neat whole blood using QMAX card with 30 um spacers under 2 min hybridization
Pressing with PET film slightly improved the LoD (pressing LoD=140 pM v.s. without pressing LoD=336 pM)

Figures 33, 34:
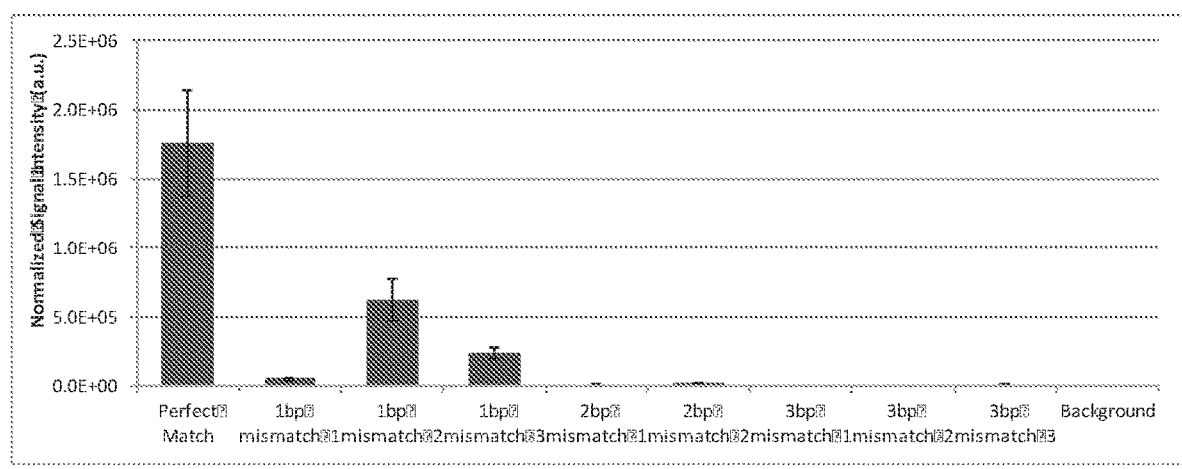
FIG. 33 shows the signal intensities and changes based on the design of FIG. 32 and assay of FIG. 31(A)-FIG. 31(C).
FIG. 34 shows the results of a nucleic acid hybridization assay based on the scheme as shown in FIG. 31(A)-FIG. 31(C).

Example 15: Single Base Pair Differentiation in miR21 Hybridization Assay in Neat Whole Blood on M-Plate Detected by IR800 Labelled Detection Probe Using 96 Well Plate Assay details (referring to FIGS. 31 and 32):
500 nM of thiolated capture probe was coated on gold M-plate surface at room temperature for overnight;
Rinsed with PBST for 3 times, and then blocked with 50 uM MCH for 30 min, and then rinsed with PBST for 3 times;
Add 50 ul of 10 nM miR21 target (diluted in neat whole blood) into each well, mixed with 50 ul of 100 nM IR800 labelled detection probe (diluted in H7140 hybridization buffer);
Hybridization for 2 h at room temperature;
Rinse M-plate with DNA washer (1×SSC+0.05% Tween 20) for 3 times;
Lump-sum signal measurement using Raman microscope.
Assay results (referring to FIGS. 33 and 34)
Perfectly matched miR21 target yielded the highest signal intensity among all tested mismatched targets
Impact of the mismatch base pair on the signal intensity is location dependent.
Mismatch base pair locates at the center of the hybridization region has more significant impact than those at the end of the hybridization region
Even only introducing a single mismatched base pair at the end of hybridization region, it resulted in approximately 3 fold decrease of signal intensity
Summary of Experiment Conditions

| Example | Sample | Method | Substrate Plate | Volume | Label | Measurement | LoD |
|---|---|---|---|---|---|---|---|
| 1 | TE | 96 well | M-Plate | 100 ul | IR800 | Lumpsum | 510 nM |
| 2 | 10% Plasma | 96 well | M-Plate | 100 ul | IR800 | Lumpsum | 820 fM |
| 3 | Whole Blood | 96 well | M-Plate | 100 ul | IR800 | Lumpsum | 9.7 pM |
| 4 | Whole Blood | 96 well | M-Plate | 100 ul | IR800 | Lumpsum | |
| 5 | Whole Blood | 96 well | M-Plate | 100 ul | IR800 | Lumpsum | |
| 6 | TE | X-plate | Gold thin film | 1 ul | IR800 | Lumpsum | 861 pM |
| 7 | TE | X-plate | Gold thin film | 1 ul | 40 nm beads | Lumpsum | 28 nM |
| 8 | Whole Blood | X-plate | Gold thin film | 1 ul | IR800 | Lumpsum | 8.41 pM |
| 9 | Whole Blood | X-plate | Gold thin film | 1 ul | 40n m beads | Lumpsum | 8.8 nM |
| 10 | Whole Blood | X-plate | Gold thin film | 1 ul | 40 nm beads | Pixelated | 87 pM |
| 11 | Whole Blood | X-plate | Gold thin film | 1 ul | Cy5 | Lumpsum | 68 pM |
| 12 | Whole Blood | X-well | M-Plate | 1 ul | IR800 | Lumpsum | 10 pM |
| 13 | Whole Blood | X-plate | M-Plate | 1 ul | IR800 | Pixelated | 350 fM |
| 14 | Whole Blood | X-well | — | 1.5 ul | IR800 | Lumpsum | 140 pM |

-continued

| Example | Sample | Method | Substrate Plate | Volume | Label | Measurement | LoD |
|---------|--------|--------|-----------------|--------|-------|-------------|-----|
| 15 | Whole Blood | X-well | | 1.5 ul | IR800 | Lumpsum | |

In all experiments, the analyte is miR21 nucleic acid.

Examples of Present Invention

A1. A device for a nucleic acid hybridization assay, comprising:
   a first plate, a second plate, and spacers, wherein:
   i. the plates are movable relative to each other into different configurations;
   ii. each plate respectively comprises an inner surface that has a sample contact area for contacting a sample that comprises a nucleic acid analyte,
   iii. the spacers have a predetermined substantially uniform height,
   iv. the first plate comprises a nucleic acid capture probe that is coated on the inner surface of the first plate, and
   v. the second plate comprises a nucleic acid detection probe that is coated on the inner surface of the second plate;
      wherein one of the configurations is an open configuration, in which: the two plates are partially or entirely separated apart, the spacing between the plates is not regulated by the spacers, and the sample is deposited on one or both of the plates;
      wherein another of the configurations is a closed configuration, which is configured after the sample deposition in the open configuration, and in the closed configuration: at least one spacer is between the two plates, at least part of the sample deposited is compressed by the plates into a layer of highly uniform thickness and is substantially stagnant relative to the plates, wherein the uniform thickness of the layer is confined by the inner surfaces of the two plates and is regulated by the plates and the spacers;
      wherein the capture probe is configured to bind complimentarily to one part of the analyte and immobilize the analyte to the inner surface of the first plate; and
      wherein the detection probe is configured to diffuse into layer of uniform thickness and bind complimentarily to another part the analyte to produce a detectable signal.

B1. A method of nucleic acid analysis, comprising:
   (a) obtaining a liquid sample comprising a nucleic acid analyte;
   (b) obtaining a device of any of paragraphs A1-A12; wherein:
   (c) depositing the sample on one or both of the plates when the plates are in an open configuration,
   (d) after (c), bringing the two plates together and pressing the plates into a closed configuration,
   (e) detecting and measuring the signal from the layer of uniform thickness, thereby determining the presence and/or amount of the nucleic acid analyte.

A2. The device of embodiment A1, wherein the first plate further comprises blockers that are coated on the inner surface of the first plate.

A3. The device of any prior embodiments, wherein the first plate and/or the second plate further comprise stabilizers that are coated on the inner surface of the respective plate.

A4. The device of embodiment A3, wherein the stabilizer is selected from: sugar, polymers, glycerol, and a mixture thereof.

A5. The device of embodiment A3, wherein the stabilizer is sucrose or glucose.

A6. The device of any prior embodiments, wherein the capture probe is covalently bound to the inner surface of the first plate.

A7. The device of any prior embodiments, wherein the capture probe is bound to the inner surface of the first plate through a thiol bond.

A8. The device of embodiment A7, wherein the attachment reagent is protein A.

A9. The device of any prior embodiments, wherein the sample comprises whole blood.

A10. The device of any prior embodiments, wherein the sample comprises blood serum.

A11. The device of any prior embodiments, wherein the spacers are fixed on the inner surface of the second plate.

A12. The device of any prior embodiments, wherein the detection probe and/or the capture probe have the length of 10-40 bp.

B2. The method of embodiment B1, wherein the first plate further comprises blockers that are coated on the inner surface of the first plate.

B3. The method of any prior embodiments, wherein the first plate and/or the second plate further comprise stabilizers that are coated on the inner surface of the respective plate.

B4. The method of embodiment B3, wherein the stabilizer is selected from: sugar, polymers, glycerol, and a mixture thereof.

B5. The method of embodiment B3, wherein the stabilizer is sucrose or glucose.

B6. The method of any prior embodiments, wherein the capture probe is covalently bound to the inner surface of the first plate.

B7. The method of any prior embodiments, wherein the capture probe is attached to the inner surface of the first plate by passive absorption through hydrophobic interactions between inner surface and non-polar residues on an attachment reagent that bound to the capture probe.

B8. The method of embodiment B7, wherein the attachment reagent is protein A.

B8. The method of any prior embodiments, wherein the sample comprises whole blood.

B9. The method of any prior embodiments, wherein the sample comprises blood plasma.

B10. The method of any prior embodiments, wherein the spacers are fixed on the inner surface of the second plate.

B11. The method of any prior embodiments, before step (e) and after step (d), further comprising incubating the layer of uniform thickness for a predetermined period of time.

B12. The method of embodiment B11, wherein the predetermined period of time is equal to or longer than the time needed for the detection probe to diffuse into the sample across the layer of uniform thickness.

B13. The method of any prior embodiments, wherein the sample is deposited on the first plate.

B14. The method of any prior embodiments, before step (d) after step (c), further comprising incubating the sample on the first plate for a predetermined period of time.

B15. The method of embodiment B14, wherein the predetermined period of time is equal to or longer than the time needed for the binding between the capture probe and the analyte to reach an equilibrium.

B16. The method of any prior embodiments, before step (d) and after step (c), further comprising washing the inner surface of the first plate.

B17. The method of any prior embodiments, before step (e) and after step (d), further comprising switching the plates into the open configuration and washing the inner surface of the first plate.

B18. The method of any prior embodiments, wherein the inner surface of the first plate is washed with a washing solution absorbed in a sponge.

B19. The method of any prior embodiments, wherein the washing is conducted by squeezing the sponge to release the wash solution onto the inner surface of the first plate and releasing the sponge to reabsorb the wash solution.

B20. The method of any prior embodiments, wherein the washing improves the limit of detection (LOD) for the detectable signal.

Related Documents

The present invention includes a variety of embodiments, which can be combined in multiple ways as long as the various components do not contradict one another. The embodiments should be regarded as a single invention file: each filing has other filing as the references and is also referenced in its entirety and for all purpose, rather than as a discrete independent. These embodiments include not only the disclosures in the current file, but also the documents that are herein referenced, incorporated, or to which priority is claimed.

(1) Definitions

The terms used in describing the devices, systems, and methods herein disclosed are defined in the current application, or in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/426,065, which was filed on Feb. 8, 2017, U.S. Provisional Application No. 62/456,504, which was filed on Feb. 8, 2017, all of which applications are incorporated herein in their entireties for all purposes.

The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF card) that regulate the spacing between the plates. The term "X-plate" refers to one of the two plates in a CROF card, wherein the spacers are fixed to this plate. More descriptions of the COF Card, CROF Card, and X-plate are given in the provisional application Ser. No. 62/456,065, filed on Feb. 7, 2017, which is incorporated herein in its entirety for all purposes.

(2) Q-Card, Spacer and Uniform Sample Thickness

The devices, systems, and methods herein disclosed can include or use Q-cards, spacers, and uniform sample thickness embodiments for sample detection, analysis, and quantification. In some embodiments, the Q-card comprises spacers, which help to render at least part of the sample into a layer of high uniformity. The structure, material, function, variation and dimension of the spacers, as well as the uniformity of the spacers and the sample layer, are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/426,065, which was filed on Feb. 8, 2017, U.S. Provisional Application No. 62/456,504, which was filed on Feb. 8, 2017, all of which applications are incorporated herein in their entireties for all purposes.

(3) Hinges, Opening Notches, Recessed Edge and Sliders

The devices, systems, and methods herein disclosed can include or use Q-cards for sample detection, analysis, and quantification. In some embodiments, the Q-card comprises hinges, notches, recesses, and sliders, which help to facilitate the manipulation of the Q card and the measurement of the samples. The structure, material, function, variation and dimension of the hinges, notches, recesses, and sliders are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/426,065, which was filed on Feb. 8, 2017, U.S. Provisional Application No. 62/456,504, which was filed on Feb. 8, 2017, all of which applications are incorporated herein in their entireties for all purposes.

(4) Q-Card, Sliders, and Smartphone Detection System

The devices, systems, and methods herein disclosed can include or use Q-cards for sample detection, analysis, and quantification. In some embodiments, the Q-cards are used together with sliders that allow the card to be read by a smartphone detection system. The structure, material, function, variation, dimension and connection of the Q-card, the sliders, and the smartphone detection system are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/426,065, which was filed on Feb. 8, 2017, U.S. Provisional Application No. 62/456,504, which was filed on Feb. 8, 2017, all of which applications are incorporated herein in their entireties for all purposes.

(5) Detection Methods

The devices, systems, and methods herein disclosed can include or be used in various types of detection methods.

The detection methods are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/426,065, which was filed on Feb. 8, 2017, U.S. Provisional Application No. 62/456,504, which was filed on Feb. 8, 2017, all of which applications are incorporated herein in their entireties for all purposes.

(6) Labels

The devices, systems, and methods herein disclosed can employ various types of labels that are used for analytes detection. The labels are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/426,065, which was filed on Feb. 8, 2017, U.S. Provisional Application No. 62/456,504, which was filed on Feb. 8, 2017, all of which applications are incorporated herein in their entireties for all purposes.

(7) Analytes

The devices, systems, and methods herein disclosed can be applied to manipulation and detection of various types of analytes (including biomarkers). The analytes and are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/426,065, which was filed on Feb. 8, 2017, US Provisional Application No. 62/456,504, which was filed on Feb. 8, 2017, all of which applications are incorporated herein in their entireties for all purposes.

(8) Applications (Field and Samples)

The devices, systems, and methods herein disclosed can be used for various applications (fields and samples). The applications are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/426,065, which was filed on Feb. 8, 2017, U.S. Provisional Application No. 62/456,504, which was filed on Feb. 8, 2017, all of which applications are incorporated herein in their entireties for all purposes.

(9) Cloud

The devices, systems, and methods herein disclosed can employ cloud technology for data transfer, storage, and/or analysis. The related cloud technologies are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, US Provisional Application No. 62/456,065, which was filed on Feb. 7, 2017, U.S. Provisional Application No. 62/426,065, which was filed on Feb. 8, 2017, U.S. Provisional Application No. 62/456,504, which was filed on Feb. 8, 2017, all of which applications are incorporated herein in their entireties for all purposes.

Flat Top of Pillar Spacers

In certain embodiments of the present invention, the spacers are pillars that have a flat top and a foot fixed on one plate, wherein the flat top has a smoothness with a small surface variation, and the variation is less than 5, 10 nm, 20 nm, 30 nm, 50 nm, 100 nm, 200 nm, 300 nm, 400 nm, 500 nm, 600 nm, 700 nm, 800 nm, 1000 nm, or in a range between any two of the values. A preferred flat pillar top smoothness is that surface variation of 50 nm or less.

Furthermore, the surface variation is relative to the spacer height and the ratio of the pillar flat top surface variation to the spacer height is less than 0.5%, 1%, 3%, 5%, 7%, 10%, 15%, 20%, 30%, 40%, or in a range between any two of the values. A preferred flat pillar top smoothness has a ratio of the pillar flat top surface variation to the spacer height is less than 2%, 5%, or 10%.

Sidewall Angle of Pillar Spacers

In certain embodiments of the present invention, the spacers are pillars that have a sidewall angle. In some embodiments, the sidewall angle is less than 5 degree (measured from the normal of a surface), 10 degree, 20 degree, 30 degree, 40 degree, 50 degree, 70 degree, or in a range between any two of the values. In a preferred embodiment, the sidewall angle is less 5 degree, 10 degree, or 20 degree.

Formation of Uniform Thin Fluidic Layer by an Imprecise Force Pressing

In certain embodiment of the present invention, a uniform thin fluidic sample layer is formed by using a pressing with an imprecise force. The term "imprecise pressing force" without adding the details and then adding a definition for imprecise pressing force. As used herein, the term "imprecise" in the context of a force (e.g. "imprecise pressing force") refers to a force that (a) has a magnitude that is not precisely known or precisely predictable at the time the force is applied; (b) has a pressure in the range of 0.01 kg/cm$^2$ (centimeter square) to 100 kg/cm$^2$, (c) varies in magnitude from one application of the force to the next; and (d) the imprecision (i.e. the variation) of the force in (a) and (c) is at least 20% of the total force that actually is applied.

An imprecise force can be applied by human hand, for example, e.g., by pinching an object together between a thumb and index finger, or by pinching and rubbing an object together between a thumb and index finger.

In some embodiments, the imprecise force by the hand pressing has a pressure of 0.01 kg/cm2, 0.1 kg/cm2, 0.5 kg/cm2, 1 kg/cm2, 2 kg/cm2, kg/cm2, 5 kg/cm2, 10 kg/cm2, 20 kg/cm2, 30 kg/cm2, 40 kg/cm2, 50 kg/cm2, 60 kg/cm2, 100 kg/cm2, 150 kg/cm2, 200 kg/cm2, or a range between any two of the values; and a preferred range of 0.1 kg/cm2 to 0.5 kg/cm2, 0.5 kg/cm2 to 1 kg/cm2, 1 kg/cm2 to 5 kg/cm2, 5 kg/cm2 to 10 kg/cm2 (Pressure).

Spacer Filling Factor.

The term "spacer filling factor" or "filling factor" refers to the ratio of the spacer contact area to the total plate area", wherein the spacer contact area refers, at a closed configuration, the contact area that the spacer's top surface contacts to the inner surface of a plate, and the total plate area refers the total area of the inner surface of the plate that the flat top of the spacers contact. Since there are two plates and each spacer has two contact surfaces each contacting one plate, the filling fact is the filling factor of the smallest.

For example, if the spacers are pillars with a flat top of a square shape (10 um×10 um), a nearly uniform cross-section and 2 um tall, and the spacers are periodic with a period of 100 um, then the filing factor of the spacer is 1%. If in the above example, the foot of the pillar spacer is a square shape of 15 um×15 um, then the filling factor is still 1% by the definition.

The method or device of any prior embodiment, wherein the spacers have pillar shape and nearly uniform cross-section.

The method or device of any prior embodiment, wherein the inter spacer distance (SD) is equal or less than about 120 um (micrometer).

The method or device of any prior embodiment, wherein the inter spacer distance (SD) is equal or less than about 100 um (micrometer).

The method or device of any prior embodiment, wherein the fourth power of the inter-spacer-distance (ISD) divided by the thickness (h) and the Young's modulus (E) of the flexible plate (ISD4/(hE)) is 5×106 um3/GPa or less.

The method or device of any prior embodiment, wherein the fourth power of the inter-spacer-distance (ISD) divided by the thickness (h) and the Young's modulus (E) of the flexible plate (ISD4/(hE)) is 5×105 um3/GPa or less.

The method or device of any prior embodiment, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one).

The method or device of any prior embodiment, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one), wherein the fourth power of the inter-spacer-distance (ISD) divided by the thickness (h) and the Young's modulus (E) of the flexible plate (ISD4/(hE)) is 5×106 um3/GPa or less.

The device of any prior device embodiment, wherein the ratio of the inter-spacing distance of the spacers to the average width of the spacer is 2 or larger, and the filling factor of the spacers multiplied by the Young's modulus of the spacers is 2 MPa or larger.

The method or device of any prior embodiment, wherein the analytes is proteins, peptides, nucleic acids, synthetic compounds, or inorganic compounds.

The method or device of any prior embodiment, wherein the sample is a biological sample selected from amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, and urine.

The method or device of any prior embodiment, wherein the spacers have a shape of pillars and a ratio of the width to the height of the pillar is equal or larger than one. The method of any prior embodiment, wherein the sample that is deposited on one or both of the plates has an unknown volume.

The method or device of any prior embodiment, wherein the spacers have a shape of pillar, and the pillar has substantially uniform cross-section.

The method or device of any prior embodiment, wherein the samples is for the detection, purification and quantification of chemical compounds or biomolecules that correlates with the stage of certain diseases.

The method or device of any prior embodiment, wherein the samples is related to infectious and parasitic disease, injuries, cardiovascular disease, cancer, mental disorders, neuropsychiatric disorders, pulmonary diseases, renal diseases, and other and organic diseases.

The method or device of any prior embodiment, wherein the samples is related to the detection, purification and quantification of microorganism.

The method or device of any prior embodiment, wherein the samples is related to virus, fungus and bacteria from environment, e.g., water, soil, or biological samples.

The method or device of any prior embodiment, wherein the samples is related to the detection, quantification of chemical compounds or biological samples that pose hazard to food safety or national security, e.g. toxic waste, anthrax.

The method or device of any prior embodiment, wherein the samples is related to quantification of vital parameters in medical or physiological monitor.

The method or device of any prior embodiment, wherein the samples is related to glucose, blood, oxygen level, total blood count.

The method or device of any prior embodiment, wherein the samples is related to the detection and quantification of specific DNA or RNA from biosamples.

The method or device of any prior embodiment, wherein the samples is related to the sequencing and comparing of genetic sequences in DNA in the chromosomes and mitochondria for genome analysis.

The method or device of any prior embodiment, wherein the samples is related to detect reaction products, e.g., during synthesis or purification of pharmaceuticals.

The method or device of any prior embodiment, wherein the samples is cells, tissues, bodily fluids, and stool:

The method or device of any prior embodiment, wherein the sample is the sample in the fields of human, veterinary, agriculture, foods, environments, and drug testing.

The method or device of any prior embodiment, wherein the sample is a biological sample is selected from hair, finger nail, ear wax, breath, connective tissue, muscle tissue, nervous tissue, epithelial tissue, cartilage, cancerous sample, or bone.

The devices or methods of any prior embodiment, wherein the inter-spacer distance is in the range of 5 um to 120 um. um The devices or methods of any prior embodiment, wherein the inter-spacer distance is in the range of 120 um to 200 um.

The device of any prior device embodiment, wherein the flexible plates have a thickness in the range of 20 um to 250 um and Young's modulus in the range 0.1 to 5 GPa.

The device of any prior device embodiment, wherein for a flexible plate, the thickness of the flexible plate times the Young's modulus of the flexible plate is in the range 60 to 750 GPa-um.

The device of any prior device embodiment, wherein the layer of uniform thickness sample is uniform over a lateral area that is at least 1 mm2.

The device of any prior device embodiment, wherein the layer of uniform thickness sample is uniform over a lateral area that is at least 3 mm2.

The device of any prior device embodiment, wherein the layer of uniform thickness sample is uniform over a lateral area that is at least 5 mm2.

The device of any prior device embodiment, wherein the layer of uniform thickness sample is uniform over a lateral area that is at least 10 mm2.

The device of any prior device embodiment, wherein the layer of uniform thickness sample is uniform over a lateral area that is at least 20 mm2.

The device of any prior device embodiment, wherein the layer of uniform thickness sample is uniform over a lateral area that is in a range of 20 mm2 to 100 mm2.

The device of any prior device embodiment, wherein the layer of uniform thickness sample has a thickness uniformity of up to +/−5% or better.

The device of any prior device embodiment, wherein the layer of uniform thickness sample has a thickness uniformity of up to +/−10% or better.

The device of any prior device embodiment, wherein the layer of uniform thickness sample has a thickness uniformity of up to +/−20% or better.

The device of any prior device embodiment, wherein the layer of uniform thickness sample has a thickness uniformity of up to +/−30% or better.

Additional Notes

Further examples of inventive subject matter according to the present disclosure are described in the following enumerated paragraphs.

It must be noted that as used herein and in the appended claims, the singular forms "a", "an", and "the" include plural referents unless the context clearly dictates otherwise, e.g., when the word "single" is used. For example, reference to "an analyte" includes a single analyte and multiple analytes, reference to "a capture agent" includes a single capture agent and multiple capture agents, reference to "a detection agent" includes a single detection agent and multiple detection agents, and reference to "an agent" includes a single agent and multiple agents.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function. Similarly, subject matter that is recited as being configured to perform a particular function may additionally or alternatively be described as being operative to perform that function.

As used herein, the phrase, "for example," the phrase, "as an example," and/or simply the terms "example" and "exemplary" when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally Similar and/or equivalent components, features, details, structures, embodiments, and/or methods, are also within the scope of the present disclosure.

As used herein, the phrases "at least one of" and "one or more of," in reference to a list of more than one entity, means any one or more of the entity in the list of entity, and is not limited to at least one of each and every entity specifically listed within the list of entity. For example, "at least one of A and B" (or, equivalently, "at least one of A or B," or, equivalently, "at least one of A and/or B") may refer to A alone, B alone, or the combination of A and B.

As used herein, the term "and/or" placed between a first entity and a second entity means one of (1) the first entity, (2) the second entity, and (3) the first entity and the second entity. Multiple entity listed with "and/or" should be construed in the same manner, i.e., "one or more" of the entity so conjoined. Other entity may optionally be present other than the entity specifically identified by the "and/or" clause, whether related or unrelated to those entities specifically identified.

Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

DETAILED DESCRIPTION OF EXEMPLARY EMBODIMENTS

The following detailed description illustrates some embodiments of the invention by way of example and not by way of limitation. The section headings and any subtitles used herein are for organizational purposes only and are not to be construed as limiting the subject matter described in any way. The contents under a section heading and/or subtitle are not limited to the section heading and/or subtitle, but apply to the entire description of the present invention.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF) that regulate the spacing between the plates. The term "X-plate" refers to one of the two plates in a CROF card, wherein the spacers are fixed to this plate. More descriptions of the COF Card, CROF Card, and X-plate are described in the provisional application Ser. Nos. 62/456,065, filed on Feb. 7, 2017 and U.S. Provisional Application No. 62/456,287, which was filed on Feb. 8, 2017, and US Provisional Application No. 62/456,504, which was filed on Feb. 8, 2017, all of which is incorporated herein in their entirety for all purposes.

QMAX Device for Nucleic Acid Capturing for Sequencing

Figure 1B:
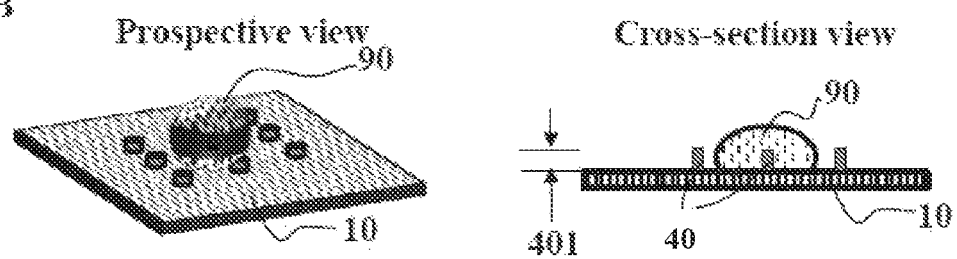
Figure 1C:
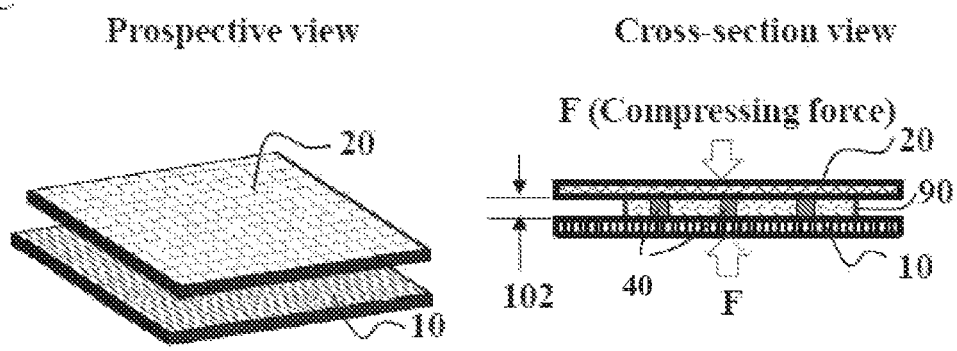

FIG. 1A-FIG. 1C is a schematic drawing for an exemplary embodiment of a QMAX (Q: quantification; M: magnifying; A: adding reagents; X: acceleration; also known as compressed regulated open flow (CROF)) device that can be used for capturing nucleic acid for sequencing. In FIG. 1A-FIG. 1C the QMAX device is in an open configuration. FIG. 1A shows a QMAX comprising a first plate, a second plate, and wells on the second plate. FIG. 1B shows a view of well array on the first plate. FIG. 1O shows a view of pillar array on the second plate.

A QMAX device for capturing nucleic acid for sequencing comprising:

a first plate, a second plate, and wells, wherein (a) the first and second plates are movable relative to each other into different configurations, and have, on its respective surface, a sample contact area for contacting a fluidic sample that contains a target analyte;

(b) the second plate has, in the sample contact area, a plurality of the wells, wherein each well has (i) a well depth of 50 um or less, (ii) a well volume substantially less than that of the sample, and (iii) a binding site with capture probes immobilized at the site, and the capture probes captures the target probes;

wherein one of the configurations is an open configuration, in which: the average spacing between the inner surface of the first plate and the rim of the wells in the second plate is at least 300 urn and the sample is deposited on one or both of the plates;

wherein another of the configurations is a close configuration, which is the configuration after the sample is deposited in the open configuration; in the closed configuration, at least a part of the sample is inside the wells, and the average spacing between the inner surface of the first plate and the rim of the well in the second plate is less than 1/10 (one tenth) of the average spacing in open configuration.

Figures 36A, 36B:
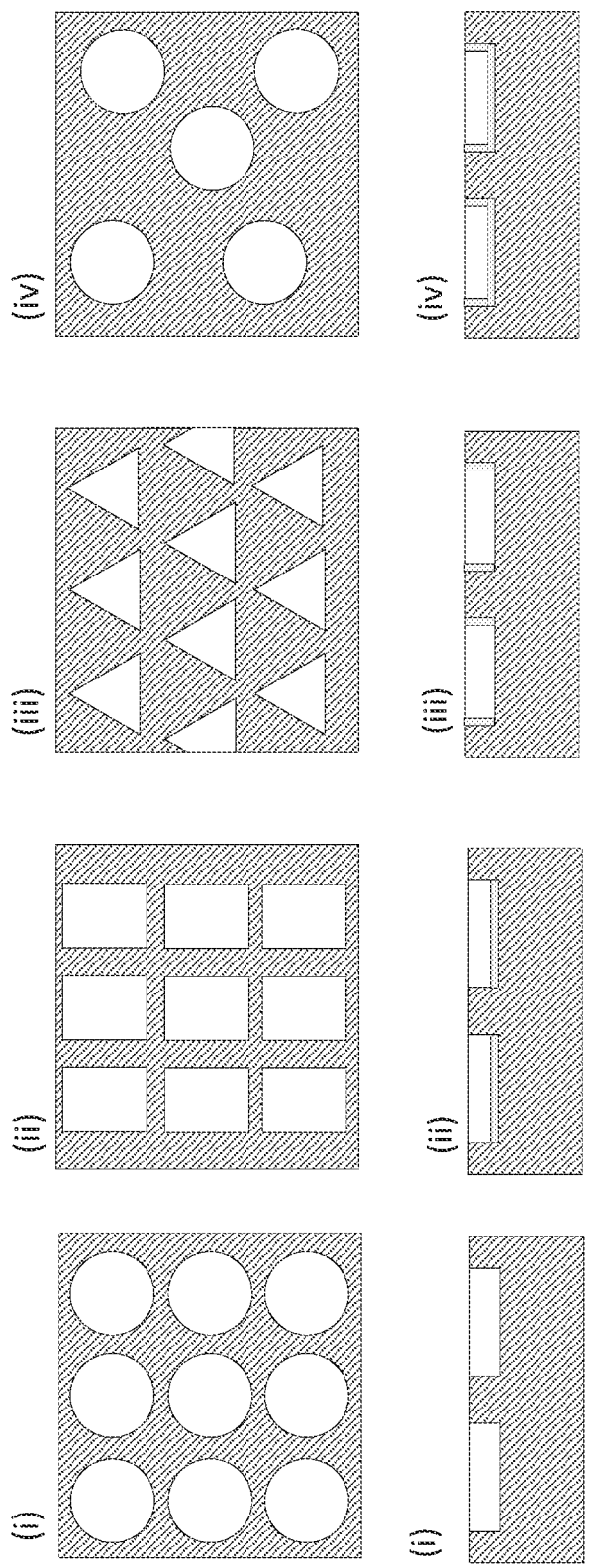
FIG. 36a-FIG. 36b is schematic drawings for exemplary embodiments of wells on first plate of QMAX.

FIG. 36a-FIG. 36b is schematic drawings for exemplary embodiments of wells on first plate of QMAX. FIG. 36a shows a view of wells on first plate with (i) round shape with square lattice (ii) rectangle shape with square lattice (iii) triangle shape with hexagonal lattice (iv) round shape with aperiodicity. FIG. 36b shows a view of well array on first plate with (i) no metal coating (ii) metal coating on bottom of the well (iii) metal coating on side wall of the well (iv) metal coating on both bottom and side wall of the well.

In some embodiments, the well on the first plate has periods (average well to well center distance) of 1 nm, 10 nm, 100 nm, 500 nm, 1 um, 5 um, 50 um, 500 um, 1 mm, or a range between any two of the values; and a preferred range of 10 nm to 100 nm, 100 nm to 500 nm, 500 nm to 1 um, 1 um to 10 um, or 10 um to 50 um (Period).

In some embodiments, the well on the first plate has well size (average length or diameter) of 1 nm, 10 nm, 100 nm, 500 nm, 1 um, 5 um, 50 um, 500 um, 1 mm, or a range between any two of the values; and a preferred range of 10 nm to 100 nm, 100 nm to 500 nm, 500 nm to 1 um, 1 um to 10 um, or 10 um to 50 um (Size).

In some embodiments, the well on the first plate has depth of 1 nm, 10 nm, 100 nm, 500 nm, 1 um, 5 um, 50 um, 500 um, 1 mm, or a range between any two of the values; and a preferred range of 10 nm to 100 nm, 100 nm to 500 nm, 500 nm to 1 um, 1 um to 10 um, or 10 um to 50 um (Depth).

In some embodiments, well depth is 0, meaning no well on the first plate.

In some embodiments, well is "pillar" instead, with pillar height of 1 nm, 10 nm, 100 nm, 500 nm, 1 um, 5 um, 50 um, 500 um, 1 mm, or a range between any two of the values; and a preferred range of 10 nm to 100 nm, 100 nm to 500 nm, 500 nm to 1 um, 1 um to 10 um, or 10 um to 50 um (pillar height).

In some embodiments, wells have (i) no metal coating (ii) metal coating on bottom of the well (top of the pillar) (iii) metal coating on side wall of the well (side of the pillar) (iv) metal coating on both bottom and side wall of the well.

In some embodiments, the coating metal is gold, aluminum, silver, copper, tin and/or their combinations.

In some embodiments, the well area ratio (ratio of the well area to the total area of the surface) is 40% to 50%, 50% to 60%, 60% to 70%, 70% to 80%, 80% to 90%, 90% to 99% or a range between any two of the values.

In some embodiments, the well numbers on the first plate is larger than the nucleic acid probe numbers in the sample, For example, total well number on the first plate is 1 to 2 times, 2 to 5 times, 5 to 10 times, 10 to 100 times, 100 to 1000 times, 1000 to 10000 times of 600, If the nucleic acid probe concentration is 1 fM with volume of 1 uL;

For example, total well number on the first plate is 1 to 2 times, 2 to 5 times, 5 to 10 times, 10 to 100 times, 100 to 1000 times, 1000 to 10000 times of 600,000, If the nucleic acid probe concentration is 1 pM with volume of 1 uL;

For example, total well number on the first plate is 1 to 2 times, 2 to 5 times, 5 to 10 times, 10 to 100 times, 100 to 1000 times, 1000 to 10000 times of 600,000,000, If the nucleic acid probe concentration is 1 nM with volume of 1 uL;

In some embodiments, well number is in such way to achieve, after nucleic acid capture step, most of the wells capture no more than 1 target nucleic acid probe.

Table 1 shows one example of the DNA probe number in 1 uL sample with concentration 1 fM to 100 pM.

Table 2 shows one example of the well number in 2 cm×2 cm area with well pitch 1 um to 1 mm.

TABLE 1

| DNA probe number in 1 µl sample | |
|---|---|
| Concentration | Molecule Number |
| 1 fM | $6 \times 10^2$ |
| 10 fM | $6 \times 10^3$ |
| 100 fM | $6 \times 10^4$ |
| 1 pM | $6 \times 10^5$ |
| 10 pM | $6 \times 10^6$ |
| 100 pM | $6 \times 10^7$ |
| 100 pM | $6 \times 10^8$ |

TABLE 2

| Well number in 2 cm × 2 cm area | |
|---|---|
| Pitch | Well Number |
| 1 mm | $4 \times 10^2$ |
| 300 µm | $4 \times 10^3$ |

TABLE 2-continued

Well number in 2 cm × 2 cm area

| Pitch | Well Number |
|---|---|
| 100 μm | $4 \times 10^4$ |
| 30 μm | $4 \times 10^5$ |
| 10 μm | $4 \times 10^6$ |
| 3 μm | $4 \times 10^7$ |
| 1 μm | $4 \times 10^8$ |

For example, with well pitch 100 um, total well number on first plate with size of 4 cm² is 40000. If using such well plate measure 1 fM DNA sample in 1 uL sample, which has 600 DNA probes, statistically each well will have no more than one molecule.

In some embodiments, the second plate is a X-Plate.

In some embodiments, the first plate can be any material with flat or engineered solid surface. Examples for the first plate include but are but not limited to: plastic, silicon, PMMA, gold and glass. In some embodiments, the second plate can be any material with flat or engineered solid surface. Examples for the first plate include but are but not limited to: plastic, silicon, PMMA, gold and glass.

In some embodiments, the first plate is made of semiconductors including carbon, germanium, selenium, silicon, gallium arsenide (GaAs), gallium nitride (GaN), indium phosphide (InP), zinc selenide (ZnSe), and silicon carbide (SiC); metals including gold, aluminum, silver, copper, tin and/or their combinations.

In some embodiments, the surface of the first plate facing the second plate is defined as the inner surface of the first plate; the surface of the second plate that faces the first plate are also defined as the inner surface of the second plate. In some embodiments, the inner surfaces of the respective plates comprise a sample contact area for contacting a sample that comprises nucleic acid. The sample contact area can occupy part or the entirety of the respective inner surface. As shown in FIG. 35a-FIG. 35c, the second plate can comprises spacers that are fixed on the inner surface of the second plate. It should be noted, however, that in some embodiments the spacers are fixed on the inner surface of the first plate and in other embodiments on the inner surfaces of both the second plate and the first plate.

FIG. 35a-FIG. 35c shows a sectional view of the plates in an open configuration, in which the first plate and second plate are partially or entirely separated apart, allowing a sample to be deposited on either one or both of the plates.

The first plate and second plate are moveable relative to each other into different configuration. One of the configurations is an open configuration, in which the two plates are partially or entirely separated apart and the spacing between the plates are not regulated by the spacers. FIG. 35a-FIG. 35c shows the plates in the open configuration, in which a sample, can be added to first plate, the second plate, or both of the plates. In some embodiments, the inner surface of a respective plate comprises a sample contact area, which occupies a part of the entirety of the inner surface. In certain embodiments, the spacers are positioned within the sample contact area. In some embodiments, the spacers are not fixed to any one of the plates, but are mixed in the sample.

The Method of Using the QMAX Device for Nucleic Acid Capturing for Sequencing

Figure 37:
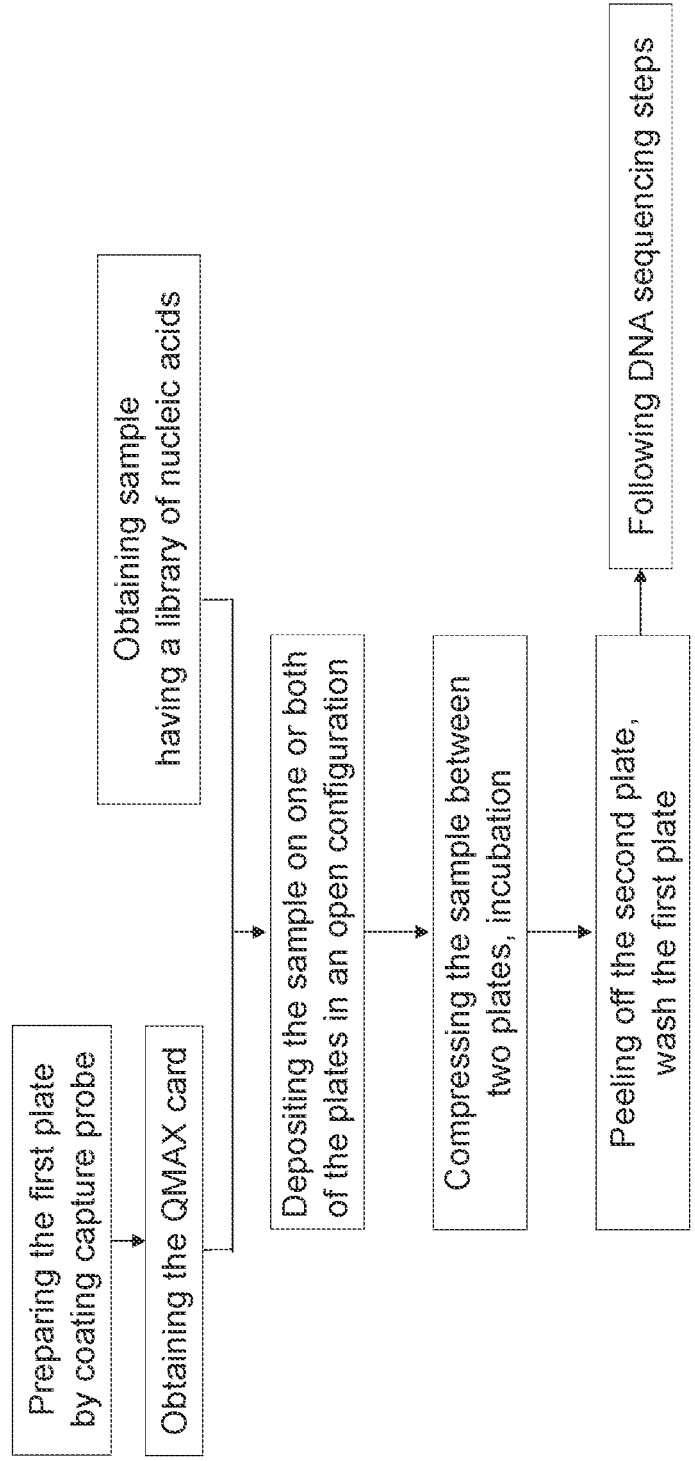
FIG. 37 is a flow chart showing an implementation of the method.

FIG. 37 is a flow chart showing the basic steps in an exemplary process for conducting a nucleic acid probe capture step in nucleic acid sequencing using the QMAX device.

A method of capturing nucleic acid probe for sequencing, comprising:
(a) preparing the first plate by coating capture probes;
(b) obtaining a device of claim 1;
(c) obtaining a sample that contains target nucleic acid;
(d) depositing the sample on one or both of the plates when the plates are configured in an open configuration; in which: the average spacing between the inner surface of the first plate and the rim of the wells in the second plate is at least 300 um;
(e) after (d), moving the two plates of the device of claim 1 into a close configuration, in which, at least a part of the sample is inside the wells, and the average spacing between the inner surface of the first plate and the rim of the well in the second plate is less than $\frac{1}{10}$ (one tenth) of the average spacing in open configuration;
(f) peeling off the second plate, and wash the first plate;
(g) following nucleic acid sequencing steps.

As used herein, the terms "nucleic acid" and "nucleotide" are intended to be consistent with their use in the art and to include naturally occurring species or functional analogs thereof. Particularly useful functional analogs of nucleic acids are capable of hybridizing to a nucleic acid in a sequence specific fashion or capable of being used as a template for replication of a particular nucleotide sequence. Naturally occurring nucleic acids generally have a backbone containing phosphodiester bonds. An analog structure can have an alternate backbone linkage including any of a variety of those known in the art. Naturally occurring nucleic acids generally have a deoxyribose sugar (e.g. found in deoxyribonucleic acid (DNA)) or a ribose sugar (e.g. found in ribonucleic acid (RNA)). A nucleic acid can contain nucleotides having any of a variety of analogs of these sugar moieties that are known in the art. A nucleic acid can include native or non-native nucleotides. In this regard, a native deoxyribonucleic acid can have one or more bases selected from the group consisting of adenine, thymine, cytosine or guanine and a ribonucleic acid can have one or more bases selected from the group consisting of uracil, adenine, cytosine or guanine. Useful non-native bases that can be included in a nucleic acid or nucleotide are known in the art. The terms "probe" or "target," when used in reference to a nucleic acid, are intended as semantic identifiers for the nucleic acid in the context of a method or composition set forth herein and does not necessarily limit the structure or function of the nucleic acid beyond what is otherwise explicitly indicated. The terms "probe" and "target" can be similarly applied to other analytes such as proteins, small molecules, cells or the like.

As used herein, the term "capture probe" refers to nucleic acid that hybridizes to nucleic acid having a complementary sequence.

The term "complementary" as used herein refers to a nucleotide sequence that base-pairs by hydrogen bonds to a target nucleic acid of interest. In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. Typically, "complementary" refers to a nucleotide sequence that is fully complementary to a target of interest such that every nucleotide in the sequence is complementary to every nucleotide in the target nucleic acid in the corresponding positions. When a nucleotide sequence is not fully complementary (100% complementary) to a non-target sequence but still may base pair to the non-target sequence due to complementarity of certain stretches of nucleotide sequence to the non-target sequence, percent complementarily may be calculated to assess the possibility of a non-specific (off-target) binding. In general, a complementary of 50% or less does not lead to non-specific binding. In addition, a complementary of 70% or less may not lead to non-specific binding under stringent hybridization conditions.

In some embodiments, the capture probe is attached to the surface of the first plate. In certain embodiments, the capture probe can immobilize the onto the inner surface of the first plate.

As used herein, the term "coat," when used as a verb, is intended to mean providing a layer or covering on a surface. At least a portion of the surface can be provided with a layer or cover. In some cases, the entire surface can be provided with a layer or cover. In alternative cases, only a portion of the surface will be provided with a layer or covering. The term "coat," when used to describe the relationship between a surface and a material, is intended to mean that the material is present as a layer or cover on the surface. The material can seal the surface, for example, preventing contact of liquid or gas with the surface. However, the material need not form a seal. For example, the material can be porous to liquid, gas, or one or more components carried in a liquid or gas. Exemplary materials that can coat a surface include, but are not limited to, a gel, polymer, organic polymer, liquid, metal, a second surface, plastic, silica, or gas.

As used herein, the term "attached" refers to the state of two things being joined, fastened, adhered, connected or bound to each other. For example, an analyte, such as a nucleic acid, can be attached to a material, such as a gel or solid support, by a covalent or non-covalent bond. A covalent bond is characterized by the sharing of pairs of electrons between atoms. A non-covalent bond is a chemical bond that does not involve the sharing of pairs of electrons and can include, for example, hydrogen bonds, ionic bonds, van der Waals forces, hydrophilic interactions and hydrophobic interactions.

In several embodiments, primer nucleic acids that are attached to the first plate can be used for capture and/or amplification of template nucleic acids. The primers can be universal primers that hybridize to a universal adapter sequence that is attached to different target nucleic acids in a library (i.e. each target nucleic acid includes a target region that differs from other target nucleic acids in the library and several target nucleic acids in the library have the same universal adapter sequence). In some embodiments, a target nucleic acid can be attached to gel material, and primers (whether in solution or also attached to the gel) can be used to amplify the attached target nucleic acid (i.e. the target nucleic acid can serve as a template for amplification).

More particularly in step (a), in some embodiments, the first plate comprises a capture probe that is coated fully or partially on the inner surface of the first plate.

In some embodiments, the first plate comprises a capture probe that is coated fully or partially inside the wells on the first plate.

In some embodiments, the first plate comprises a capture probe that is coated fully or partially on the metal inside the wells on the first plate.

In some embodiments, the capture probes can be applied to the surface by printing, spraying, soaking or any other method that applies homogenous layer of capture probes. In certain embodiments, the capture probes is dried on the first plate.

More particular in step (c), as used herein, the term "library" refers to a collection of analytes having different chemical compositions. Typically, the analytes in a library will be different species having a common feature or characteristic of a genera or class, but otherwise differing in some way. For example, a library can include nucleic acid species that differ in nucleotide sequence, but that are similar with respect to having a sugar-phosphate backbone.

As used herein, the term "different", when used in reference to nucleic acids, means that the nucleic acids have nucleotide sequences that are not the same as each other. Two or more nucleic acids can have nucleotide sequences that are different along their entire length. Alternatively, two or more nucleic acids can have nucleotide sequences that are different along a substantial portion of their length. For example, two or more nucleic acids can have target nucleotide sequence portions that are different for the two or more molecules while also having a universal sequence portion that is the same on the two or more molecules.

In some embodiments, the method of the present invention, before step (f) and after step (e), further comprise incubating the layer of uniform thickness for a predetermined period of time. In certain embodiments, the predetermined period of time is equal to or longer than the time needed for the target nucleic acids to diffuse into the sample across the layer of uniform thickness.

In certain embodiments, the predetermined period of time is equal to or longer than the time needed for the target nucleic acids to diffuse into the sample across the layer of uniform thickness and captured by capture probe.

In certain embodiments, the predetermined period of time is equal to or longer than the time needed for the target nucleic acids to diffuse into the sample across the layer of uniform thickness, captured by capture probe and being amplified to produce a clonal population of an individual nucleic acid in each of the wells.

As used herein, the term "clonal population" refers to a population of nucleic acids that is homogeneous with respect to a particular nucleotide sequence. The homogenous sequence is typically at least 10 nucleotides long, but can be even longer including for example, at least 50, 100, 250, 500, 1000 or 2500 nucleotides long. A clonal population can be derived from a single target nucleic acid or template nucleic acid. A clonal population can include at least 2, 5, 10, 100, 1000 or more copies of a target nucleotide sequence. The copies can be present in a single nucleic acid molecule, for example, as a concatamer or the copies can be present on separate nucleic acid molecules (i.e. a clonal population can include at least 2, 5, 10, 100, 1000 or more nucleic acid molecules having the same target nucleotide sequence). Typically, all of the nucleic acids in a clonal population will have the same nucleotide sequence. It will be understood that a negligible number of contaminant nucleic acids or mutations (e.g. due to amplification artifacts) can occur in a clonal population without departing from clonality. Thus, a population can be at least 80%, 90%, 95% or 99% clonal. In some cases 100% pure clonal populations may be present.

A method set forth herein can use any of a variety of amplification techniques. Exemplary techniques that can be used include, but are not limited to, polymerase chain reaction (PCR), rolling circle amplification (RCA), multiple displacement amplification (MDA), or random prime amplification (RPA). In particular embodiments, one or more primers used for amplification can be attached to a gel material. In PCR embodiments, one or both of the primers used for amplification can be attached to a gel material. Formats that utilize two species of attached primer are often referred to as bridge amplification because double stranded amplicons form a bridge-like structure between the two attached primers that flank the template sequence that has been copied. Exemplary reagents and conditions that can be used for bridge amplification are described, for example, in U.S. Pat. No. 5,641,658; U.S. Patent Publ. No. 2002/0055100; U.S. Pat. No. 7,115,400; U.S. Patent Publ. No. 2004/0096853; U.S. Patent Publ. No. 2004/0002090; U.S. Patent Publ. No. 2007/0128624; and U.S. Patent Publ. No. 2008/0009420, each of which is incorporated herein by reference. PCR amplification can also be carried out with one of the amplification primers attached to a gel material and the second primer in solution. An exemplary format that uses a combination of one solid phase-attached primer and a solution phase primer is emulsion PCR as described, for example, in Dressman et al., Proc. Natl. Acad. Sci. USA 100:8817-8822 (2003), WO 05/010145, or U.S. Patent Publ. Nos. 2005/0130173 or 2005/0064460, each of which is incorporated herein by reference. Emulsion PCR is illustrative of the format and it will be understood that for purposes of the methods set forth herein the use of an emulsion is optional and indeed for several embodiments an emulsion is not used. Furthermore, primers need not be attached directly to solid supports as set forth in the ePCR references and can instead be attached to a gel material as set forth herein. In some solid phase PCR or bridge amplification formats, a target nucleic acid can be attached to a gel material and used as a template for amplification.

RCA techniques can be modified for use in a method of the present disclosure. Exemplary components that can be used in an RCA reaction and principles by which RCA produces amplicons are described, for example, in Lizardi et al., Nat. Genet. 19:225-232 (1998) and US Pat. App. Pub. No. 2007/0099208 A1, each of which is incorporated herein by reference. Primers used for RCA can be in solution or attached to a gel material.

MDA techniques can be modified for use in a method of the present disclosure. Some basic principles and useful conditions for MDA are described, for example, in Dean et al., Proc Natl. Acad. Sci. USA 99:5261-66 (2002); Lage et al., Genome Research 13:294-307 (2003); Walker et al., Molecular Methods for Virus Detection, Academic Press, Inc., 1995; Walker et al., Nucl. Acids Res. 20:1691-96 (1992); U.S. Pat. Nos. 5,455,166; 5,130,238; and 6,214,587, each of which is incorporated herein by reference. Primers used for MDA can be in solution or attached to a gel material.

In particular embodiments a combination of the above-exemplified amplification techniques can be used. For example, RCA and MDA can be used in a combination wherein RCA is used to generate a concatameric amplicon in solution (e.g. using solution-phase primers). The amplicon can then be used as a template for MDA using primers that are attached to a gel material. In this example, amplicons produced after the combined RCA and MDA steps will be attached to the gel material. The amplicons will generally contain concatameric repeats of a target nucleotide sequence.

Amplification techniques, such as those exemplified above, can be used to produce gel-containing features having multiple copies of target nucleic acids. An individual feature, such as a well, can have a clonal population of nucleotide sequences in the form of a single molecule concatamer, such as those produced by RCA, or in the form of many nucleic acid molecules having the same sequence such as those produced by bridge PCR. Generally, the nucleic acid(s) having several copies of the amplified target will be attached to the gel material.

In certain embodiments, the predetermined period of time is less than 10 seconds, 20 seconds, 30 seconds, 45 seconds, 1 minute, 1.5 minutes, 2 minutes, 3 minutes, 4 minutes, 5 minutes, 6 minutes, 7 minutes, 8 minutes, 9 minutes, 10 minutes, 15 minutes, 20 minutes, 30 minutes, or 60 minutes, or in a range between any of the two values.

In some embodiments, for the method of the present invention, the sample is deposited on the first plate. In certain embodiments, before step (e) after step (d), the sample is incubated on the first plate for a predetermined period of time. In certain embodiments, the predetermined period of time is equal to or longer than the time needed for the binding between the capture antibody and the analyte to reach an equilibrium. In certain embodiments, the predetermined period of time is less than 10 seconds, 20 seconds, 30 seconds, 45 seconds, 1 minute, 1.5 minutes, 2 minutes, 3 minutes, 4 minutes, 5 minutes, 6 minutes, 7 minutes, 8 minutes, 9 minutes, 10 minutes, 15 minutes, 20 minutes, 30 minutes, or 60 minutes, or in a range between any of the two values.

In some embodiments, for the method of the present invention, after step (e), the inner surface of the first plate can be washed to remove unbound molecules. For this approach, washing is conducted before switch the plates into the closed configuration. In some embodiments, for the method of the present invention, before step (e) and after step (d), before step (f) and after step (e), the plates can be switched into the open configuration (e.g. by removing the second plate) and the inner surface of the first plate can be washed. For this approach, washing is conducted before switch the plates into the closed configuration. In certain embodiments, such a step reduces non-specific binding and reduce signal noise. In certain embodiments, each of the wash step includes only one or multiple washes. In some embodiments, both of the washing steps are conducted. In some embodiments, only one of the washing steps is conducted.

In some embodiments, the inner surface can be washed with washing solution absorbed in a sponge. In some embodiments, the washing is conducted by squeezing the sponge to release the wash solution onto the inner surface of the first plate and releasing the sponge to reabsorb the wash solution. In some embodiments, the washing improves the limit of detection (LOD) for the detectable signal.

Following the step (f), nucleic acids captured on the first plate can be used in many biological applications, including sequencing procedure, such as a sequencing-by-synthesis (SBS) technique. Briefly, SBS can be initiated by contacting the target nucleic acids with one or more labeled nucleotides, DNA polymerase, etc. Those features where a primer is extended using the target nucleic acid as template will incorporate a labeled nucleotide that can be detected. Optionally, the labeled nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with an array produced by the methods of the present disclosure are described, for example, in Bentley et al., Nature 456: 53-59 (2008), WO 04/018497; WO 91/06678; WO 07/123744; U.S. Pat. Nos. 7,057,026; 7,329,492; 7,211,414; 7,315,019 or 7,405,281, and US Pat. App. Pub. No. 2008/0108082 A1, each of which is incorporated herein by reference.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., Analytical Biochemistry 242 (1), 84-9 (1996); Ronaghi, Genome Res. 11 (1), 3-11 (2001); Ronaghi et al. Science 281 (5375), 363 (1998); U.S. Pat. Nos. 6,210,891; 6,258,568 and 6,274,320, each of which is incorporated herein by reference). In pyrosequencing, released PPi can be detected by being converted to adenosine triphosphate (ATP) by ATP sulfurylase, and the resulting ATP can be detected via luciferase-produced photons. Thus, the sequencing reaction can be monitored via a luminescence detection system. Excitation radiation sources used for fluorescence based detection systems are not necessary for pyrosequencing procedures. Useful fluidic systems, detectors and procedures that can be used for application of pyrosequencing to arrays of the present disclosure are described, for example, in WIPO Pat. App. Ser. No. PCT/US11/57111, US Pat. App. Pub. No. 2005/0191698 A1, U.S. Pat. Nos. 7,595,883, and 7,244,559, each of which is incorporated herein by reference.

Sequencing-by-ligation reactions are also useful including, for example, those described in Shendure et al. Science 309:1728-1732 (2005); U.S. Pat. Nos. 5,599,675; and 5,750,341, each of which is incorporated herein by reference. Some embodiments can include sequencing-by-hybridization procedures as described, for example, in Bains et al., Journal of Theoretical Biology 135 (3), 303-7 (1988); Drmanac et al., Nature Biotechnology 16, 54-58 (1998); Fodor et al., Science 251 (4995), 767-773 (1995); and WO 1989/10977, each of which is incorporated herein by reference. In both sequencing-by-ligation and sequencing-by-hybridization procedures, nucleic acids that are present in gel-containing wells (or other concave features) are subjected to repeated cycles of oligonucleotide delivery and detection. Fluidic systems for SBS methods as set forth herein, or in references cited herein, can be readily adapted for delivery of reagents for sequencing-by-ligation or sequencing-by-hybridization procedures. Typically, the oligonucleotides are fluorescently labeled and can be detected using fluorescence detectors similar to those described with regard to SBS procedures herein or in references cited herein.

Some embodiments can utilize methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zeromode waveguides. Techniques and reagents for FRET-based sequencing are described, for example, in Levene et al. Science 299, 682-686 (2003); Lundquist et al. Opt. Lett. 33, 1026-1028 (2008); Korlach et al. Proc. Natl. Acad. Sci. USA 105, 1176-1181 (2008), the disclosures of which are incorporated herein by reference.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in US Pat. App. Pub. Nos. 2009/0026082 A1; 2009/0127589 A1; 2010/0137143 A1; or 2010/0282617 A1, each of which is incorporated herein by reference. In particular embodiments, the electrical detectors that are used to detect the released protons can be modified to include wells and the wells can contain gel material as set forth herein.

In some embodiments of QMAX, the sample contact area of one or both of the plates comprises a compressed open flow monitoring surface structures (MSS) that are configured to monitoring how much flow has occurred after COF. For examples, the MSS comprises, in some embodiments, shallow square array, which will cause friction to the components (e.g. blood cells in a blood) in a sample. By checking the distributions of some components of a sample, one can obtain information related to a flow, under a COF, of the sample and its components.

The depth of the MSS can be $1/1000$, $1/100$, $1/100$, $1/5$, $1/2$ of the spacer height or in a range of any two values, and in either protrusion or well form.

EXAMPLES OF PRESENT INVENTION

Figure 38:
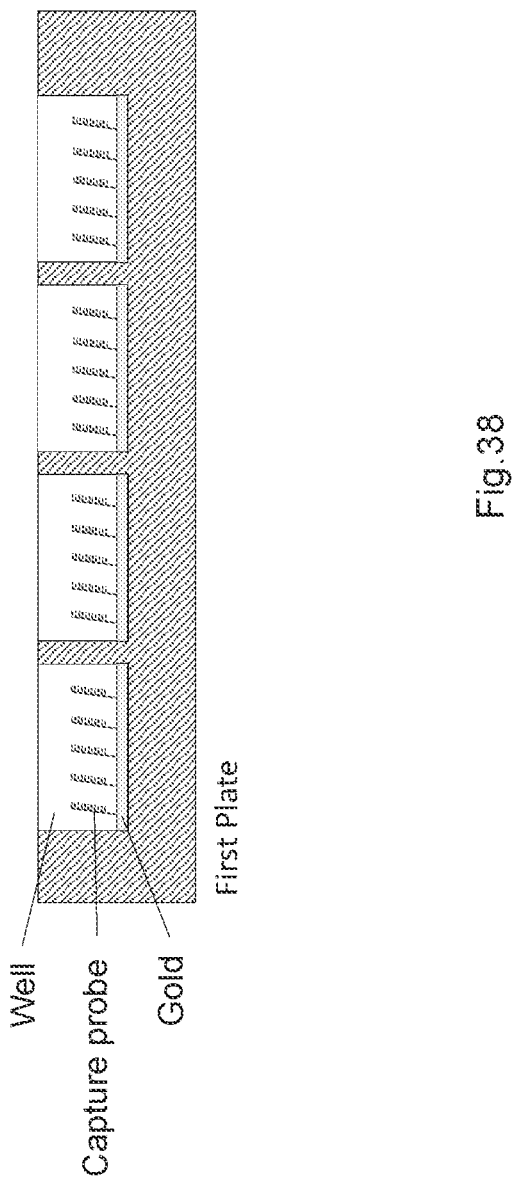
FIG. 38 shows an example of first plate preparation step for nucleic acid sequencing.

FIG. 38 shows an example of first plate preparation step for nucleic acid sequencing.

The first plate in this example is square well with size of 3 um by 3 um, period of 5 um, depth of 1 um fabricated on 1 mm thick acrylic substrate. On the bottom of each well has 100 nm gold and 1 nm titanium deposited. In this device, each 1 $mm^2$ area first plate has 40,000 wells. The fabrication of this nanostructure by large area nanofabrication methods including nanoimprint lithography, reactive ion etching (RIE), E-beam evaporation and others.

Figure 39:
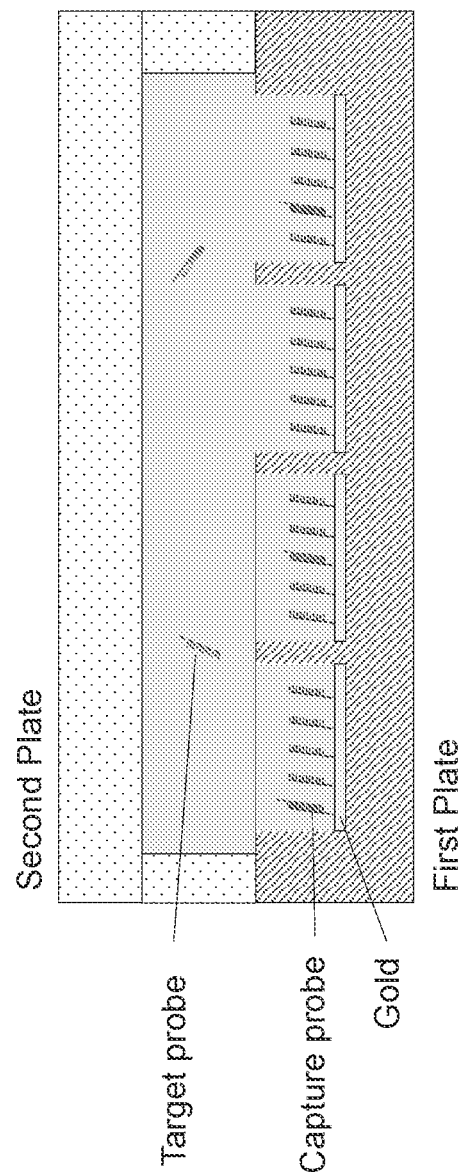
FIG. 39 is a schematic drawing for an exemplary embodiment of a QMAX device in a closed configuration for capturing target nucleic acid.

1 uM of thiolated capture probe was selected coated on gold on well bottom at room temperature for overnight;

Then the first plate was rinsed with PBST for 3 times, and then blocked with 50 uM MCH for 30 min, and then rinsed with PBST for 3 times;

FIG. 39 is a schematic drawing for an exemplary embodiment of a QMAX device in a closed configuration for capturing target nucleic acid.

Add 1 ul of target probe (concentration is much less than 1 pM diluted in TE buffer, which is to make sure the number of total nucleic acid probes in sample is much less than the well numbers on the first plate) onto first plate in open configuration;

In some embodiments, the target probe is conjugated a label to facilize the following measurement and evaluation of binding probes. The label is a light-emitting label or an optical detectable label, directly or indirectly, either prior to or after it is bound to said capture agent. The label is label with signal of Raman scattering, chromaticity, luminescence, fluorescence, electroluminescence, chemiluminescence, and/or electrochemiluminescence. As used herein, the term "light-emitting label" refers to a label that can emit light when under an external excitation. This can be luminescence. Fluorescent labels (which include dye molecules or quantum dots), and luminescent labels (e.g., electro- or chemi-luminescent labels) are types of light-emitting label. The external excitation is light (photons) for fluorescence, electrical current for electroluminescence and chemical reaction for chemi-luminscence. An external excitation can be a combination of the above. The phrase "labeled analyte" refers to an analyte that is detectably labeled with a light emitting label such that the analyte can be detected by assessing the presence of the label. A labeled analyte may be labeled directly (i.e., the analyte itself may be directly conjugated to a label, e.g., via a strong bond, e.g., a covalent or non-covalent bond), or a labeled analyte may be labeled indirectly (i.e., the analyte is bound by a secondary capture agent that is directly labeled).

Press the second plate on top of the liquid by hand and QMAX is in close configuration; Second plate used here is a X-Plate with 30×40 um pillar size, 80 um inter spacing distance, 30 um pillar height on 175 um PMMA substrate.

Incubate the QMAX device for 1 min; peel off the second plate;

Rinse the first plate with sponge, which contains DNA washer (5×SSC+0.05% Tween 20) for 3 times;

The first plate is ready for following nucleic acid sequencing steps.

Examples for Results

Figure 40:
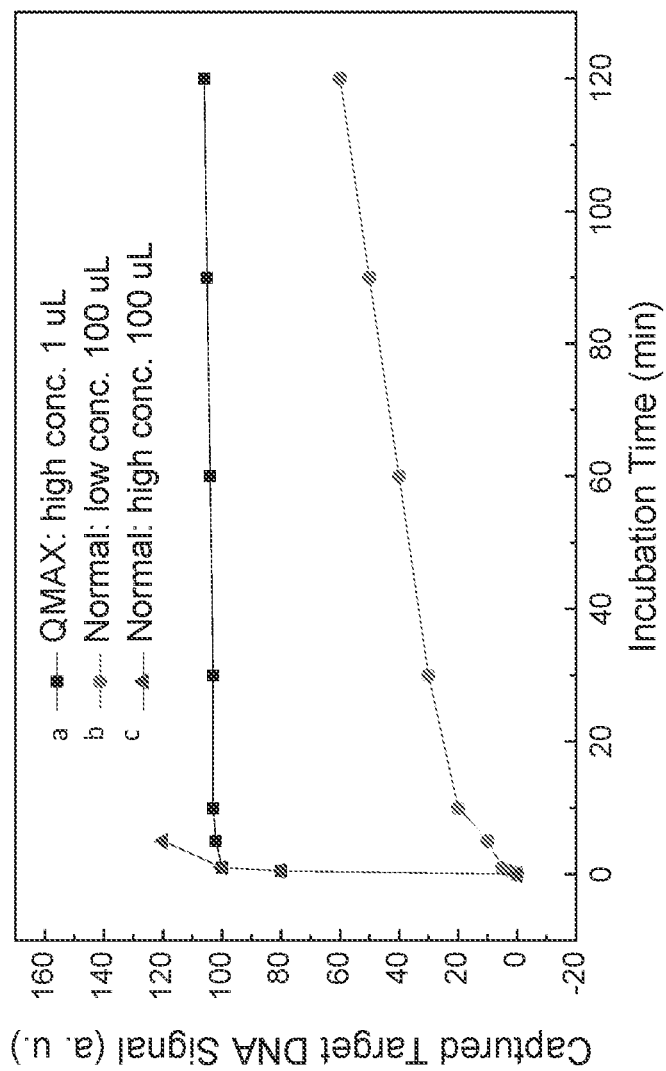
FIG. 40 shows representative a time course study for capturing target DNA with (a) QMAX using 1 pM concentration 1 uL target nucleic acid sample.

FIG. 40 shows representative a time course study for capturing target DNA with (a) QMAX using 1 pM concentration 1 uL target nucleic acid sample; (b) normal 96 microwell plate using 10 fM concentration 100 uL nucleic acid sample; (c) normal 96 microwell plate using 1 pM concentration 100 uL target nucleic acid sample. The x-axis is the incubation time. The y-axis is the fluorescence signal from IR-800 dye conjugated on captured nucleic acid. The experiment process follows the flow chart of FIG. 37.

Clearly, QMAX device has the fastest incubation saturation time (around 1 min) and requires smallest sample volume (1 uL). While incubating first plate in normal 96 microwell, with low concertation (10 fM) 100 uL sample, capturing process is not saturated within 120 min, and first plate has much lower signal; While incubating first plate in normal 96 microwell, with same high concertation (1 pM) 100 uL sample, capturing process is not saturated as fast as QMAX device and requires 100 times sample volume than QMAX device.

As demonstrated by the examples, in some embodiments, the present invention provides a platform for capturing nucleic acid for sequencing, that is fast, simple, portable and only requires as little as 1 μL or less of sample. With the current invention, nucleic acid capturing can be performed in a shallow enclosed space with designated parameters so that the sample volume and capturing time can be accurately controlled. In some embodiments, Brownian motion of molecules is restricted in the shallow space so that equilibrium of molecule binding can be reached faster. This platform can be adapted for any nucleic acid sequencing that are performed in traditional micro titer plate and thus have broad applications.

Additional Examples

In the device or method herein described, the spacers can have a height of 100 nm, 1 um, 5 um, 10 um, 20 um, 50 um, 500 um, 1 mm, or a range between any two of the values; and a preferred range of 500 nm to 1 um, 1 um to 10 um, or 10 um to 30 um, 30 um to 50 um.

In the device or method herein described, the spacers can have a height of 1 um or less, thereby the saturation incubation time (or saturation binding time) is less than 0.1 s for protein, 0.1 s for nucleic acid (20 bp).

In the device or method herein described, the spacers can have a height of 2 um or less, thereby the saturation incubation time (or saturation binding time) is less than 0.3 s for protein, 0.1 s for nucleic acid (20 bp).

In the device or method herein described, the spacers can have a height of 5 um or less, thereby the saturation incubation time (or saturation binding time) is less than 2 s for protein, 1 s for nucleic acid (20 bp).

In the device or method herein described, the spacers can have a height of 10 um or less, thereby the saturation incubation time (or saturation binding time) is less than 10 s for protein, 5 s for nucleic acid (20 bp).

In the device or method herein described, the spacers can have a height of 30 um or less, thereby the saturation incubation time (or saturation binding time) is less than for 60 s protein, 30 s for nucleic acid (20 bp).

In the device or method herein described, the spacers can have a height of 50 um or less, thereby the saturation incubation time (or saturation binding time) is less than 2 min for protein, 1 min for nucleic acid (20 bp).

In the device or method herein described, the spacers can have a height of 100 um or less, thereby the saturation incubation time (or saturation binding time) is less than 10 min for protein, 5 min for nucleic acid (20 bp).

In the device or method herein described, the sample can be incubated for a saturation binding time. In some embodiments, the saturation binding time is equal to or longer than the time that it takes for the target entity to diffuse across the thickness of the uniform thickness layer at the closed configuration. In some embodiments, the saturation binding time is equal to or longer than the time that it takes for the target entity to diffuse across the thickness of the uniform thickness layer at the closed configuration and to bind to the binding site. In some embodiments, the saturation binding time is significantly shorter than the time that it takes the target entity to laterally diffuse across the minimum lateral dimension of the binding site. In some embodiments, the saturation binding time is wherein at the end of the incubation, the majority of the target entity bound to the binding site is from a relevant volume of the sample. In some embodiments, the incubation allows the target entity to bind to the binding site, and wherein the relevant volume is a portion of the sample that is above the binding site at the closed configuration.

In certain embodiments, the incubation time is in the range of 1 seconds to 10 seconds. In certain embodiments, the incubation time is in the range of 10 seconds to 30 seconds. In certain embodiments, the incubation time is in the range of 30 seconds to 60 seconds. In certain embodiments, the incubation time is in the range of 1 minutes to 5 minutes. In certain embodiments, the incubation time is in the range of 5 minutes to 10 minutes. In certain embodiments, the incubation time is in the range of 10 minutes to 30 minutes.

Present Embodiments

A method for performing a homogeneous nucleic acid detection assay comprising:
(a) obtaining a QMAX device comprising a first plate and a second plate, wherein
the first plate and the second plate, each comprises a sample contacting area for contacting a sample that contains one or more target nucleic acids;
the first plate comprises, on its sample contacting area, a binding site that comprises:
(i) surface amplification surface; and
(ii) target-specific nucleic acid probes that are immobilized on said amplification surface and that specifically binds to a part of the target nucleic acid; and the second plate comprises a sample contact area comprising a reagent storage site that comprises target-specific nucleic acid detection agents that specifically binds to another part of the target nucleic acid;

(b) depositing the sample on one or both of the plates when the plates are in an open configuration;

(c) closing the plates to a closed configuration; and.

(d), after (c), while the plates remain in the closed configuration and without any washing step, detecting the target nucleic acid by reading the sample contact area with a reading device to produce an image of signals;

wherein: (i) the thickness of the sample in the closed configuration, (ii) the concentration of labels dissolved in the sample in the closed configuration, and (iii) the amplification factor of the proximity-dependent amplification surface are configured such that labels that are indirectly bound to the nucleic acid probes via a target nucleic acid are visible without washing away any biological materials or labels that are not bound to the surface amplification surface;

wherein one of the configurations is an open configuration, in which the average spacing between the inner surfaces of the two plates is at least 200 um; and wherein another of the configurations is a close configuration, in which, at least part of the sample is between the two plates and the average spacing between the inner surfaces of the plates is less than 200 um.

A device for analyzing a homogenous sample comprising:
a first plate, a second plate, and a binding site, wherein
(a) the first and second plates are movable relative to each other into different configurations, and have, on its respective surface, a sample contact area for contacting a sample that contains a target analyte,
(b) the sample contact area on the first plate has a binding site that comprises:
(i) proximity-dependent signal amplification layer, and
(ii) target-specific nucleic acid probes that are attached to said proximity-dependent signal amplification layer that bind to part of a target nucleic acid;
(c) the sample contact area on the second plate comprising a reagent storage site that comprises target-specific nucleic acid detection agents that bind to another part of the target nucleic acid;

wherein one of the configurations is an open configuration;

wherein another of the configurations is a close configuration, in which, at least part of the sample is between the two plates; and wherein the thickness of the sample in the closed configuration, the concentration of the labels dissolved in the sample in the closed configuration, and the amplification factor of the proximity-dependent signal amplification layer are configured such that any the labels that are indirectly bound to the target-specific nucleic acid probes are visible without washing away of the unbound labels.

An apparatus comprising a thermal cycler and a device of embodiment 2.

An apparatus comprising a thermal cycler, a device of embodiment 2, and a reader for real-time PCR.

A method for rapid nucleic acid detection assay comprising:
(a) obtaining a QMAX device comprising a first plate and a second plate, wherein
the first plate and the second plate, each comprises a sample contacting area for contacting a sample that contains one or more target nucleic acids;

the first plate comprises, on its sample contacting area, a binding site that comprises target-specific nucleic acid probes that are immobilized on the site and that specifically binds to part of the target nucleic acid; and the second plate comprises a sample contact area comprising a reagent storage site that comprises target-specific nucleic acid detection agents that specifically binds to another part of the target nucleic acid;

(b) depositing the sample on one or both of the plates when the plates are in an open configuration;

(c) closing the plates to a closed configuration for incubation for a period of time; and.

(d) opening the plates and pressing the plate again a washing sponge that has washing solution for a period of time and then releasing the washing sponge;

(e), after (d), reading the sample contact area with a reading device to produce an image of signals;

wherein: (i) the thickness of the sample in the closed configuration, (ii) the concentration of labels dissolved in the sample in the closed configuration, and (iii) the amplification factor of the proximity-dependent amplification surface are configured such that labels that are indirectly bound to the nucleic acid probes via a target nucleic acid are visible without washing away any biological materials or labels that are not bound to the proximity-dependent amplification surface;

wherein one of the configurations is an open configuration, in which the average spacing between the inner surfaces of the two plates is at least 200 um; and wherein another of the configurations is a close configuration, in which, at least part of the sample is between the two plates and the average spacing between the inner surfaces of the plates is less than 200 um.

The device, apparatus or method of any prior embodiment, wherein the spacing between the first plate and the second plate in the closed configuration is configured to make saturation binding time of the target analyte to the capture agents 300 sec or less.

The device, apparatus or method of any prior embodiment, wherein the spacing between the first plate and the second plate in the closed configuration is configured to make saturation binding time of the target analyte to the capture agents 300 sec or less.

The device, apparatus or method of any prior embodiment, wherein the spacing between the first plate and the second plate in the closed configuration is configured to make saturation binding time of the target analyte to the capture agents 60 sec or less.

The device, apparatus or method of any prior embodiment, wherein the target nucleic acid is a DNA or RNA, including genomic DNA, cfDNA, cDNA ctDNA, mRNA and miRNA.

The device, apparatus or method of any prior embodiment, wherein the time from step (b) to obtaining a result is less than 10 min.

The device, apparatus or method of any prior embodiment, wherein the thickness of the sample in the closed configuration, the concentration of the labels dissolved in the sample in the closed configuration, and the amplification factor of the surface amplification layer are configured such that any the labels that are bound directly or indirectly to the probles are visible in the closed configuration without washing away of the unbound labels.

The device, apparatus or method of any prior embodiment, wherein he labels bound to the proximity-dependent amplification surface are visible in less than 60 seconds.

The device, apparatus or method of any prior embodiment, wherein, wherein the labels bound to the proximity-dependent amplification surface are visible in less than 60 seconds.

The device, apparatus or method of any prior embodiment, wherein, wherein the storage site is approximately above the binding site on the first plate in the closed configuration.

The device, apparatus or method of any prior embodiment, wherein, wherein the target-specific nucleic acid probes and the target-specific nucleic acid detection agents form a sandwich that comprises the label.

The device, apparatus or method of any prior embodiment, wherein, wherein the signals are read without using a wash step to remove any biological materials or labels that are not bound to the amplification surface.

The device, apparatus or method of any prior embodiment, wherein, wherein the labels bound to the amplification surface are read by counting individual binding events.

The device, apparatus or method of any prior embodiment, wherein, wherein the labels bound to the amplification surface are read by a lump-sum reading method.

The device, apparatus or method of any prior embodiment, wherein, wherein the assay has a detection sensitivity of 0.1 nM or less.

The device, apparatus or method of any prior embodiment, wherein, wherein the assay comprises using a sponge to remove biological materials or labels that are not bound to the amplification surface.

The device, apparatus or method of any prior embodiment, wherein, wherein the signal amplification layer comprises a D2PA.

The device, apparatus or method of any prior embodiment, wherein, wherein the signal amplification layer comprises a layer of metallic material.

The device, apparatus or method of any prior embodiment, wherein, wherein the signal amplification layer comprises a continuous metallic film that is made of a material selected from the group consisting of gold, silver, copper, aluminum, alloys thereof, and combinations thereof.

The device, apparatus or method of any prior embodiment, wherein, wherein the different metals layers either locally enhance or act as a reflector, or both, to enhance an optical signal.

The device, apparatus or method of any prior embodiment, wherein, wherein the signal amplification layer comprises a layer of metallic material and a dielectric material on top of the metallic material layer, wherein the capture agent is on the dielectric material.

The device, apparatus or method of any prior embodiment, wherein, wherein the metallic material layer is a uniform metallic layer, nanostructured metallic layer, or a combination.

The device, apparatus or method of any prior embodiment, wherein, wherein the amplifies signals by plasmonic enhancement.

The device, apparatus or method of any prior embodiment, wherein, wherein assay comprises detecting the labels by Raman scattering.

The device, apparatus or method of any prior embodiment, wherein, wherein the sample contact area of the first plate further comprises a site that comprises the proximity-dependent amplification surface but not the target-specific nucleic acid probes.

The device, apparatus or method of any prior embodiment, wherein the assay comprises calculating a background signal by reading the site that comprises the proximity-dependent amplification surface but not the target-specific nucleic acid probes.

The device or method of any prior embodiment, wherein the device further comprise spacers fixed on one of the plate, wherein the spacers regulate the spacing between the first plate and the second plate in the closed configuration.

The device or method of any prior embodiment, wherein the amplification factor of the surface amplification layer is adjusted to make the optical signal from a single label that is bound directly or indirectly to the capture agents visible.

In the device or method herein described, the spacers can have a height of 100 nm, 1 um, 5 um, 10 um, 20 um, 50 um, 500 um, 1 mm, or a range between any two of the values; and a preferred range of 500 nm to 1 um, 1 um to 10 um, or 10 um to 30 um, 30 um to 50 um.

In the device or method herein described, the spacers can have a height of 1 um or less, thereby the saturation incubation time (or saturation binding time) is less than 0.1 s for protein, 0.1 s for nucleic acid (20 bp).

In the device or method herein described, the spacers can have a height of 2 um or less, thereby the saturation incubation time (or saturation binding time) is less than 0.3 s for protein, 0.1 s for nucleic acid (20 bp).

In the device or method herein described, the spacers can have a height of 5 um or less, thereby the saturation incubation time (or saturation binding time) is less than 2 s for protein, 1 s for nucleic acid (20 bp).

In the device or method herein described, the spacers can have a height of 10 um or less, thereby the saturation incubation time (or saturation binding time) is less than 10 s for protein, 5 s for nucleic acid (20 bp).

In the device or method herein described, the spacers can have a height of 30 um or less, thereby the saturation incubation time (or saturation binding time) is less than for 60 s protein, 30 s for nucleic acid (20 bp).

In the device or method herein described, the spacers can have a height of 50 um or less, thereby the saturation incubation time (or saturation binding time) is less than 2 min for protein, 1 min for nucleic acid (20 bp).

In the device or method herein described, the spacers can have a height of 100 um or less, thereby the saturation incubation time (or saturation binding time) is less than 10 min for protein, 5 min for nucleic acid (20 bp).

Related Documents

The present invention includes a variety of embodiments, which can be combined in multiple ways as long as the various components do not contradict one another. The embodiments should be regarded as a single invention file: each filing has other filing as the references and is also referenced in its entirety and for all purpose, rather than as a discrete independent. These embodiments include not only the disclosures in the current file, but also the documents that are herein referenced, incorporated, or to which priority is claimed.

(10) Definitions

The terms used in describing the devices, systems, and methods herein disclosed are defined in the current application, or in PCT Application (designating U.S.) Nos. PCT/US2016/045437 and PCT/US0216/051775, which were respectively filed on Aug. 10, 2016 and Sep. 14, 2016, US Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF card) that regulate the spacing between the plates. The term "X-plate" refers to one of the two plates in a CROF card, wherein the spacers are fixed to this plate. More descriptions of the COF Card, CROF Card, and X-plate are given in the provisional application Ser. No. 62/456,065, filed on Feb. 7, 2017, which is incorporated herein in its entirety for all purposes.

(11) Q-Card, Spacer and Uniform Sample Thickness

The devices, systems, and methods herein disclosed can include or use Q-cards, spacers, and uniform sample thickness embodiments for sample detection, analysis, and quantification. In some embodiments, the Q-card comprises spacers, which help to render at least part of the sample into a layer of high uniformity. The structure, material, function, variation and dimension of the spacers, as well as the uniformity of the spacers and the sample layer, are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456, 504, which was filed on Feb. 8, 2017, all of which applications are incorporated herein in their entireties for all purposes.

(12) Hinges, Opening Notches, Recessed Edge and Sliders

The devices, systems, and methods herein disclosed can include or use Q-cards for sample detection, analysis, and quantification. In some embodiments, the Q-card comprises hinges, notches, recesses, and sliders, which help to facilitate the manipulation of the Q card and the measurement of the samples. The structure, material, function, variation and dimension of the hinges, notches, recesses, and sliders are herein disclosed, or listed, described, and summarized in PCT Application (designating U.S.) Nos. PCT/US2016/ 045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(13) Q-Card, Sliders, and Smartphone Detection System

The devices, systems, and methods herein disclosed can include or use Q-cards for sample detection, analysis, and quantification. In some embodiments, the Q-cards are used together with sliders that allow the card to be read by a smartphone detection system. The structure, material, function, variation, dimension and connection of the Q-card, the sliders, and the smartphone detection system are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456, 504, which was filed on Feb. 8, 2017, all of which applications are incorporated herein in their entireties for all purposes.

(14) Detection Methods

The devices, systems, and methods herein disclosed can include or be used in various types of detection methods. The detection methods are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, US Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(15) Labels, Capture Agent and Detection Agent

The devices, systems, and methods herein disclosed can employ various types of labels, capture agents, and detection agents that are used for analytes detection. The labels are herein disclosed, or listed, described, and summarized in PCT Application (designating U.S.) Nos. PCT/US2016/ 045437 and PCT/US0216/051775, which were respectively filed on Aug. 10, 2016 and Sep. 14, 2016, US Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(16) Analytes

The devices, systems, and methods herein disclosed can be applied to manipulation and detection of various types of analytes (including biomarkers). The analytes and are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456, 504, which was filed on Feb. 8, 2017, all of which applications are incorporated herein in their entireties for all purposes.

(17) Applications (Field and Samples)

The devices, systems, and methods herein disclosed can be used for various applications (fields and samples). The applications are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(18) Cloud

The devices, systems, and methods herein disclosed can employ cloud technology for data transfer, storage, and/or analysis. The related cloud technologies are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, US Provisional Application No. 62/456,065, which was filed on Feb. 7, 2017, U.S. Provisional Application No. 62/456,287, which was filed on Feb. 8, 2017, and U.S. Provisional Application No. 62/456, 504, which was filed on Feb. 8, 2017, all of which applications are incorporated herein in their entireties for all purposes.

Without any intention to limit the use of the present method and device, in some embodiments, the method may be employed to identify a microbial pathogen from a clinical sample. In these embodiments, the target sequences may be from multiple different pathogens (e.g., at least 10 or at least 100 different pathogens), without knowing which pathogen is responsible for an infection, Microbes that might be identified using the present methods, compositions and kits include but are not limited to: a plurality of species of Gram (+) bacteria, plurality of species of Gram (−) bacteria, a plurality of species of bacteria in the family Enterobacteriaceae, a plurality of species of bacteria in the genus *Enterococcus*, a plurality of species of bacteria in the genus *Staphylococcus*, and a plurality of species of bacteria in the genus *Campylobacter, Escherichia coli (E. coli), E. coli* of various strains such as, K12-MG1655, CFT073, O157:H7 EDL933, O157:H7 VT2-Sakai, etc., *Streptococcus pneumoniae, Pseudomonas aeruginosa, Staphylococcus aureus*, coagulase-negative staphylococci, a plurality of *Candida* species including *C. albicans, C. tropicalis, C. dubliniensis, C. viswanathii, C. parapsilosis, Klebsiella pneumoniae*, a plurality of *Mycobacterium* species such as *M. tuberculosis, M. bovis, M. bovis* BCG, *M. scrofulaceum, M. kansasii, M. chelonae, M. gordonae, M. ulcerans, M. genavense, M. xenoi, M. simiae, M. fortuitum, M. malmoense, M. celatum, M. haemophilum* and *M. africanum, Listeria species, Chlamydia species, Mycoplasma species, Salmonella species, Brucella species, Yersinia* species, etc. Thus, the subject method enables identification of microbes to the level of the genus, species, sub-species, strain or variant of the microbe.
Additional Notes Further examples of inventive subject matter according to the present disclosure are described in the following enumerated paragraphs.

It must be noted that as used herein and in the appended claims, the singular forms "a", "an", and "the" include plural referents unless the context clearly dictates otherwise, e.g., when the word "single" is used. For example, reference to "an analyte" includes a single analyte and multiple analytes, reference to "a capture agent" includes a single capture agent and multiple capture agents, reference to "a detection agent" includes a single detection agent and multiple detection agents, and reference to "an agent" includes a single agent and multiple agents.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function. Similarly, subject matter that is recited as being configured to perform a particular function may additionally or alternatively be described as being operative to perform that function.

As used herein, the phrase, "for example," the phrase, "as an example," and/or simply the terms "example" and "exemplary" when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

As used herein, the phrases "at least one of" and "one or more of," in reference to a list of more than one entity, means any one or more of the entity in the list of entity, and is not limited to at least one of each and every entity specifically listed within the list of entity. For example, "at least one of A and B" (or, equivalently, "at least one of A or B," or, equivalently, "at least one of A and/or B") may refer to A alone, B alone, or the combination of A and B.

As used herein, the term "and/or" placed between a first entity and a second entity means one of (1) the first entity, (2) the second entity, and (3) the first entity and the second entity. Multiple entity listed with "and/or" should be construed in the same manner; i.e., "one or more" of the entity so conjoined. Other entity may optionally be present other than the entity specifically identified by the "and/or" clause, whether related or unrelated to those entities specifically identified.

Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

The invention claimed is:

1. A method for performing a homogeneous nucleic acid detection assay comprising:
   (a) obtaining a device for a nucleic acid hybridization assay comprising
      (i) a first plate and a second plate that are movable relative to each other into different configurations, including an open configuration and a closed configuration,
      (ii) first plate and the second plate each comprises a sample contact area for contacting a sample that contains or is suspected of containing a target analyte comprising one or more target nucleic acids;
      (iii) the sample contact area of the first plate comprises a binding site comprising target-specific nucleic acid probes that are immobilized and that specifically binds to a part of the target nucleic acid;
      (iv) one of the sample contact areas comprises a reagent storage site comprising target-specific nucleic acid detection agents that bind to another part of the target nucleic acid,
      (v) one or both of the plates comprise the spacers that are fixed with a respective sample contact area, wherein the spacers have a pillar shape, a predetermined substantially uniform height and a predetermined inter-spacer distance, wherein at least one of the spacers is inside the sample contact area;
      (vi) one or both of the plates is flexible, and the thickness of the flexible plate times the Young's modulus of the flexible plate is in the range 60 to 750 GPa-µm;
      (vii) the fourth power of the inter-spacer-distance (ISD) divided by the thickness of the flexible plate (h) and the Young's modulus (E) of the flexible plate, $ISD^4/(hE)$, is equal to or less than $5\times10^6$ um$^3$/GPa; and
      (viii) the plates are coupled by a hinge that is configured to transition the plates between an open configuration and a closed configuration;
   (b) depositing the sample on one or both of the plates when the plates are in the open configuration;
   (c) closing the plates to the closed configuration, wherein the labeled detection agent, upon contacting the sample, dissolves into the sample and diffuse in the sample; and
   (d) after (c), while the plates remain in the closed configuration and without any washing step, detecting the label of the labeled detection agent by reading the sample contact area of the first plate with a reading device to produce an image of signals;
   wherein: (i) the thickness of the sample in the closed configuration, and (ii) the concentration of the target-specific nucleic acid detection agent dissolved in the sample in the closed configuration are configured such that target-specific nucleic acid detection agents that are indirectly bound to the target-specific nucleic acid probes via a target nucleic acid are visible without washing away any biological materials and the labeled detection agent;
   wherein the open configuration is the configuration in which the average spacing between the inner surfaces of the two plates is at least 200 um; and
   wherein the closed configuration which is configured after the sample deposition in the open configuration; and in the closed configuration: at least part of the sample is compressed by the two plates into a layer of highly uniform thickness, wherein the uniform thickness of the layer is confined by the sample contact surfaces of the plates and is regulated by the plates and the spacers and the spacing between the inner surfaces of the plates is equal to 200 um or less.

2. The method of claim 1, wherein the sample contact area of the first plate further comprises a proximity-dependent signal amplification layer, wherein the capture agent is immobilized on the surface of the proximity-dependent signal amplification layer.

3. The method of claim 2, wherein, in the closed configuration, the thickness of the sample, the concentration of the target-specific nucleic acid detection agents dissolved in the sample, and the amplification factor of the surface amplification layer are configured such that target-specific nucleic acid detection agents that are bound directly or indirectly to target-specific nucleic acid analyte are visible in the closed configuration without washing away of the unbound target-specific nucleic acid detection agents.

4. The method of claim 2, wherein the labels bound to the proximity-dependent signal amplification layer are read by counting individual binding events.

5. The method of claim 2, wherein the proximity-dependent signal amplification layer comprises a disk-coupled dots-on-pillar antenna-array (D2PA).

6. The method of claim 2, wherein the proximity-dependent signal amplification layer comprises a layer of metallic material.

7. The method of claim 2, wherein the proximity-dependent signal amplification layer comprises a continuous metallic film that is made of a material selected from the group consisting of gold, silver, copper, aluminum, alloys thereof, and combinations thereof.

8. The method of claim 2, wherein the proximity-dependent signal amplification layer comprises a layer of metallic material and a dielectric material on top of the metallic material layer, wherein the target-specific nucleic acid probes are on the dielectric material.

9. The method of claim 2, wherein the metallic material layer is a uniform metallic layer, nanostructured metallic layer, or a combination.

10. The method of claim 2, wherein enhancement of the signals by the amplification surface is by plasmonic enhancement.

11. The method of claim 2, wherein the amplification factor of the proximity-dependent signal amplification layer is adjusted to make the optical signal from a single label that is bound directly or indirectly to the target-specific nucleic acid probes visible.

12. The method of claim 2, wherein the amplification factor of the surface amplification layer is adjusted to make the optical signal from a single label that is bound directly or indirectly to the target-specific nucleic acid probes visible.

13. The method of claim 2, wherein, in the closed configuration, the majority of the target analyte binds to the target-specific nucleic acid probes in 300 seconds or less.

14. The method of claim 2, wherein, in the closed configuration, the majority of the target analyte binds to the target-specific nucleic acid probes in 60 seconds or less.

15. The method of claim 2, wherein the target nucleic acid is a DNA or RNA, including genomic DNA, cfDNA, cDNA ctDNA, mRNA and miRNA.

16. The method of claim 2, wherein the time from depositing the sample on one or both of the plates in step (b) to reading the sample contact area in step (d) is less than 10 minutes.

17. The method of claim 2, wherein the target-specific nucleic acid detection agents that are bound indirectly to the target-specific nucleic acid probes via a target nucleic acid are visible in less than 60 seconds after the closing the plates to the closed configuration in step (c).

18. The method of claim 2, wherein the storage site is approximately above the binding site on the first plate in the closed configuration.

19. The method of claim 2, wherein the target-specific nucleic acid probes and the target-specific nucleic acid detection agents form a sandwich that comprises the label.

20. The method of claim 2, wherein the labels bound to the proximity-dependent signal amplification layer are read by counting individual binding events.

21. The method of claim 2, wherein the labels bound to the proximity-dependent signal amplification layer are read by a lump-sum reading method.

22. The method of claim 2, wherein the assay has a detection sensitivity of 0.1 nM or less.

23. The method of claim 2, wherein the sponge removes biological materials or target-specific nucleic acid detection agents that are not bound to the proximity-dependent amplification layer.

24. The method of claim 2, wherein the proximity-dependent signal amplification layer comprises a disk-coupled dots-on-pillar antenna-array (D2PA).

25. The method of claim 2, wherein the signal amplification layer comprises a layer of metallic material.

26. The method of claim 2, wherein the proximity-dependent signal amplification layer comprises a continuous metallic film that is made of a material selected from the group consisting of gold, silver, copper, aluminum, alloys thereof, and combinations thereof.

27. The method of claim 2, wherein the proximity-dependent signal amplification layer comprises a layer of metallic material, and wherein the metallic material layer either locally enhances or acts as a reflector, or both, to enhance an optical signal.

28. The method of claim 2, wherein the proximity-dependent signal amplification layer comprises a layer of metallic material and a dielectric material on top of the metallic material layer, wherein the target-specific nucleic acid probes are on the dielectric material.

29. The method of claim 2, wherein the proximity-dependent signal amplification layer comprises a layer of metallic material, and wherein the metallic material layer is a uniform metallic layer, nanostructured metallic layer, or a combination.

30. The method of claim 2, wherein the signals are amplified by plasmonic enhancement.

31. The method of claim 2, wherein reading the sample contact area in step (e) comprises detecting the target-specific nucleic acid detection agents by Raman scattering.

32. The method of claim 2, wherein the sample contact area of the first plate further comprises a site that comprises the proximity-dependent signal amplification layer but not the target-specific nucleic acid probes.

33. The method of claim 2, wherein step (e) further comprises calculating a background signal by reading a site on the first plate that comprises the proximity-dependent signal amplification layer e but not the target-specific nucleic acid probes.

34. The method of claim 2, wherein the spacers are fixed on one of the plates, wherein the spacers regulate the spacing between the first plate and the second plate in the closed configuration.

35. The method of claim 2, wherein the amplification factor of the proximity-dependent signal amplification layer is adjusted to make the optical signal from a single label that is bound directly or indirectly to the target-specific nucleic acid probes visible.

36. The method of claim 1, wherein, in the closed configuration, the majority of the target analyte binds to the capture agent in 300 seconds or less.

37. The method of claim 1, wherein, in the closed configuration, the majority of the target analyte binds to the target-specific nucleic acid probes in 60 seconds or less.

38. The method of claim 1, wherein the target nucleic acid is a DNA or RNA, including genomic DNA, cfDNA, cDNA ctDNA, mRNA and miRNA.

39. The method of claim 1, wherein the device further comprising a thermal cycler.

40. The method of claim 1, wherein the target-specific nucleic acid detection agents that are bound indirectly to the target-specific nucleic acid probes via a target nucleic acid are visible in less than 60 seconds after closing the plates to the closed configuration in step (c).

41. The method of claim 1, wherein the storage site is approximately above the binding site on the first plate in the closed configuration.

42. The method of claim 1, wherein the target-specific nucleic acid probes and the target-specific nucleic acid detection agents form a sandwich that comprises the label.

43. The method of claim 1, wherein the sensitivity of the detection is 0.1 nM or less.

44. The method of claim 1, wherein the method further comprising a step of using a sponge to remove biological materials or labels that are not bound to the target-specific nucleic acid analytes.

45. The method of claim 1, wherein the sample contact area of the first plate further comprises a metallic material layer that either locally enhances or acts as a reflector, or both, to enhance an optical signal.

46. The method of claim 1, wherein the one or more target nucleic acid analytes are detected in step (d) by Raman scattering.

47. The method of claim 1, wherein the sample contact area of the first plate further comprises a site that comprises the proximity-dependent signal amplification layer but not the target-specific nucleic acid probes.

48. The method of claim 1, wherein step (d) further comprises calculating a background signal by reading a site on the first plate that comprises the proximity-dependent signal amplification layer but not the target-specific nucleic acid probes.

* * * * *